US010729756B2

(12) United States Patent
Faaberg et al.

(10) Patent No.: US 10,729,756 B2
(45) Date of Patent: Aug. 4, 2020

(54) VIABLE VIRUSES WITH FOREIGN TAGS

(71) Applicant: The United States of America, as represented by the Secretary of Agriculture, Washington, DC (US)

(72) Inventors: Kay S. Faaberg, Ames, IA (US); Allyn Spear, Fishers, IN (US); Matthew A. Kappes, Elkridge, MD (US); Kelly M. Lager, Colo, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 113 days.

(21) Appl. No.: 15/989,454

(22) Filed: May 25, 2018

(65) Prior Publication Data

US 2018/0344837 A1    Dec. 6, 2018

Related U.S. Application Data

(60) Provisional application No. 62/512,281, filed on May 30, 2017.

(51) Int. Cl.
*A61K 39/12* (2006.01)
*A61P 31/14* (2006.01)
*C12N 7/04* (2006.01)
*A61K 39/00* (2006.01)

(52) U.S. Cl.
CPC .............. *A61K 39/12* (2013.01); *A61P 31/14* (2018.01); *C12N 7/04* (2013.01); *A61K 2039/5254* (2013.01); *A61K 2039/53* (2013.01); *A61K 2039/575* (2013.01); *C12N 2770/10021* (2013.01); *C12N 2770/10034* (2013.01); *C12N 2770/10062* (2013.01)

(58) Field of Classification Search
None
See application file for complete search history.

(56) References Cited

U.S. PATENT DOCUMENTS

| | | | | |
|---|---|---|---|---|
| 8,609,827 | B2 * | 12/2013 | Calvert | C07K 14/005 536/23.72 |
| 2010/0136047 | A1 | 6/2010 | Fang et al. | |
| 2010/0267929 | A1 | 10/2010 | Faaberg et al. | |
| 2011/0040079 | A1 * | 2/2011 | Calvert | C07K 14/005 536/23.72 |
| 2013/0183329 | A1 * | 7/2013 | Zhang | A61K 39/12 424/186.1 |
| 2018/0344837 | A1 * | 12/2018 | Faaberg | A61K 39/12 |

OTHER PUBLICATIONS

Wang et al. (Research in Veterinary Science. 2013; 95: 1-7).*
Kim et al. (Virus Research. 2007; 128: 106-114).*
Alignment of SEQ ID 3 with Geneseq db access No. BAQ55794 by Zhang et al in USPgPub2013183329.*
Alignment of SEQ ID 5 with Geneseq db access No. BAQ55794 by Zhang et al in USPgPub2013183329.*
Alignment of SEQ ID 13 with Geneseq db access No. BAQ55794 by Zhang et al in USPgPub2013183329.*
Alignment of SEQ ID 15 with Geneseq db access No. BAQ55794 by Zhang et al in USPgPub2013183329.*
Alignment of SEQ ID 17 with Geneseq db access No. BAQ55794 by Zhang et al in USPgPub2013183329.*
Alignment of SEQ ID 19 with Geneseq db access No. BAQ55794 by Zhang et al in USPgPub2013183329.*
Alignment of SEQ ID 21 with Geneseq db access No. BAQ55794 by Zhang et al in USPgPub2013183329.*
Alignment of SEQ ID 23 with Geneseq db access No. BAQ55794 by Zhang et al in USPgPub2013183329.*
Greenspan et al (Nature Biotechnology.1999; 7: 936-937).*
Han et al. (Journal of Virology. 2007; 81 (18): 9878-9890).*
Han et al. (Journal of Virology. 2009; 83 (18): 9449-9463).*
Faaberg et al. (Virus Research. 2010; 154: 77-85).*
Yuan, Shishan et al., "Heteroclite Subgenomic RNAs Are Produced in Porcine Reproductive and Respiratory Syndrome Virus Infection," Virology, (2000), 275:158-169.
Yuan, Shishan et al., "Characterization of heteroclite subgenomic RNAs associated with PRRSV infection," Virus Research, (2004), 105:75-87.
De Lima, Marcelo et al., "Development of a porcine reproductive and respiratory syndrome virus differentiable (DIVA) strain through deletion of specific immunodominant epitopes," Vaccine, (2008), 26:3594-3600.
Zhou, Lei et al., "The 30-Amino-Acid Deletion in the Nsp2 of Highly Pathogenic Porcine Reproductive and Respiratory Syndrome Virus Emerging in China Is Not Related to Its Virulence," Journal of Virology, (2009), 83(10):5156-5167.
International Searching Authority, PCT/US2018/034917 for the United States of America, as Represented by the Secretary of Agriculture, International Filing Date May 29, 2018.
Botner, A. et al., "Appearance of acute PRRS-like symptoms in sow herds after vaccination with a modified live PRRS vaccine," Veterinary Record, (1997), 141:497-499.
Faaberg, Kay S. et al., "In vivo growth of porcine reproductive and respiratory syndrome virus engineered nsp2 deletion mutants," Virus Research, (2010), 154:77-85.
Guo, Baoqino et al., "Large scale parallel pyrosequencing technology: PRRSV strain VR-2332 nsp2 deletion mutant stability in swine!," Virus Research, (2011), 161:162-169.

(Continued)

*Primary Examiner* — Shanon A. Foley
(74) *Attorney, Agent, or Firm* — John Fado; Ariel Atkinson

(57) ABSTRACT

Multiple DIVA vaccines effective against porcine reproductive and respiratory syndrome virus (PRRSV) are disclosed. The DIVA vaccines may be negative DIVAs or positive DIVAs. The DIVA vaccines may be produced by modifying the nsp2 region of a modified live virus vaccine. The modification may be one or more deletions only (negative DIVAs) or a deletion with an insertion (positive DIVAs). The insertion may be of an epitope tag, such as a V5, S-Tag, or FLAG tag. Produced DIVA vaccines may be stable through multiple passes and thus may be effective for production and vaccination of animals.

6 Claims, 9 Drawing Sheets
(3 of 9 Drawing Sheet(s) Filed in Color)
Specification includes a Sequence Listing.

(56) References Cited

OTHER PUBLICATIONS

Guo, Baoqino et al., "Experimental infection of United States swine with a Chinese highly pathogenic strain of porcine reproductive and respiratory syndrome virus," Virology, (2013), 435:372-384.

Guo, Baoqino et al., "Chinese and Vietnamese strains of HP-PRRSV cause different pathogenic outcomes in United States high health swine," Virology, (2013), 446:238-250.

Han, Jun et al., "Identification of Nonessential Regions of the nsp2 Replicase Protein of Porcine Reproductive and Respiratory Syndrome Virus Strain VR-2332 for Replication in Cell Culture," Journal of Virology, (2007), 81(18):9878-9890.

Hanada, Kousuke et al., "The Origin and Evolution of Porcine Reproductive and Respiratory Syndrome Viruses," Molecular Biology and Evolution, (2005), 22(4):1024-1031.

Holtkamp, Derald J. et al., "Assessment of the economic impact of porcine reproductive and respiratory syndrome virus on United States pork producers," Journal of Swine Health and Production, (2013), 21(2):72-84.

Jeong, Jiwoon et al., "Evaluation of a 20 year old porcine reproductive and respiratory syndrome (PRRS) modified live vaccine (Ingelvac® PRRS MLV) against two recent type 2 PRRS virus isolates in South Korea," Veterinary Microbiology, (2016), 192:102-109.

Kappes, Matthew A. et al., "PRRSV structure, replication and recombination: Origin of phenotype and genotype diversity," Virology, (2015), pp. 479-480 & 475-486.

Martinez-Lobo, Francisco Javier et al., "Safety of Porcine Reproductive and Respiratory Syndrome Modified Live Virus (MLV) vaccine strains in a young pig infection model," Veterinary Research, (2013), 44:115-129.

Mengeling, William L. et al., "Identification and clinical assessment of suspect vaccine-related field strains of porcine reproductive and respiratory syndrome virus," Am J. Vet Res, (1999), 60(3): 334-340.

Nielsen, Henriette S. et al., "Reversion of a live porcine reproductive and respiratory syndrome virus vaccine investigated by parallel mutations," Journal of General Virology, (2001), 82:1263-1272.

Pileri, Emanuela et al., "Review on the transmission porcine reproductive and respiratory syndrome virus between pigs and farms and impact on vaccination," Veterinary Research, (2016), 47:108-121.

Shi, Mang et al., "Molecular epidemiology of PRRSV: A phylogenetic perspective," Virus Research, (2010), 154:7-17.

Shi, Mang et al., "Recombination Is Associated with an Outbreak of Novel Highly Pathogenic Porcine Reproductive and Respiratory Syndrome Viruses in China," Journal of Virology, (2013), 87(19):10904-10907.

Snijder, Eric J. et al., "Arterivirus molecular biology and pathogenesis," Journal of General Virology, (2013), 94:2141-2163.

Wang, Yue et al., Attenuation of porcine reproductive and respiratory syndrome virus strain MN184 using chimeric construction with vaccine sequence, Virology, (2008), 371:418-429.

* cited by examiner

| Lane Number | Virus | Primer Set A | Enzyme | Fragment Sizes | Primer Set C | Enzyme | Fragment Sizes |
|---|---|---|---|---|---|---|---|
| 1 | MLV | 535 | NaeI | 203, 332 | 705 | EcoRV | 280, 426 |
| 2 | Δ23 | 466 | NaeI | 203, 263 | 705 | EcoRV | 280, 426 |
| 3 | Δ23-V5 | 508 | XbaI | 216, 292 | 705 | XbaI | 705 |
| 4 | Δ23-FLAG | 532 | PsiI | 266, 270 | 705 | PsiI | 705 |
| 5 | Δ23-S | 511 | NotI | 238, 273 | 705 | NotI | 705 |
| 6 | Δ87 | 535 | NaeI | 203, 332 | 444 | EcoRV | 444 |
| 7 | Δ87-V5 | 535 | XbaI | 535 | 486 | XbaI | 231, 256 |
| 8 | Δ87-FLAG | 535 | PsiI | 535 | 510 | PsiI | 230, 280 |
| 9 | Δ87-S | 535 | NotI | 535 | 489 | NotI | 236, 253 |

VIABLE VIRUSES WITH FOREIGN TAGS

BACKGROUND

Porcine reproductive and respiratory syndrome virus (PRRSV), a member of the viral family Arteriviridae, causes respiratory disease in growing swine and fetal mortality. Efforts to contain this virus have included early diagnosis, enhanced bio security measures, herd management and application of vaccines (Holtkamp et al., 2013. Assessment of the economic impact of porcine reproductive and respiratory syndrome virus on United States pork producers. Journal of Swine Health and Production 21, 72-84; Pileri and Mateu, 2016. Review on the transmission porcine reproductive and respiratory syndrome virus between pigs and farms and impact on vaccination. Vet. Res. 47, 108). However, the available modified live vaccines (MLV) only provide partial protection against heterologous viruses and are dwarfed by the number of PRRSV strains circulating worldwide. PRRSV strains vary greatly and each exists as one of two genetically different types (Type 1 and 2). Each genotype continues to evolve by both imprecise replication due to its inherent polymerase error rate and by recombination (Hanada et al., 2005. The origin and evolution of porcine reproductive and respiratory syndrome viruses. Mol. Biol. Evol. 22, 1024-1031; Kappes and Faaberg, 2015. PRRSV structure, replication and recombination: Origin of phenotype and genotype diversity. Virology 479-480, 475-486; Shi et al., 2013. Recombination is associated with an outbreak of novel highly pathogenic porcine reproductive and respiratory syndrome viruses in China. J. Virol. 87, 10904-10907; Shi et al., 2010. Molecular epidemiology of PRRSV: a phylogenetic perspective. Virus Res. 154, 7-17). The swine industry is also hampered by the lack of a vaccine that effectively differentiates infected from vaccinated animals (DIVA).

In PRRSV infected cells, the nsp2 protein not only is present as a full-length protein but is processed into variably sized isomers (Wang, et al., 2008. Attenuation of porcine reproductive and respiratory syndrome virus strain MN184 using chimeric construction with vaccine sequence. Virology 371, 418-429; Yuan, et al., 2000. Heteroclite subgenomic RNAs are produced in porcine reproductive and respiratory syndrome virus infection. Virology 275, 158-169; Yuan, et al., 2004. Characterization of heteroclite subgenomic RNAs associated with PRRSV infection. Virus Res. 105, 75-87.

Ingelvac PRRS® MLV (MLV) is used widely in several countries to dampen the effect of PRRSV herd infection in young pigs, has been used safely for 20 years with few instances of reversion to virulence, replicates sufficiently in vaccinated swine and is a low cost platform that is affordable for the industry (Botner et al., 1997. Appearance of acute PRRS-like symptoms in sow herds after vaccination with a modified live PRRS vaccine. Vet. Rec. 141, 497-499; Jeong et al., 2016. Evaluation of a 20 year old porcine reproductive and respiratory syndrome (PRRS) modified live vaccine (Ingelvac((R)) PRRS MLV) against two recent type 2 PRRS virus isolates in South Korea. Vet. Microbiol. 192, 102-109; Martinez-Lobo et al., 2013. Safety of Porcine Reproductive and Respiratory Syndrome Modified Live Virus (MLV) vaccine strains in a young pig infection model. Vet. Res. 44, 115; Mengeling et al., 1999. Identification and clinical assessment of suspected vaccine-related field strains of porcine reproductive and respiratory syndrome virus. Am. J. Vet. Res. 60, 334-340; Nielsen et al., 2001. Reversion of a live porcine reproductive and respiratory syndrome virus vaccine investigated by parallel mutations. J. Gen. Virol. 82, 1263-1272). Type 2 strain VR-2332, the parent of MLV, causes a mild disease under defined conditions, thus concerns of simple reversion to virulence are reduced. Moreover, VR-2332 replicates at a lower rate in swine and does not result in a reduction in weight gain when compared to more pathogenic isolates (Guo et al., 2013. Experimental infection of United States swine with a Chinese highly pathogenic strain of porcine reproductive and respiratory syndrome virus. Virology 435, 372-384; Guo et al., 2013. Chinese and Vietnamese strains of HP-PRRSV cause different pathogenic outcomes in United States high health swine. Virology 446, 238-250).

All of the references cited herein, including U.S. Patents and U.S. Patent Application Publications, are incorporated by reference in their entirety.

SUMMARY

According to at least one aspect of the invention, an immunogenic composition may include an isolated polynucleotide sequence representing a modified live vaccine for porcine reproductive and respiratory syndrome virus having an nsp2 region, wherein the nsp2 region has a modification at one of amino acids 10-14, the modification includes a deletion, and the immunogenic composition is capable of inducing an immune response in a recipient.

According to a further aspect of the invention, the immunogenic composition may also include a pharmaceutically acceptable adjuvant.

According to a further aspect of the invention, the immunogenic composition may also include a pharmaceutically acceptable carrier.

According to a further aspect of the invention, the modification may be at amino acid 12.

According to a further aspect of the invention, the amino acid sequence of the nsp2 region may be one of a sequence of SEQ ID NO: 3 and a sequence having at least 95% homology to SEQ ID NO: 3.

According to a further aspect of the invention, the modification may further include an insertion, and the insertion includes the insertion of an epitope tag of 10-25 amino acids in length.

According to a further aspect of the invention, the epitope tag may be one of a V5 tag, an S-Tag, and a FLAG tag.

According to a further aspect of the invention, the amino acid sequence of the nsp2 region may be one of a sequence of SEQ ID NO: 13, a sequence of SEQ ID NO: 15, a sequence of SEQ ID NO: 17, a sequence having at least 95% homology to SEQ ID NO: 13, a sequence having at least 95% homology to SEQ ID NO: 15, and a sequence having at least 95% homology to SEQ ID NO: 17.

According to another aspect of the invention, an immunogenic composition may include an isolated polynucleotide sequence representing a modified live vaccine for porcine reproductive and respiratory syndrome virus having an nsp2 region, wherein the nsp2 region has a modification at amino acid 724-728, the modification includes a deletion, and the immunogenic composition is capable of inducing an immune response in a recipient.

According to a further aspect of the invention, the modification may be at amino acid 726.

According to a further aspect of the invention, the amino acid sequence of the nsp2 region may be one of a sequence of SEQ ID NO: 5 and a sequence having at least 95% homology to SEQ ID NO: 5.

According to a further aspect of the invention, the modification may further include an insertion, and the insertion may include the insertion of an epitope tag of 10-25 amino acids in length.

According to a further aspect of the invention, the epitope tag may be one of a V5 tag, an S-Tag, and a FLAG tag.

According to a further aspect of the invention, the amino acid sequence of the nsp2 region may be one of a sequence of SEQ ID NO: 19, a sequence of SEQ ID NO: 21, a sequence of SEQ ID NO: 23, a sequence having at least 95% homology to SEQ ID NO: 19, a sequence having at least 95% homology to SEQ ID NO: 21, and a sequence having at least 95% homology to SEQ ID NO: 23.

According to another aspect of the invention, an immunogenic composition may include an isolated polynucleotide sequence representing a modified live vaccine for porcine reproductive and respiratory syndrome virus having an nsp2 region, wherein the nsp2 region includes a deletion at a deletion starting point, the deletion starting point being one of amino acids 10-14 or one of amino acids 724-728, the deletion including the removal of 21-89 amino acids, and the nsp2 region optionally includes an insertion of an epitope tag of 10-25 amino acids in length at the deletion starting point.

According to another aspect of the invention, a method for reducing the incidence of porcine reproductive and respiratory syndrome virus (PRRSV) in swine may include administering to a swine an immunogenic composition in an amount effective to generate an immune response in said swine to said PRRSV, wherein the immunogenic composition includes an isolated polynucleotide sequence representing a modified live vaccine for porcine reproductive and respiratory syndrome virus having an nsp2 region, the nsp2 region has a modification at one of amino acids 10-14 or one of amino acids 724-728, and the modification includes a deletion.

According to a further aspect of the invention, the immune response may be protection against porcine reproductive and respiratory syndrome virus.

According to a further aspect of the invention, the modification further includes an insertion, and the insertion includes the insertion of an epitope tag of 10-25 amino acids in length.

SEQUENCE LISTING

The Sequence Listing submitted via EFS-Web as an ASCII compliant text file format (.txt) filed May 30, 2017, named "SequenceListing-013316_ST25" (created on May 30, 2017, 126 kb), is hereby incorporated herein by reference in its entirety. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

The sequences used or referenced to in the present invention are described in Table 1:

TABLE 1

| Sequence Descriptions |
| --- |
| SEQ ID NO: 1 cDNA sequence encoding nsp2 region of pMLV |
| SEQ ID NO: 2 cDNA sequence encoding nsp2 region of nsp2Δ23 DIVA vaccine |
| SEQ ID NO: 3 Amino acid sequence of nsp2 region of nsp2Δ23 DIVA vaccine |
| SEQ ID NO: 4 cDNA sequence encoding nsp2 region of nsp2Δ87 DIVA vaccine |
| SEQ ID NO: 5 Amino acid sequence of nsp2 region of nsp2Δ87 DIVA vaccine |
| SEQ ID NO: 6 cDNA sequence encoding V5 tag |
| SEQ ID NO: 7 Amino acid sequence of V5 tag |
| SEQ ID NO: 8 cDNA sequence encoding S-Tag tag |
| SEQ ID NO: 9 Amino acid sequence of S-Tag tag |
| SEQ ID NO: 10 cDNA sequence encoding FLAG tag |
| SEQ ID NO: 11 Amino acid sequence of FLAG tag |
| SEQ ID NO: 12 cDNA sequence encoding nsp2 region of nsp2Δ23-V5 DIVA vaccine |
| SEQ ID NO: 13 Amino acid sequence of nsp2 region of nsp2Δ23-V5 DIVA vaccine |
| SEQ ID NO: 14 cDNA sequence encoding nsp2 region of nsp2Δ23-S-Tag DIVA vaccine |
| SEQ ID NO: 15 Amino acid sequence of nsp2 region of nsp2Δ23-S-Tag DIVA vaccine |
| SEQ ID NO: 16 cDNA sequence encoding nsp2 region of nsp2Δ23-FLAG DIVA vaccine |
| SEQ ID NO: 17 Amino acid sequence of nsp2 region of nsp2Δ23-FLAG DIVA vaccine |
| SEQ ID NO: 18 cDNA sequence encoding nsp2 region of nsp2Δ87-V5 DIVA vaccine |
| SEQ ID NO: 19 Amino acid sequence of nsp2 region of nsp2Δ87-V5 DIVA vaccine |
| SEQ ID NO: 20 cDNA sequence encoding nsp2 region of nsp2Δ87-S-Tag DIVA vaccine |
| SEQ ID NO: 21 Amino acid sequence of nsp2 region of nsp2Δ87-S-Tag DIVA vaccine |
| SEQ ID NO: 22 cDNA sequence encoding nsp2 region of nsp2Δ87-FLAG DIVA vaccine |
| SEQ ID NO: 23 Amino acid sequence of nsp2 region of nsp2Δ87-FLAG DIVA vaccine |
| SEQ ID NO: 24 cloning vector designated "pCHAZ" (circular) |
| SEQ ID NO: 25 Primer A1 used to verify non-contamination |
| SEQ ID NO: 26 Primer A2 used to verify non-contamination |
| SEQ ID NO: 27 Primer B1 used to verify non-contamination |
| SEQ ID NO: 28 Primer B2 used to verify non-contamination |
| SEQ ID NO: 29 Primer C1 used to verify non-contamination |
| SEQ ID NO: 30 Primer C2 used to verify non-contamination |
| SEQ ID NO: 31 Primer D1 used to verify non-contamination |
| SEQ ID NO: 32 Primer D2 used to verify non-contamination |
| SEQ ID NO: 33 Oligonucleotide probe used in Northern blot analysis for negative DIVAs |
| SEQ ID NO: 34 Oligonucleotide probe used in Northern blot analysis for V5-tagged DIVAs |
| SEQ ID NO: 35 Oligonucleotide probe used in Northern blot analysis for FLAG-tagged DIVAs |
| SEQ ID NO: 36 Oligonucleotide probe used in Northern blot analysis for S-tagged DIVAs |

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

Exemplary

Exemplary

Exemplary

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word “exemplary” means “serving as an example, instance or illustration.” The embodiments described herein are not limiting, but rather are exemplary only. It should be understood that the described embodiment are not necessarily to be construed as preferred or advantageous over other embodiments. Moreover, the terms “embodiments of the invention”, “embodiments” or “invention” do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term “about” refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The amounts, percentages, and ranges disclosed herein are not meant to be limiting, and increments between the recited amounts, percentages, and ranges are specifically envisioned as part of the invention.

“Optional” or “optionally” means that the subsequently described event or circumstance may or may not occur, and that the description includes instances in which said event or circumstance occurs and instances where it does not. For example, the phrase “optionally comprising X” means that the composition may or may not contain X, and that this description includes compositions that contain and do not contain X.

Because this invention involves production of genetically altered viruses and involves recombinant DNA techniques, the following definitions are provided to assist in describing this invention. The terms “isolated”, “purified”, or “biologically pure” as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term “purified” denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

For nucleic acids, sizes are given in either kilobases (kb) or base pairs (bp), or nucleotides (nt). Estimates are typically derived from agarose or acrylamide gel electrophoresis, from sequenced nucleic acids, or from published DNA sequences. For proteins, sizes are given in kiloDaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence for each amino acid substitution (alteration) also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98(1994)). Because of the degeneracy of nucleic acid codons, one can use various different polynucleotides to encode identical polypeptides. Table 2, infra, contains information about which nucleic acid codons encode which amino acids and is useful for determining the possible nucleotide substitutions that are included in this invention.

TABLE 2

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |

TABLE 2-continued

Figure 1A:
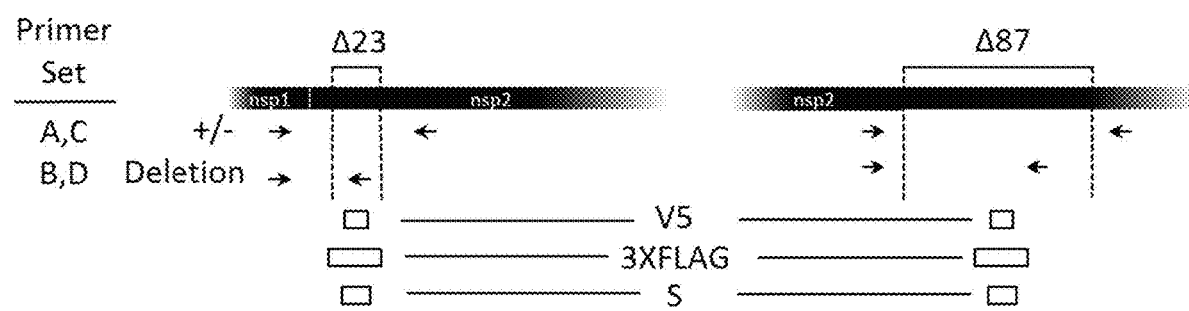
FIG. 1A shows a schematic representation of two negative DIVAs (Δ23 and Δ87), three potential insertion flags (V5, FLAG, and S), and primer sets which can be used to confirm no contamination is present.

| Amino acid | Nucleic acid codons |
|---|---|
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Stop | TAA, TGA, TAG |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "primer" refers to an oligonucleotide, which is capable of acting as a point of initiation of synthesis when placed under conditions in which primer extension is initiated. A primer may occur naturally, as in a purified restriction digest, or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

Oligonucleotides and polynucleotides that are not commercially available can be chemically synthesized e.g., according to the solid phase phosphoramidite triester method first described by Beaucage and Caruthers, Tetrahedron Letts. 22:1859-1862 (1981), or using an automated synthesizer, as described in Van Devanter et al., Nucleic Acids Res. 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, J. Chrom. 255:137-149 (1983).

The terms "identical" or percent "identity", in the context of two or more polynucleotides or polypeptide sequences, refer to two or more sequences or sub-sequences that are the same or have a specified percentage of nucleotides or amino acids (respectively) that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of various algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology*, 1995 supplement).

The "complement" of a particular polynucleotide sequence is that nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence (reverse complement).

As used herein, the term "promoter" refers to a polynucleotide that, in its native state, is located upstream or 5' to a translational start codon of an open reading frame (or protein-coding region) and that is involved in recognition and binding of RNA polymerase and other proteins (trans-acting transcription factors) to initiate transcription. The promoters that are predominately functional in a specific tissue or set of tissues are considered "tissue-specific promoters". A promoter can be used as a 5' regulatory element for modulating expression of a particular desired polynucleotide (heterologous polynucleotide) operably linked thereto. When operably linked to a transcribable polynucleotide, a promoter typically causes the transcribable polynucleotide to be transcribed in a manner that is similar to that of which the promoter is normally associated.

The term "vector" refers to DNA, RNA, a protein, or polypeptide that are to be introduced into a host cell or organism. The polynucleotides, protein, and polypeptide which are to be introduced into a host can be therapeutic or prophylactic in nature; can encode or be an antigen; can be regulatory in nature; etc. There are various types of vectors including viruses, viroids, plasmids, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette can have the heterologous polynucleotide operably linked to one or more transcription regulatory elements. As used herein, the term "operably linked" refers to a first polynucleotide, such as a promoter, connected with a second transcribable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly, a terminator is operably linked to the polynucleotide of interest if the terminator regulates or mediates transcription of the polynucleotide of interest, and in particular, the termination of transcription. Constructs of the present invention would typically contain a promoter operably linked to a transcribable polynucleotide operably linked to a terminator.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant viruses may express genes/polynucleotides that are not found within the native (non-recombinant or wild-type) form of the viruses or express native genes in an otherwise abnormal amount—over-expressed, under-expressed or not expressed at all—compared to the non-recombinant or wild-type sequence, polynucleotide, or organism.

A "vaccine" is defined herein as a biological agent which is capable of providing a protective response in an animal to which the vaccine has been delivered and is incapable of causing severe disease. Administration of the vaccine results in increased immunity from a disease; the vaccine stimulates antibody production or cellular immunity against the pathogen causing the disease. Immunity is defined herein as the induction of a significantly higher level of protection in a population of recipients, such as porcine, against mortality and clinical symptoms after vaccination compared to an unvaccinated group. In particular, the vaccine(s) according to the invention can: (a) protect a large proportion of vaccinated animals against the occurrence of clinical symptoms of the disease and mortality, or; (b) result in a significant decrease in clinical symptoms of the disease and mortality.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "DIVA" or "DIVA vaccine" refers to a vaccine which may be used to differentiate infected from vaccinated animals. Differentiation may be made according to any known method in the art which can substantially identify a DIVA-vaccinated organism from an infected organism. A DIVA vaccine may be, for example, a negative DIVA or a positive DIVA. A negative DIVA vaccine is a vaccine which has been modified by a deletion in one or more regions of its sequence relative to the corresponding region(s) of the virus. A positive DIVA vaccine is a vaccine which has been modified by an insertion in one or more regions of its sequence relative to the corresponding region(s) of the virus. The insertion may be a tag, such as an epitope tag, which may be used to positively identify the vaccine.

The deletions and/or insertions in a DIVA vaccine may vary in length. Deletions according to the present invention may be as small as 10 amino acids in length or as large as 120 amino acids in length (and the corresponding size in the encoding cDNA sequence(s)). Insertions may be as small as 8 amino acids in length or as large as 30 amino acids in length.

In some instances, vaccines of the present invention may also be administered with one or more adjuvants, which includes any material included in the vaccine formulation that enhances an immune response in the recipient that is induced by the vaccine.

An immunogenic composition may refer to a vaccine, optionally including one or more adjuvants, carriers, or other pharmaceutically acceptable materials. Immunogenic compositions may also be referred to as vaccine compositions.

Immunogenic compositions of the present invention can also comprise pharmaceutically or veterinarily acceptable carriers in addition to the recombinant protein component of the vaccine. Carriers utilized in practicing the vaccines provided herein can be any known in the art and can be liquid, solid, semi-solid, or gel. The type of formulation can be modified depending on the route of administration of the antigen. For example, if the vaccines of the present invention are applied parenterally (intramuscularly, intravascularly, or subcutaneously), a liquid formulation—such as an emulsion, suspension, or solution—may be preferred. For oral administration, the vaccines of the present invention can be applied to carriers such as pellets, tablets, kibbles, chewables, powders and beads, as well as specific materials such as microcrystalline cellulose (MCC), plant-based products and soil-based products (e.g., clays). Preferably, carriers are non-toxic to the recipient. In some instances the vaccines of the present invention, with or without carriers, can be presented to a recipient for ingestion via suspension in drinking water. One of skill in the art is readily able to choose such carriers for application to recipient animals such as porcine.

Vaccines in the present invention may be modified-live vaccines (MLV), which are also referred to as attenuated vaccines. An MLV is a vaccine is a vaccine based on a virus modified such that it no longer causes the same clinical symptoms when administered to a recipient. For example, swine administered with a MLV for PRRSV would not exhibit the same clinical symptoms they would if they had been directly infected by PRRSV.

Vaccines in the present invention involve the editing of nucleotide and/or amino acid sequences. Though examples of only specific modifications, i.e. deletions or additions, of certain sequence lengths and in certain locations within the sequences are given below, one of ordinary skill in the art would understand that minor modifications may also be useful in the present invention. For example, a deletion may start up to 6 nucleotide residues prior to or after the disclosed starting location, and a deletion may end up to 6 nucleotide residues prior to or after the disclosed ending location. Further, an insertion, such as a tag, may be exactly the same length as one of the disclosed tags or ±4 amino acids in length.

"Porcine" and "swine" are used interchangeably herein and refer to any animal that is a member of the family Suidae such as, for example, a pig.

Although the following Example uses a single parental strain, it is envisioned that the nsp2 region used in the present invention may be used as an insert and/or replacement in any other suitable viral strain.

EXAMPLES

To produce vaccine viruses capable of differentiating infected from vaccinated animals (DIVA) and to be useful as tags to follow virus infection of cultured cells or in animals, two deletion constructs of the parental pMLV strain (as produced from the PRRSV strain VR-2332, as described in Wang, et al, 2008; "Attenuation of porcine reproductive and respiratory syndrome virus strain MN184 using chimeric construction with vaccine sequence," Virology 371, 418-429) that had proven replication competent in MARC-145 cells [pV7-nsp2Δ23 (deletion of nsp2 N-terminal amino acids (aa) 12-34) and pV7-nsp2Δ87 (deletion of nsp2 hypervariable region aa 726-812)] were selected for further study. pV7-nsp2Δ87 has also been shown to be replication competent in swine, producing adequate titers (Faaberg et al., 2010. In vivo growth of porcine reproductive and respiratory syndrome virus engineered nsp2 deletion mutants. Virus Res. 154, 77-85; Guo et al., 2011. Large scale parallel pyrosequencing technology: PRRSV strain VR-2332 nsp2 deletion mutant stability in swine. Virus Res. 161, 162-169).

The cDNA sequence of the nsp2 region of the pMLV strain is given in SEQ ID NO: 1 and the cDNA sequences of nsp2 region of the two deletion constructs of nsp2Δ23 and nsp2Δ87 are given in SEQ ID NO: 2 and SEQ ID NO: 4, respectively. The amino acid sequences of the two deletion constructs of nsp2Δ23 and nsp2Δ87 are given in SEQ ID NO: 3 and SEQ ID NO: 5, respectively. Three small immunogenic tags were chosen for insertion into the deletion mutants: a small epitope found on the P and V proteins of simian virus 5 (V5), the commonly used synthetic FLAG tag, and an oligopeptide derived from pancreatic ribonuclease A (S-tag) (FIG. 1A).

To generate a simplified cloning vector that lacked critical restriction enzyme recognition sites, an existing cloning vector (pCR®-XL-TOPO; ThermoFisher Scientific, Waltham, Mass., USA) was deconstructed and modified. To do so, pCR®-XL-TOPO was digested with HinfI and the two fragments (339 bp, 1043 bp) containing the origin of replication and the Zeocin resistance gene were gel purified and ligated. Subsequently, a multiple cloning site (MCS) was inserted by ligation of four annealed synthetic oligonucleotides to encode the sequence 5-CATGTACTAGTAG-GCCTAGATCTGCATGCGAATTCCGCGGATCCGGC-CGGCCGGCCG GCCCGGGCTCTAGACTCGAGAAGCTTTTAAT-TAAACCATG (SEQ ID NO: 24) into the existing PciI site. This vector was designated "pCHAZ."

To generate subclones of the targeted regions of nsp2, 2-step mutagenic PCR was carried out using Phusion polymerase (New England Biolabs, Ipswich, Mass., USA) and the pMLV infectious clone as a template. This mutagenic PCR introduced a pair of inverted EarI sites just internal to the region targeted for deletion, such that the sites excised themselves upon digestion and subsequent fill-in of the overhangs and self-ligation would generate the desired deletion. PCR products were A-tailed using GoTaq polymerase (Promega, Madison, Wis., USA) and subcloned into pGEMTeasy (Promega). All PCR subclones were verified by sequencing. These PCR subclones were subsequently transferred into pCHAZ through ligation of the SphI/SpeI fragment from pGEMTeasy into the corresponding sites of the pCHAZ MCS. The Δ23/EarI and Δ87/EarI pCHAZ subclones were then digested with EarI and filled-in using Klenow DNA polymerase (New England Biolabs). To generate the untagged deletions, cut plasmids were self-ligated. To insert an epitope tag, complimentary 5'-phosphorylated synthetic oligonucleotides encoding the desired epitope tag were annealed and ligated in place of the deleted sequence. The oligonucleotide sequences encoding the tags for V5, S-Tag, and FLAG are given in SEQ ID NO: 6, 8, and 10, respectively. The amino acid sequences of each tag V5, S-Tag, and FLAG are given in SEQ ID NO: 7, 9, and 11, respectively. Each oligonucleotide tag sequence was engineered to contain an identifying restriction enzyme recognition site (V5: XbaI; S-tag: NotI; 3xFLAG: PsiI), through translationally silent nucleotide changes. Once sequence verified, pCHAZ subclones were transferred to an intermediate clone containing nucleotides 1-4546 of the MLV genome, terminating in an FseI site, termed "MLV-Fragment I." This transfer was completed through ligation of the EcoRI/BamHI (Δ23) or HindIII/FseI (Δ87) fragments from the respective deleted or tagged-deleted pCHAZ clones into the MLV-Fragment I intermediate clone. All intermediate clones were then transferred to the full-length pMLV infectious clone, by swapping the parental SphI/FseI fragment with the corresponding respective deleted or tagged-deleted sequence. Traditional Sanger sequencing using existing PRRSV primers (available on request) was used to determine the full-length sequence of all prepared pMLV mutant cDNA clones.

Two of the resulting viruses were negative DIVAs (rMLV-nsp2Δ23 and rMLV-nsp2Δ87) and six viruses were positive DIVAs (rMLV-nsp2Δ23-V5, rMLV-nsp2Δ23-S, rMLV-nsp2Δ23-FLAG, rMLV-nsp2Δ87-V5, rMLV-nsp2Δ87-S, rMLV-nsp2Δ87-FLAG). These virus names have been abbreviated herein to Δ23, Δ87, Δ23-V5, Δ23-S, Δ23-FLAG, Δ87-V5, Δ87-S, Δ87-FLAG, respectively.

The full-length cDNA clones (10 μg) were linearized at the 3'-end by cleavage with PacI, extracted with phenol:chloroform and resuspended in 10 μl RNase-free TE (10 mM Tris-HCl, 1 mM EDTA) or water. Capped RNA transcripts were produced from 1 μg linearized DNA using the mMESSAGE MACHINE T7 Ultra kit (ThermoFisher Scientific). Transcribed RNA was then purified by phenol:chloroform extraction and resuspended in RNase-free water (40 μl). RNA was evaluated for quality on 1% native agarose gel and quantified by spectrophotometry. Transcripts (10 ng or 100 ng) derived from pMLVΔ23, pMLVΔ87, pMLVΔ23-V5, pMLVΔ23-FLAG and pMLVΔ87-V5 were initially transfected in MARC-145 cells using DMRIE-C(Han, et al., 2007. Identification of nonessential regions of the nsp2 replicase protein of porcine reproductive and respiratory syndrome virus strain VR-2332 for replication in cell culture. J. Virol. 81, 9878-9890).

MARC-145 cultured cells in Minimum Essential Medium Eagle (EMEM) medium (Sigma-Aldrich 56416c; St. Louis, Mo., USA) supplemented with 10% fetal bovine serum (bovine viral diarrhea free; Omega Scientific Inc., Tarzana, Calif., USA) and 50 μg/ml gentamicin sulfate was used to rescue and propagate recombinant viruses.

Subsequently, all RNA transcripts (1.5 and 3 μg) were electroporated in duplicate into MARC-145 cells using an established method (Ansari, et al., 2006. Influence of N-linked glycosylation of porcine reproductive and respiratory syndrome virus GP5 on virus infectivity, antigenicity, and ability to induce neutralizing antibodies. J. Virol. 80, 3994-4004). Electroporated MARC-145 cells were plated onto 60 $cm^2$ plates (passage 0) and passaged up to 2 times on 6-well plates until cytopathic effect (CPE) was seen. Recombinant virus was blindly passaged for 10 passages by inoculating 100 μl infected cell clarified supernatant diluted in 900 μl basal medium onto a monolayer of MARC-145 cells at 80% confluency in a T75 flask, rotating the infected cells 1 h at room temperature, then incubating the cells at 37° C., 5% $CO_2$ for 4-5 days. Each passage was harvested, centrifuged at 4000 rpm for 10 min, aliquoted into 2-4 ml tubes and frozen at −80° C.

Confirmation of Viral Mutants.

Figure 1B:
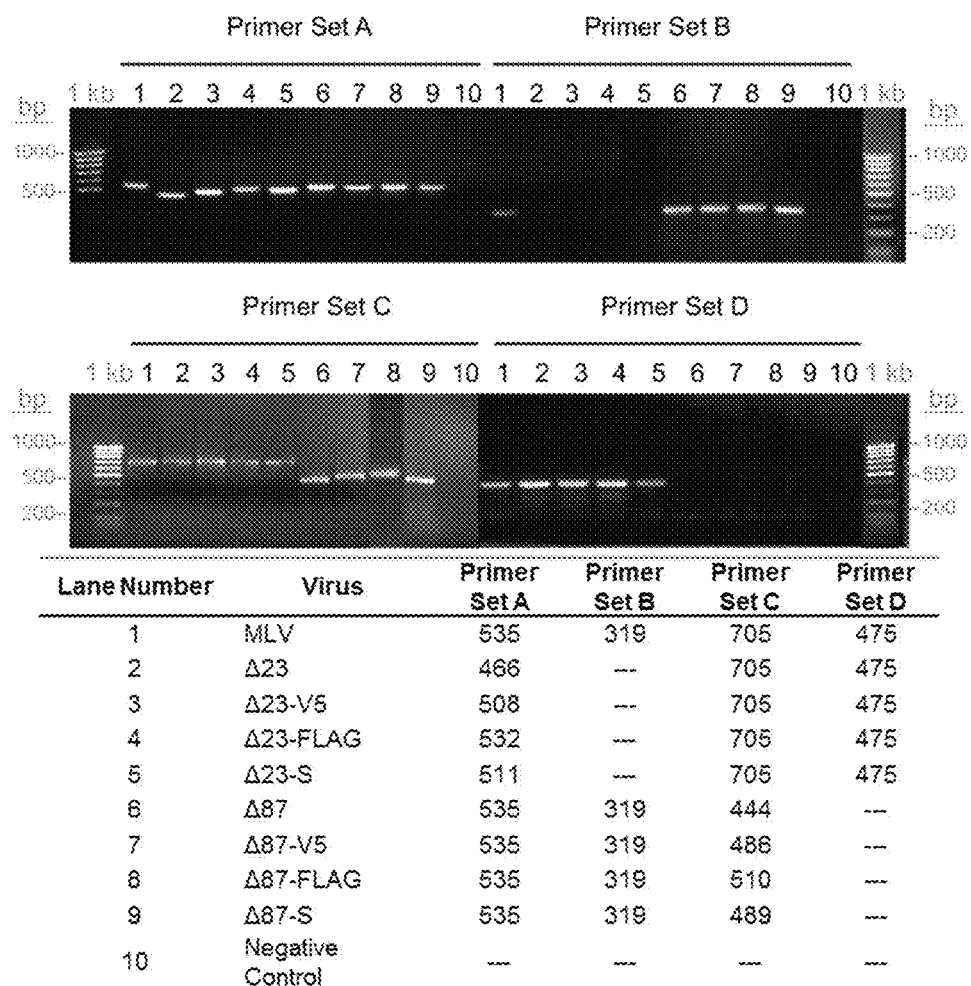
FIG. 1B shows the results of RT-PCR analysis to determine no contamination was present.

In order to provide evidence that the modified viruses were as expected, RNA was purified from each virus at passage 3 and passage 10 and fully analyzed by RT-PCR (FIGS. 1A and 1B). Viral RNA from infected cell supernatants at 3 and 10 passages (50 μl each of 9 viruses) was extracted using the MagMAX™ Total Nucleic Acid Isolation Kit with a MagMAX™ Express Particle Processor (ThermoFisher Scientific) and subjected to analysis using the One-Step RT-PCR Kit (Qiagen, Valencia, Calif.). The thermocycler settings were as follows: 1. 50° C., 30 min for 1 cycle; 2. 95° C., 15 min for 1 cycle: 3. Thirty-five cycles of 95° C. for 30 sec, 60° C. for 30 sec, 72° C. for 1 min. 4. 72° C., 10 min for 1 cycle: 5. Let sit at 4° C. until further analysis.

After passage 3, primer pairs were utilized to confirm the expected size of each product (FIG. 1B, pairs A and C) and to verify that each virus was not contaminated by other mutant viruses or parental MLV (FIG. 1B, pairs B and D). The following primer pairs were utilized with 10 μl viral RNA: A. 5'-GCGGAGGCTGCAAGTTAATGGTCTC (SEQ ID NO: 25)/5'-CGCAGGGAGTCTGAGGATTTGGATG (SEQ ID NO: 26); B. 5'-GCGGAGGCTGCAAGTTAATGGTCTC (SEQ ID NO: 27)/5'-CTTGGCCTGCCGGGTTTCACGA (SEQ ID NO: 28); C. 5'-GGGCATCTCCAAGAGGTAAAGGAAAC (SEQ ID NO: 29)/5'-GAGGCACAATAGAGTAAAAGCTGCAAAAC (SEQ ID NO: 30); D. 5'-GGGCATCTCCAAGAGGTAAAGGAAAC (SEQ ID NO: 31)/5'-CTGTGCCTGCGGACGGAGCTGATG (SEQ ID NO: 32). Primer sets A and C for passage 3 (FIG. 1A) and 10 vRNAs were utilized to ensure the correct band size for positive identification of the Δ23 and Δ87 mutants. Primer sets B and D using passage 3 vRNAs were used to show the presence (at the correct size) or the absence of MLV parent viral sequence (deletion) (FIG. 1A).

Figure 1C:
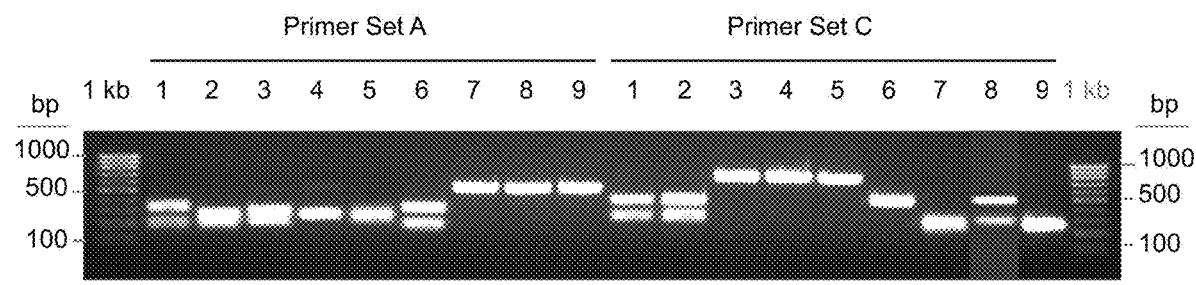
FIG. 1C shows the results of restriction enzyme analysis to determine no contamination was present.

At passage 10, in order to assess whether the mutant viruses still displayed the proper mutation with the correct inserted restriction enzyme site, restriction enzyme analysis was performed on all mutants using the products of primer sets A and C (FIG. 1C). The products were digested with appropriate restriction enzymes to provide additional verification. No evidence of contamination with other viruses was observed.

Viral Mutant Stability.

Figure 2:
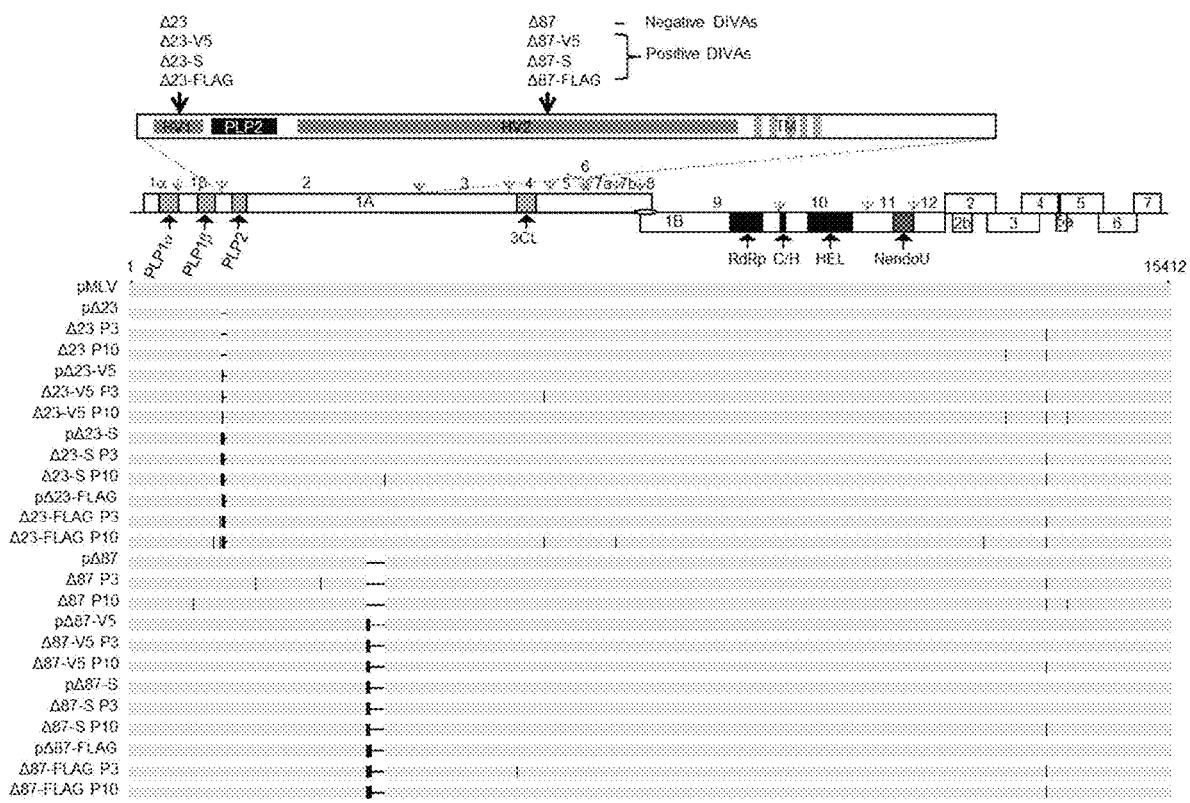
FIG. 2 shows a schematic of each DIVA vaccine as produced and after 3 and 10 passages, showing the locations of any mutations found.

To assess the influence of viral passage on sequence stability as well as to reconfirm the passages were not contaminated with other mutants, viruses at passages 3 and 10 were also processed for next generation whole viral genome sequencing using the Illumina MiSeq desktop genome sequencer (FIG. 2). Geneious version 8.1.8 was implemented to analyze the MiSeq reads in reference to the parent deletion or deletion-tagged virus, and to generate all nucleotide sequence alignments.

Overall, the modified viral genomes were stable and the mutations were few in number, except for Δ87-FLAG. All mutations but one led to amino acid changes, and all but one were single nucleotide polymorphisms (SNP). No changes were seen in the nucleotides that were modified by deletion or deletion-tagged insertion. Sixteen of the 35 mutations detected in the combined nucleotide alignment maintained the original nucleotide at a particular site, but also revealed a co-existing viral population with another nucleotide at that same site (Table 3). Only one nucleotide (ORF4 nt 13581) was shown to change consistently in most modified viruses, resulting in either a G→A, G→A/G (R) or evidence of two successive mutations A→A/T (W). Most amino acid mutations that arose over 3 to 10 passages of the modified viruses in MARC-145 cells reflected non-conservative changes. The mutation noted in ORF5 and ORF5a, seen in both Δ23 and Δ87, removed a predicted N-glycosylation motif near the N-terminal end of GP5.

TABLE 3

Mutations arising at 3 and 10 passages in each DIVA vaccine

| | | | Δ23 | | | Δ23-V5 | | | Δ23-FLAG | | | Δ23-S | | |
|---|---|---|---|---|---|---|---|---|---|---|---|---|---|---|
| Region | Nucleotide | MLV | 0 | 3 | 10 | 0 | 3 | 10 | 0 | 3 | 10 | 0 | 3 | 10 |
| Nsp1β | 953 | C | | | | | | | | | | | | |
| Nsp1β | 1254 | T | | | | | | | | | W | | | |
| Nsp2 | 1342 | G | | | | | | | | A | A | | | |
| Nsp2 | 1883 | A | | | | | | | | | | | | |

TABLE 3-continued

Mutations arising at 3 and 10 passages in each DIVA vaccine

| | | | | | | | | | | | |
|---|---|---|---|---|---|---|---|---|---|---|---|
| Nsp2 | 2837 | A | | | | | | | | | |
| Nsp2 | 3291 | G | | | | | | | | | |
| Nsp2 | 3783 | C | | | | | | | | | Y |
| Nsp4 | 5751 | C | | | | | | | | | |
| Nsp4 | 6146 | A | | | G | | | G | | | |
| Nsp7α | 7200 | C | | | | | | | | | S |
| Nsp7β | 7201 | C | | | | | | | | | Y |
| ORF2 | 12494 | A | | | | | | G | | | |
| ORF2 | 12639 | A | | | | | | G | | | |
| ORF3 | 12976 | A | | R | | R | | | | | |
| ORF4 | 13581 | G | A | A | A | A | A | A | A | A | |
| ORF4 | 13739 | T | | | | | | | | | |
| ORF5; 5a | 13885 | A | | | | | R | | | | |

| | Δ87 | | | Δ87-V5 | | | Δ87-FLAG | | | Δ87-S | | | Amino acid mutation |
|---|---|---|---|---|---|---|---|---|---|---|---|---|---|
| Region | 0 | 3 | 10 | 0 | 3 | 10 | 0 | 3 | 10 | 0 | 3 | 10 | |
| Nsp1β | | Y | | | | | | | | | | | R→R/C |
| Nsp1β | | | | | | | | | | | | | L→L/H |
| Nsp2 | | | | | | | | | | | | | G→R |
| Nsp2 | | R | | | | | | | | | | | I→I/V |
| Nsp2 | | R | | | | | | | | | | | S→S/G |
| Nsp2 | | | | | | T | | | | | | | G→V |
| Nsp2 | | | | | | | | | | | | | T→T/I |
| Nsp4 | | | | | | | | | T | | | | S→L |
| Nsp4 | | | | | | | | | | | | | K→E |
| Nsp7α | | | | | | | | | | | | | P→P/R |
| Nsp7β | | | | | | | | | | | | | |
| ORF2 | | | | | | | | | | | S | | S→S/G |
| ORF2 | | | | | | | | | | | | | Q→R |
| ORF3 | | | | | | | | | | | | | I→I/V |
| ORF4 | | W | W | | | W | | R | A | | | R | V→V//F |
| ORF4 | | | | | | Y | | | | | | | T→T |
| ORF5; 5a | | | | | R | | | | | | | | N→N/D; |
| | | | | | | | | | | | | | Q→Q/R |

Northern Blot Analyses.

Figure 3:
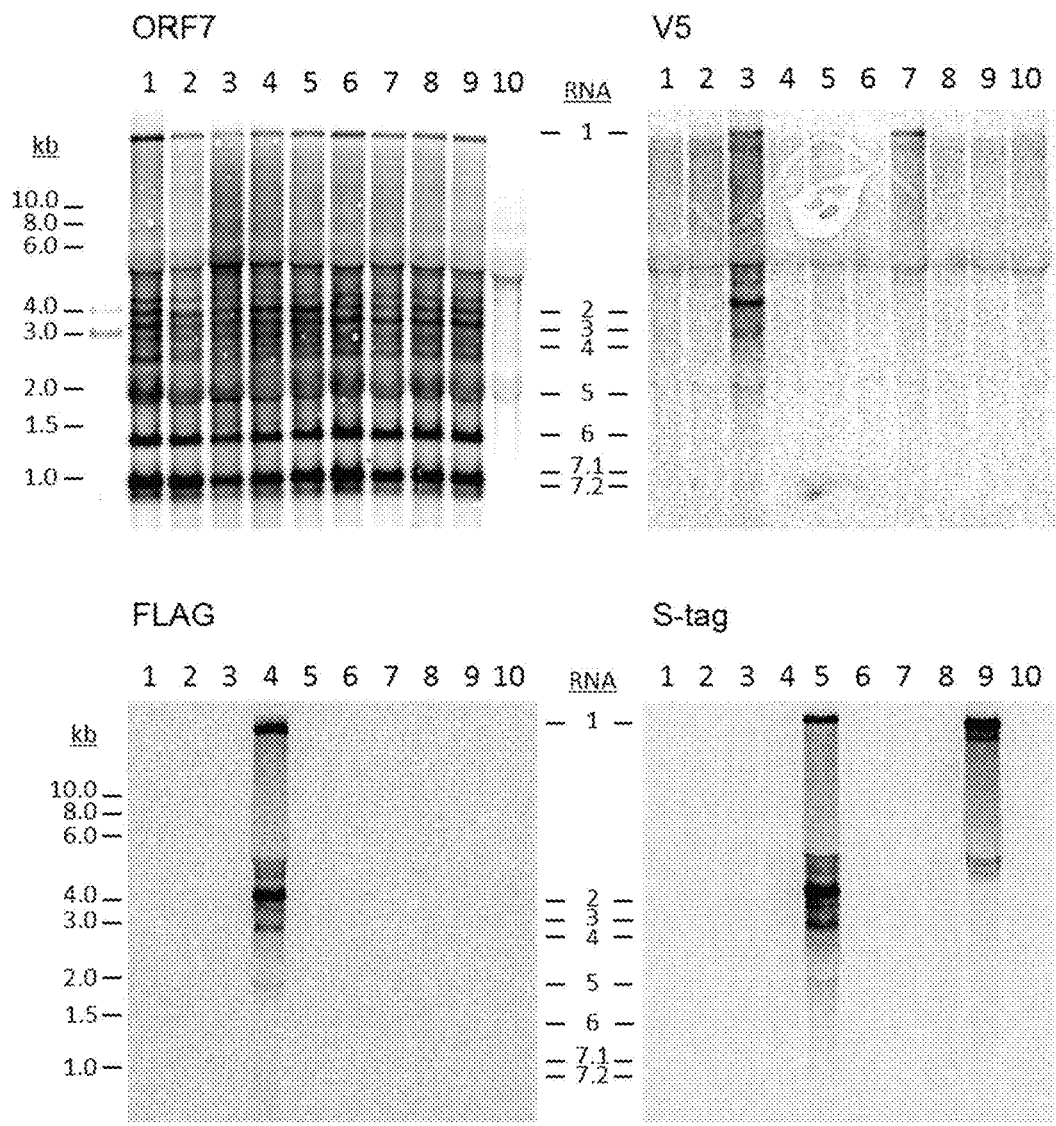
FIG. 3 shows Northern blot analysis to determine the amount and/or effect of any subgenomic RNA (sgRNA).

In PRRSV infected cells, many subgenomic RNA (sgRNA) species are detected that are produced by a discontinuous transcription strategy that proceeds through a fusion of the viral genome 5' untranslated region (UTR) to one of several sites downstream during negative strand synthesis (Kappes and Faaberg, 2015. PRRSV structure, replication and recombination: Origin of phenotype and genotype diversity. Virology 479-480, 475-486; Snijder et al., Arterivirus molecular biology and pathogenesis. J. Gen. Virol. 94, 2141-2163). These mRNAs include the standard sgRNAs (RNAs 2-7; FIG. 3—ORF7) that encode the major and minor envelope proteins (glycoproteins GP2-5, unglycosylated envelope proteins E, ORF5a protein, matrix and nucleocapsid) that utilize an antisense transcription-regulating sequence (TRS) upstream of the 5' end of the respective protein coding region with a conserved TRS sequence (UUAACC) located at the end of the 5'UTR (Snijder et al., 2013).

Northern blot analysis was performed according to the NorthernMax® Kit instructions (AM1940; ThermoFisher Scientific). MARC-145 cells were inoculated with the third passage of each virus at an MOI of 0.01. Two days after infection, intracellular RNA was extracted, denatured for 1 hour at 50° C. with glyoxal loading dye and then electrophoresed (5 μg/sample) on a glyoxal denaturing gel and transferred onto a 0.45 μm Whatman® Nytran™ SuPerCharge nylon membrane (Sigma-Aldrich) by gravity overnight at room temperature. The membrane was hybridized with a digoxin-labeled oligonucleotide probe (7-p14890: 5'-CCTTCTTTCTCTTCTGCTGCTTGCCGTTGTT-ATTTGGCAT (SEQ ID NO: 33); V5: 5'-GGTGGAATCTA-GACCCAGCAGTGGGTTGGGGATGGGCTTGCC (SEQ ID NO: 34); FLAG: 5'-CTTGTCATCGTCATCCTTG-TAGTCGATATCGTGATCCTTGTAATCGCCGTCAT-GATCC TTATAATC (SEQ ID NO: 35); S: 5'-AATCCATAT-GCTGGCGTTCGAACTTAGCGGCC (SEQ ID NO: 36)) complementary to ORF7, V5, FLAG, and S-tag respectively in ULTRAhyb® Ultrasensitive Hybridization Buffer (AM8670; ThermoFisher Scientific) at 68° C. for 16-20 h, washed two times in low stringency 2× Saline-Sodium Citrate (0.3 M sodium chloride and 30 mM trisodium citrate; SSC) with 0.1% SDS at room temperature for 10 min. The membrane was then processed for immunological detection using the DIG DNA Labeling and Detection Kit following the manufacturer's instructions (11093657910 ROCHE; Sigma-Aldrich).

With some PRRSV strains, as is the case with MLV, other atypical RNAs are detected (Wang et al., 2008; Yuan et al., 2000; Yuan et al., 2004). These unusual RNAs, termed heteroclites, have been shown to be products of aberrant fusions of viral genome 5' sequence with downstream sequence at 2-7 nucleotide stretches that are not conserved and vary between the individual nonconforming subgenomic RNAs (FIG. 3, ORF). When the intracellular RNAs are probed with the Tag antisense oligomers, the tagged Δ23 viral mutant RNAs (Fig. V5: lane 3; FLAG: lane 4; S-tag: lane 5) are detected in full-length transcripts as well as some of these heteroclite RNA species. However, only the full-length RNA is predominantly detected when the probes react with the tagged Δ87 mutant intracellular RNA (FIG. 3, V5: lane 7; FLAG: lane 8; S-tag: lane 9). The instability of Δ87-FLAG in this experiment resulted in the lack of hybridization to the negative FLAG oligonucleotide probe.

Multi-Step Growth Curve.

Using passage 3 stocks, the deletion and deletion-tagged viruses were analyzed for viral replication rate. Growth curves were performed simultaneously (0.1 MOI input) with sampling at 0, 6, 12, 24, 36, 48 and 72 h, using known techniques (Han et al., 2007. Identification of nonessential regions of the nsp2 replicase protein of porcine reproductive and respiratory syndrome virus strain VR-2332 for replication in cell culture. J. Virol. 81, 9878-9890; Wang et al., 2008). Virus titers of recombinant MLV, Δ23, Δ87, Δ23-V5, Δ87-V5, Δ23-S, Δ87-S, Δ23-FLAG and Δ87-FLAG at each time point were determined by plaque assay on MARC-145 cells. Titers (plaque forming units (PFU)/ml) were determined on MARC-145 cells to assess in vitro growth properties.

Figure 4A:
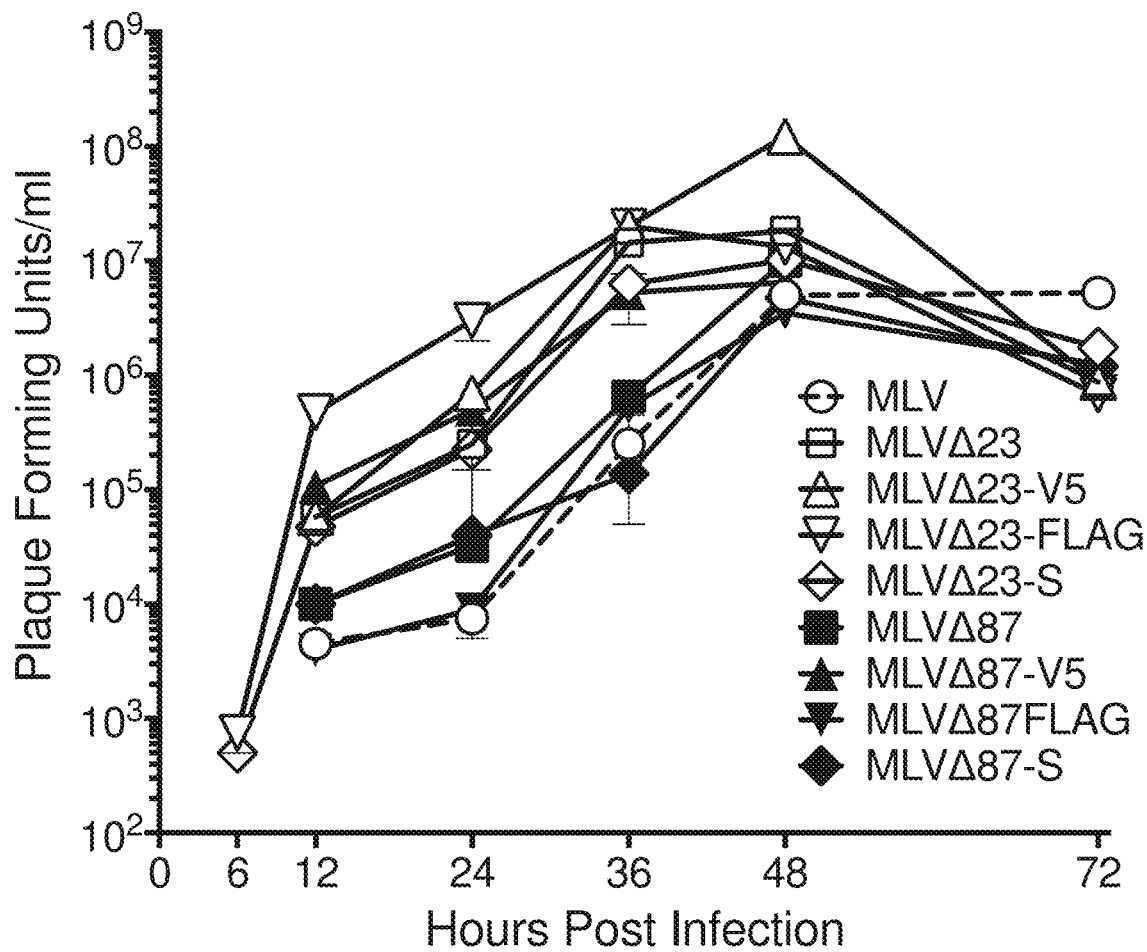
FIG. 4A shows data for the growth rate of some DIVA vaccines.
Figure 4B:
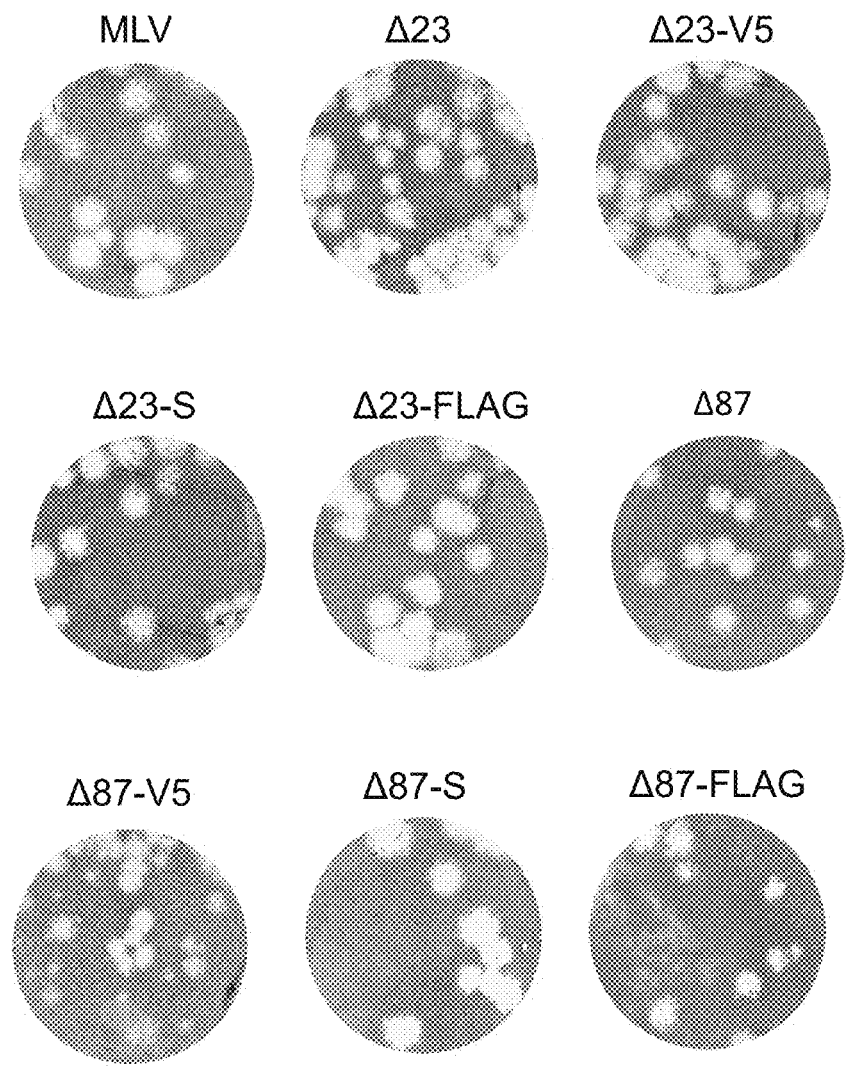
FIG. 4B shows images of plaque growth at a third passage for some DIVA vaccines.

A range of replication rates was observed. Δ23, Δ23-V5, Δ23-S, Δ23-FLAG and Δ87-V5 viruses replicated to titers that were 0.8-1.5 logs higher than MLV on MARC-145 cells, while Δ87, Δ87-S, Δ87-FLAG viruses replicated at rates similar to the vaccine strain MLV (FIG. 4A). This was also evidenced by the plaque assay, which showed that all mutants gave similar or slightly larger plaques sizes than the parent MLV (FIG. 4B).

Immunofluorescence.

Each tagged mutant was assessed by immunofluorescence with either an antibody to PRRSV nucleocapsid (SDOW17) or by an antibody to one of the three different tags. Uninfected or infected MARC-145 cells grown on chamber slides were fixed with paraformaldehyde, permeabilized with 0.2% Triton X-100 in phosphate buffered saline (PBS), and treated with 0.1% sodium borohydride PBS. Primary antibodies used were mAb SDOW-17 (1:50; RTI, Brookings, S. Dak., USA) specific for the PRRSV nucleocapsid protein, mAb to the V5-tag (1:500; Abcam, Cambridge, Mass., USA), mAb to the FLAG tag (1:500; Sigma-Aldrich, St. Louis, Mo.) and mAb to the S tag (1:100; Abcam). The secondary antibody used was fluorescein isothiocyanate (FITC)-conjugated affinity isolated goat anti-mouse IgG (Fc specific; Sigma-Aldrich). DAPI (4',6-diamidino-2-phenylindole) was used to stain nuclei (Thermo-Scientific). Stained slides were visualized using 40× and 60× oil immersion objectives on a Nikon A1R+ laser scanning confocal microscope.

Figure 4C:
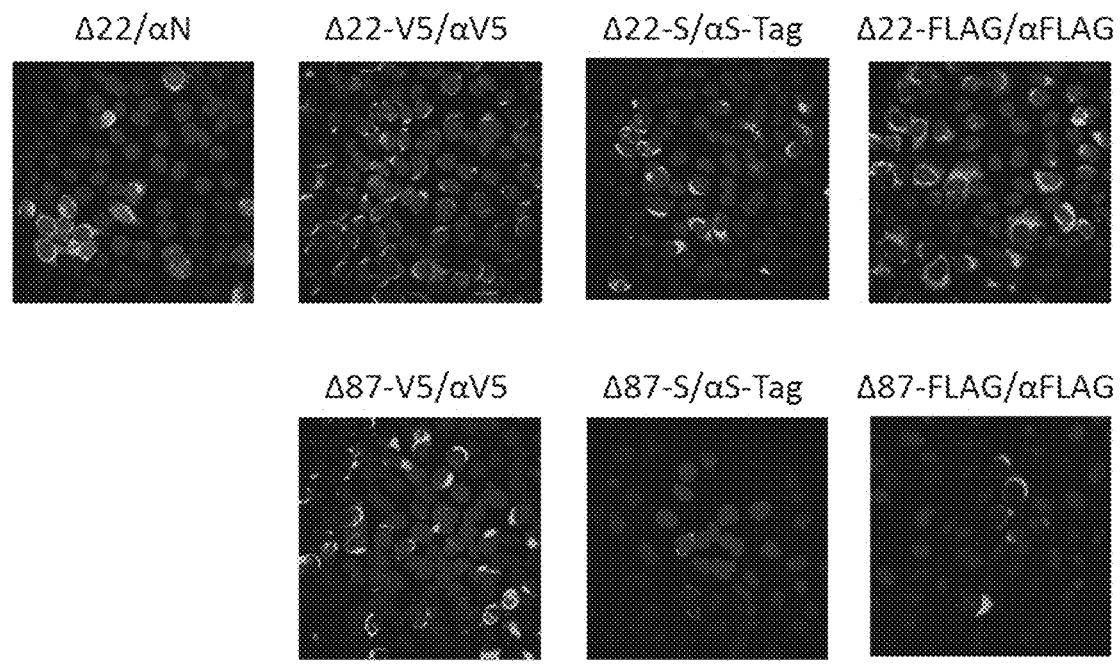
FIG. 4C shows an immunofluorescence assay in MARC-145 cells to determine localization, if any, of some DIVA vaccines in a cellular system.
Figure 4D:
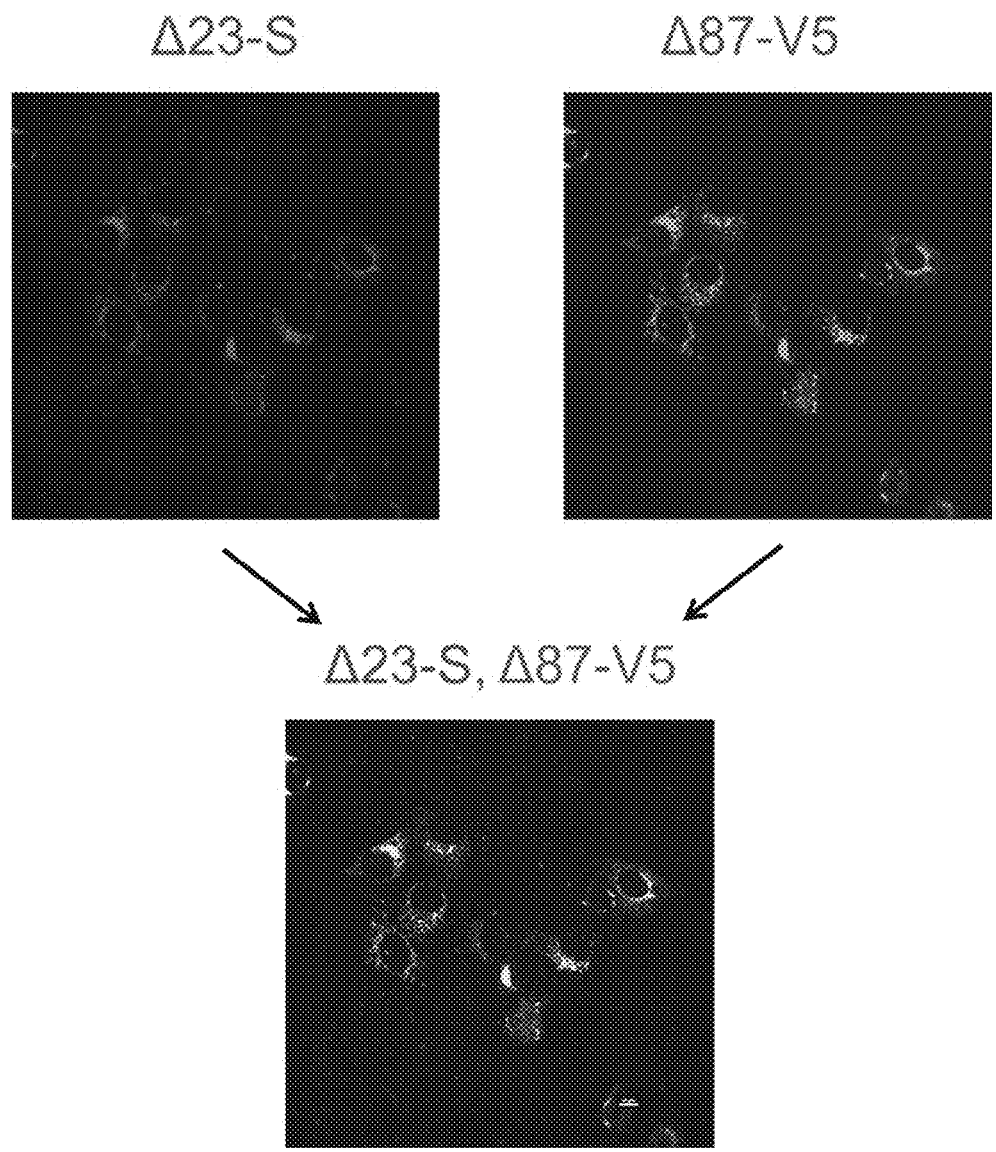
FIG. 4D shows an immunofluorescence assay in MARC-145 cells with a co-infection of Δ23-S and Δ87-V5 tagged DIVAs, revealing some differentiation in non-perinuclear localization.

All viral mutants showed reactivity to the nucleocapsid antibody, as shown with untagged deletion mutant Δ23 (FIG. 4C). Each viral mutant detected with its respective antibody showed similar perinuclear fluorescence. In addition, Δ23-V5, Δ23-S, and Δ23-FLAG were shown to distribute into a diffuse punctate pattern, characteristic of endoplasmic reticulum (ER)/Golgi compartments, similar to results generated previously with an α-nsp2-OTU antibody (Kappes et al., 2013. Highly divergent strains of porcine reproductive and respiratory syndrome virus incorporate multiple isoforms of nonstructural protein 2 into virions. J. Virol. 87, 13456-13465). Since the small immunogenic tags were placed within the recognized OTU domain (nsp2 aa 1-215), these results are both consistent and suggest that modification of the N-terminal region does not interfere with viral protein processing or cellular localization. Detection of Δ87-V5, Δ87-S, and Δ87-FLAG by their respective antibodies showed that the hypervariable region of nsp2 was more localized to regions directly adjacent to the infected cell nuclei, although a minor amount of nsp2 was also detected in the ER/Golgi region (FIG. 4C). No cross reactivity between the deletion and deletion-tagged viruses was detected when stained with a tag antibody different from the antibody to the engineered tag of each genetically altered virus, showing that these separate viruses could potentially be co-infected without loss of specificity (data not shown). Co-infection of MARC-145 cells with Δ23-S and Δ87-V5 tagged DIVAs revealed some differentiation in non-perinuclear localization via an immunofluorescence assay (FIG. 4D).

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An immunogenic composition, comprising:
   an isolated polynucleotide sequence representing a modified live vaccine for porcine reproductive and respiratory syndrome virus having an nsp2 region; and
   a pharmaceutically acceptable adjuvant,
   wherein the amino acid sequence of the nsp2 region is one of a sequence of SEQ ID NO: 3; a sequence of SEQ ID NO: 13; a sequence of SEQ ID NO: 15; a sequence of SEQ ID NO: 17; a sequence having at least 99% homology to SEQ ID NO: 13; a sequence having at least 99% homology to SEQ ID NO: 15; and a sequence having at least 99% homology to SEQ ID NO: 17, and
   wherein the immunogenic composition is capable of inducing an immune response in a recipient.

2. The immunogenic composition of claim 1, further comprising a pharmaceutically acceptable carrier.

3. An immunogenic composition, comprising:
   an isolated polynucleotide sequence representing a modified live vaccine for porcine reproductive and respiratory syndrome virus having an nsp2 region; and
   a pharmaceutically acceptable adjuvant,
   wherein the amino acid sequence of the nsp2 is one of a sequence of SEQ ID NO: 5; a sequence of SEQ ID NO: 19; a sequence of SEQ ID NO: 21; a sequence of SEQ ID NO: 23; a sequence having at least 99% homology to SEQ ID NO: 19; a sequence having at least 99% homology to SEQ ID NO: 21; and a sequence having at least 99% homology to SEQ ID NO: 23, and
   wherein the immunogenic composition is capable of inducing an immune response in a recipient.

4. The immunogenic composition of claim 3, further comprising a pharmaceutically acceptable carrier.

5. A method for reducing the incidence of porcine reproductive and respiratory syndrome virus (PRRSV) in swine, comprising administering to a swine an immunogenic composition in an amount effective to generate an immune response in said swine to said PRRSV,
   wherein the immunogenic composition comprises an isolated polynucleotide sequence representing a modified live vaccine for porcine reproductive and respiratory syndrome virus having an nsp2 region,
   wherein the amino acid sequence of the nsp2 region is one of a sequence of SEQ ID NO: 3; a sequence of SEQ ID NO: 13; a sequence of SEQ ID NO: 15; a sequence of SEQ ID NO: 17; a sequence having at least 99% homology to SEQ ID NO: 13; a sequence having at least 99% homology to SEQ ID NO: 15; a sequence having at least 99% homology to SEQ ID NO: 17; a sequence of SEQ ID NO: 5; a sequence of SEQ ID NO:

19; a sequence of SEQ ID NO: 21; a sequence of SEQ ID NO: 23; a sequence having at least 99% homology to SEQ ID NO: 19; a sequence having at least 99% homology to SEQ ID NO: 21; and a sequence having at least 99% homology to SEQ ID NO: 23.

6. The method for reducing the incidence of PRRSV in swine of claim 5, wherein the immune response is protection against porcine reproductive and respiratory syndrome virus.

\* \* \* \* \*

SEQUENCE LISTING

```
<160> NUMBER OF SEQ ID NOS: 36

<210> SEQ ID NO 1
<211> LENGTH: 3588
<212> TYPE: DNA
<213> ORGANISM: Porcine reproductive and respiratory syndrome virus

<400> SEQUENCE: 1
gctggaaaga gagcaagaaa agcacgctct tgtgcgactg ctacagtcgc tggccgcgct      60
ttgtccgttc gtgaaacccg gcaggccaag gagcacgagg ttgccggcgc caacaaggct     120
gagcacctca aacactactc cccgcctgcc gaagggaatt gtggttggca ctgcatttcc     180
gccatcgcca accggatggt gaattccaaa tttgaaacca cccttcccga aagagtgaga     240
cctccagatg actgggctac tgacgaggat cttgtgaatg ccatccaaat cctcagactc     300
cctgcggcct tagacaggaa cggtgcttgt actagcgcca agtacgtact taagctggaa     360
```

```
ggtgagcatt ggactgtcac tgtgacccct gggatgtccc cttctttgct ccctcttgaa    420
tgtgttcagg gctgttgtgg gcacaagggc ggtcttggtt ccccagatgc agtcgaggtc    480
tccggatttg accctgcctg ccttgaccgg ctggctgagg tgatgcacct gcctagcagt    540
gctatcccag ccgctctggc cgaaatgtct ggcgattccg atcgttcggc ttctccggtc    600
accaccgtgt ggactgtttc gcagttcttt gcccgtcaca gcggagggaa tcaccctgac    660
caagtgcgct tagggaaaat tatcagcctt tgtcaggtga ttgaggactg ctgctgttcc    720
cagaacaaaa ccaaccgggt caccccggag gaggtcgcag caaagattga cctgtacctc    780
cgtggtgcaa caaatcttga agaatgcttg gccaggcttg agaaagcgcg cccgccacgc    840
gtaatcgaca ccttctttga ttgggatgtt gtgctccctg gggttgaggc ggcaacccag    900
acgatcaagc tgccccaggt caaccagtgt cgtgctctgg tccctgttgt gactcaaaag    960
tccttggaca acaactcggt cccctgacc gccttttcac tggctaacta ctactaccgt   1020
gcgcaaggtg acgaagttcg tcaccgtgaa agactaaccg ccgtgctctc caagttggaa   1080
aaggttgttc gagaagaata tgggctcatg ccaaccgagc ctggtccacg cccacactg   1140
ccacgcgggc tcgacgaact caaagaccag atggaggagg acttgctgaa actggctaac   1200
gcccagacga cttcggacat gatggcctgg gcagtcgagc aggttgaccT aaaaacttgg   1260
gtcaagaact acccgcggtg gacaccacca cccctccgc caaaagttca gcctcgaaaa   1320
acgaagcctg tcaagagctt gccggagaga agcctgtcc ccgccccgcg caggaaggtt   1380
gggtccgatt gtggcagccc ggtttcatta ggcggcgatg tccctaacag ttgggaagat   1440
ttggctgtta gtagccccTt tgatctcccg accccacctg agccggcaac accttcaagt   1500
gagctggtga ttgtgtcctc accgcaatgc atcttcaggc cggcgacacc cttgagtgag   1560
ccggctccaa ttcccgcacc tcgcggaact gtgtctcgac cggtgacacc cttgagtgag   1620
ccgatccctg tgcccgcacc gcggcgtaag tttcagcagg tgaaaagatt gagttcggcg   1680
gcggcaatcc caccgtacca gaacgagccc ctggatttgt ctgcttcctc acagactgaa   1740
tatgaggcct ctcccccagc accgccgcag agcgggggcg ttctgggagt agaggggcat   1800
gaagctgagg aaaccctgag tgaaatctcg acatgtcgg gtaacattaa acctgcgtcc   1860
gtgtcatcaa gcagctcctt gtccagcgtg agaatcacac gcccaaaata ctcagctcaa   1920
gccatcatcg actcgggcgg gccctgcagt gggcatctcc aagaggtaaa ggaaacatgc   1980
cttagtgtca tgcgcgaggc atgtgatgcg actaagcttg atgaccctgc tacgcaggaa   2040
tggctttctc gcatgtggga tcgggtggac atgctgactt ggcgcaacac gtctgtttac   2100
caggcgattt gcaccttaga tggcaggtta agttcctcc caaaaatgat actcgagaca   2160
ccgccgccct atccgtgtga gtttgtgatg atgcctcaca cgcctgcacc ttccgtaggt   2220
gcggagagcg accttaccat ggctcagtt gctactgaag atgttccacg catcctcgag   2280
aaaatagaaa atgtcggcga gatggccaac cagggaccct tggccttctc cgaggataaa   2340
ccggtagatg accaacttgt caacgacccc cggatatcgt cgcggaggcc tgacgagagc   2400
acatcagctc cgtccgcagg cacaggtggc gccggctctt ttaccgattt gccgccttca   2460
gatggcgcga tgcggacgg ggggggccg tttcggacgg taaaaagaaa agctgaaagg   2520
ctctttgacc aactgagccg tcaggttttt gacctcgtct cccatctccc tgttttcttc   2580
tcacgccttt tctaccctgg cggtggttat tctccgggtg attggggttt tgcagctttt   2640
actctattgt gcctctttt atgttacagt taccagcctt ttggtattgc tcccctcttg   2700
ggtgtgtttt ctgggtcttc tcggcgcgtt cgaatggggg tttttggctg ctggttggct   2760
```

```
tttgctgttg gtctgttcaa gcctgtgtcc gacccagtcg gcgctgcttg tgagtttgac      2820
tcgccagagt gtagaaacat ccttcattct tttgagcttc tcaaaccttg ggaccctgtt      2880
cgcagccttg ttgtgggccc cgtcggtctc ggtcttgcca ttcttggcag gttactgggc      2940
ggggcacgct gcatctggca ctttttgctt aggcttggca ttgttgcaga ctgtatcttg      3000
gctggagctt acgtgctttc tcaaggtagg tgtaaaaagt gctggggatc ttgtataaga      3060
actgctccta tgaggtcgc ttttaacgtg tttcctttca cacgtgcgac caggtcgtca      3120
cttatcgacc tgtgcgatcg gttttgtgcg ccaaaaggaa tggaccccat ttttctcgcc      3180
actgggtggc gcgggtgctg ggccggccga agcccccattg agcaaccctc tgaaaaaccc      3240
atcgcgtttg cccaattgga tgaaaagaag attacggcta ggactgtggt cgcccagcct      3300
tatgacccca accaagccgt aaagtgcttg cgggtattgc aggcgggtgg ggcgatggtg      3360
gctaaggcgg tcccaaaagt ggtcaaggtt ccgctgttc cattccgagc cccttctttt      3420
cccactggag tgaaagttga ccctgattgc agggtcgtgg ttgaccctga cactttcact      3480
gcagctctcc ggtctggcta ctccaccaca aacctcgtcc ttggtgtagg gactttgcc      3540 cagctgaatg gattaaaaat caggcaaatt ccaagcctt caggggga                    3588
```

<210> SEQ ID NO 2
<211> LENGTH: 3519
<212> TYPE: DNA
<213> ORGANISM: Porcine reproductive and respiratory syndrome virus

<400> SEQUENCE: 2

```
gctggaaaga gagcaagaaa agcacgctct tgtgccggcg ccaacaaggc tgagcacctc        60
aaacactact ccccgcctgc cgaagggaat tgtggttggc actgcatttc cgccatcgcc       120
aaccggatgg tgaattccaa atttgaaacc acccttcccg aaagagtgag acctccagat       180
gactgggcta ctgacgagga tcttgtgaat gccatccaaa tcctcagact ccctgcggcc       240
ttagacagga acggtgcttg tactagcgcc aagtacgtac ttaagctgga aggtgagcat       300
tggactgtca ctgtgacccc tgggatgtcc ccttctttgc tccctcttga atgtgttcag       360
ggctgttgtg ggcacaaggg cggtcttggt tccccagatg cagtcgaggt ctccggattt       420
gaccctgcct gccttgaccg gctggctgag gtgatgcacc tgcctagcag tgctatccca       480
gccgctctgg ccgaaatgtc tggcgattcc gatcgttcgg cttctccggt caccaccgtg       540
tggactgttt cgcagttctt gcccgtcac agcggaggga atcaccctga ccaagtgcgc       600
ttagggaaaa ttatcagcct ttgtcaggtg attgaggact gctgctgttc cagaacaaa       660 accaaccggg tcaccccgga ggaggtcgca gcaaagattg acctgtacct ccgtggtgca       720
acaaatcttg aagaatgctt ggccaggctt gagaaagcgc gcccgccacg cgtaatcgac       780
accttctttg attgggatgt tgtgctccct ggggttgagg cggcaaccca gacgatcaag       840
ctgccccagg tcaaccagtg tcgtgctctg gtccctgttg tgactcaaaa gtccttggac       900
aacaactcgg tccccctgac cgccttttca ctggctaact actactaccg tgcgcaaggt       960
gacgaagttc gtcaccgtga aagactaacc gccgtgctct ccaagttgga aaaggttgtt      1020
cgagaagaat atgggctcat gccaaccgag cctggtccac ggcccacact gccacgcggg      1080
ctcgacgaac tcaaagacca gatggaggag gacttgctga aactggctaa cgcccagacg      1140
acttcggaca tgatggcctg gcagtcgag cagtgaggcc tacttgatccg gtcagcc        1200 tacccgcggt ggacaccacc accccctccg ccaaaagttc agcctcgaaa aacgaagcct      1260
```

```
gtcaagagct tgccggagag aaagcctgtc cccgccccgc gcaggaaggt tgggtccgat    1320
tgtggcagcc cggtttcatt aggcggcgat gtccctaaca gttgggaaga tttggctgtt    1380
agtagcccct ttgatctccc gaccccacct gagccggcaa caccttcaag tgagctggtg    1440
attgtgtcct caccgcaatg catcttcagg ccggcgacac ccttgagtga gccggctcca    1500
attcccgcac ctcgcggaac tgtgtctcga ccggtgacac ccttgagtga gccgatccct    1560
gtgcccgcac cgcggcgtaa gtttcagcag gtgaaaagat tgagttcggc ggcggcaatc    1620
ccaccgtacc agaacgagcc cctggatttg tctgcttcct cacagactga atatgaggcc    1680
tctcccccag caccgccgca gagcgggggc gttctgggag tagaggggca tgaagctgag    1740
gaaaccctga gtgaaatctc ggacatgtcg ggtaacatta aacctgcgtc cgtgtcatca    1800
agcagctcct tgtccagcgt gagaatcaca cgcccaaaat actcagctca agccatcatc    1860
gactcgggcg ggccctgcag tgggcatctc caagaggtaa aggaaacatg ccttagtgtc    1920
atgcgcgagg catgtgatgc gactaagctt gatgaccctg ctacgcagga atggctttct    1980
cgcatgtggg atcgggtgga catgctgact ggcgcaaca cgtctgttta ccaggcgatt    2040
tgcaccttag atggcaggtt aaagttcctc ccaaaaatga tactcgagac accgccgccc    2100
tatccgtgtg agtttgtgat gatgcctcac acgcctgcac cttccgtagg tgcggagagc    2160
gaccttacca ttggctcagt tgctactgaa gatgttccac gcatcctcga gaaaatagaa    2220
aatgtcggcg agatggccaa ccagggaccc ttggccttct ccgaggataa accggtagat    2280
gaccaacttg tcaacgaccc ccggatatcg tcgcggaggc ctgacgagag cacatcagct    2340
ccgtccgcag gcacaggtgg cgccggctct tttaccgatt tgccgccttc agatggcgcg    2400
gatgcggacg ggggggggcc gtttcggacg gtaaaaagaa aagctgaaag gctctttgac    2460
caactgagcc gtcaggtttt tgacctcgtc tcccatctcc ctgttttctt ctcacgcctt    2520
ttctaccctg gcggtggtta ttctccgggt gattggggtt ttgcagcttt tactctattg    2580
tgcctctttt tatgttacag ttacccagcc tttggtattg ctcccctctt gggtgtgttt    2640
tctgggtctt ctcggcgcgt tcgaatgggg gttttttggct gctggttggc ttttgctgtt    2700
ggtctgttca gcctgtgtc cgacccagtc ggcgctgctt gtgagtttga ctcgccagag    2760
tgtagaaaca tccttcattc ttttgagctt ctcaaacctt gggaccctgt tcgcagcctt    2820
gttgtgggcc ccgtcggtct cggtcttgcc attcttggca ggttactggg cggggcacgc    2880
tgcatctggc acttttttgct taggcttggc attgttgcag actgtatctt ggctggagct    2940
tacgtgcttt tcaaggtag gtgtaaaaag tgctggggat cttgtataag aactgctcct    3000
aatgaggtcg cttttaacgt gtttcctttc acacgtgcga ccaggtcgtc acttatcgac    3060
ctgtgcgatc ggttttgtgc gccaaaagga atggacccca ttttctcgc cactgggtgg    3120
cgcgggtgct gggccggccg aagccccatt gagcaaccct ctgaaaaacc catcgcgttt    3180
gcccaattgg atgaaaagaa gattacggct aggactgtgg tcgcccagcc ttatgacccc    3240
aaccaagccg taaagtgctt gcgggtattg caggcgggtg gggcgatggt ggctaaggcg    3300
gtcccaaaag tggtcaaggt ttccgctgtt ccattccgag ccccttcct tcccactgga    3360
gtgaaagttg accctgattg cagggtcgtg gttgaccctg acactttcac tgcagctctc    3420
cggtctggct actccaccac aaacctcgtc cttggtgtag gggactttgc ccagctgaat    3480
ggattaaaaa tcaggcaaat ttccaagcct tcagggga                           3519
```

<210> SEQ ID NO 3  
<211> LENGTH: 1173

<212> TYPE: PRT
<213> ORGANISM: Porcine reproductive and respiratory syndrome virus

<400> SEQUENCE: 3

Ala Gly Lys Arg Ala Arg Lys Ala Arg Ser Cys Ala Gly Ala Asn Lys
1               5                   10                  15

Ala Glu His Leu Lys His Tyr Ser Pro Pro Ala Glu Gly Asn Cys Gly
            20                  25                  30

Trp His Cys Ile Ser Ala Ile Ala Asn Arg Met Val Asn Ser Lys Phe
        35                  40                  45

Glu Thr Thr Leu Pro Glu Arg Val Arg Pro Pro Asp Asp Trp Ala Thr
    50                  55                  60

Asp Glu Asp Leu Val Asn Ala Ile Gln Ile Leu Arg Leu Pro Ala Ala
65                  70                  75                  80

Leu Asp Arg Asn Gly Ala Cys Thr Ser Ala Lys Tyr Val Leu Lys Leu
                85                  90                  95

Glu Gly Glu His Trp Thr Val Thr Val Thr Pro Gly Met Ser Pro Ser
            100                 105                 110

Leu Leu Pro Leu Glu Cys Val Gln Gly Cys Cys Gly His Lys Gly Gly
        115                 120                 125

Leu Gly Ser Pro Asp Ala Val Glu Val Ser Gly Phe Asp Pro Ala Cys
    130                 135                 140

Leu Asp Arg Leu Ala Glu Val Met His Leu Pro Ser Ser Ala Ile Pro
145                 150                 155                 160

Ala Ala Leu Ala Glu Met Ser Gly Asp Ser Asp Arg Ser Ala Ser Pro
                165                 170                 175

Val Thr Thr Val Trp Thr Val Ser Gln Phe Phe Ala Arg His Ser Gly
            180                 185                 190

Gly Asn His Pro Asp Gln Val Arg Leu Gly Lys Ile Ile Ser Leu Cys
        195                 200                 205

Gln Val Ile Glu Asp Cys Cys Cys Ser Gln Asn Lys Thr Asn Arg Val
    210                 215                 220

Thr Pro Glu Glu Val Ala Ala Lys Ile Asp Leu Tyr Leu Arg Gly Ala
225                 230                 235                 240

Thr Asn Leu Glu Glu Cys Leu Ala Arg Leu Glu Lys Ala Arg Pro Pro
                245                 250                 255

Arg Val Ile Asp Thr Phe Phe Asp Trp Asp Val Val Leu Pro Gly Val
            260                 265                 270

Glu Ala Ala Thr Gln Thr Ile Lys Leu Pro Gln Val Asn Gln Cys Arg
        275                 280                 285

Ala Leu Val Pro Val Val Thr Gln Lys Ser Leu Asp Asn Asn Ser Val
    290                 295                 300

Pro Leu Thr Ala Phe Ser Leu Ala Asn Tyr Tyr Arg Ala Gln Gly
305                 310                 315                 320

Asp Glu Val Arg His Arg Glu Arg Leu Thr Ala Val Leu Ser Lys Leu
                325                 330                 335

Glu Lys Val Val Arg Glu Glu Tyr Gly Leu Met Pro Thr Glu Pro Gly
            340                 345                 350

Pro Arg Pro Thr Leu Pro Arg Gly Leu Asp Glu Leu Lys Asp Gln Met
        355                 360                 365

Glu Glu Asp Leu Leu Lys Leu Ala Asn Ala Gln Thr Thr Ser Asp Met
    370                 375                 380

Met Ala Trp Ala Val Glu Gln Val Asp Leu Lys Thr Trp Val Lys Asn
385                 390                 395                 400

```
Tyr Pro Arg Trp Thr Pro Pro Pro Pro Lys Val Gln Pro Arg
                405             410             415

Lys Thr Lys Pro Val Lys Ser Leu Pro Glu Arg Lys Pro Val Pro Ala
                420             425             430

Pro Arg Arg Lys Val Gly Ser Asp Cys Gly Ser Pro Val Ser Leu Gly
            435                 440             445

Gly Asp Val Pro Asn Ser Trp Glu Asp Leu Ala Val Ser Ser Pro Phe
        450                 455             460

Asp Leu Pro Thr Pro Pro Glu Pro Ala Thr Pro Ser Ser Glu Leu Val
465             470              475             480

Ile Val Ser Ser Pro Gln Cys Ile Phe Arg Pro Ala Thr Pro Leu Ser
                485             490             495

Glu Pro Ala Pro Ile Pro Ala Pro Arg Gly Thr Val Ser Arg Pro Val
                500             505             510

Thr Pro Leu Ser Glu Pro Ile Pro Val Pro Ala Pro Arg Arg Lys Phe
            515             520             525

Gln Gln Val Lys Arg Leu Ser Ser Ala Ala Ala Ile Pro Pro Tyr Gln
        530             535             540

Asn Glu Pro Leu Asp Leu Ser Ala Ser Ser Gln Thr Glu Tyr Glu Ala
545             550             555             560

Ser Pro Pro Ala Pro Pro Gln Ser Gly Gly Val Leu Gly Val Glu Gly
                565             570             575

His Glu Ala Glu Glu Thr Leu Ser Glu Ile Ser Asp Met Ser Gly Asn
                580             585             590

Ile Lys Pro Ala Ser Val Ser Ser Ser Ser Leu Ser Ser Val Arg
            595             600             605

Ile Thr Arg Pro Lys Tyr Ser Ala Gln Ala Ile Ile Asp Ser Gly Gly
        610             615             620

Pro Cys Ser Gly His Leu Gln Glu Val Lys Glu Thr Cys Leu Ser Val
625             630             635             640

Met Arg Glu Ala Cys Asp Ala Thr Lys Leu Asp Asp Pro Ala Thr Gln
                645             650             655

Glu Trp Leu Ser Arg Met Trp Asp Arg Val Asp Met Leu Thr Trp Arg
                660             665             670

Asn Thr Ser Val Tyr Gln Ala Ile Cys Thr Leu Asp Gly Arg Leu Lys
            675             680             685

Phe Leu Pro Lys Met Ile Leu Glu Thr Pro Pro Tyr Pro Cys Glu
        690             695             700

Phe Val Met Met Pro His Thr Pro Ala Pro Ser Val Gly Ala Glu Ser
705             710             715             720

Asp Leu Thr Ile Gly Ser Val Ala Thr Glu Asp Val Pro Arg Ile Leu
                725             730             735

Glu Lys Ile Glu Asn Val Gly Glu Met Ala Asn Gln Gly Pro Leu Ala
                740             745             750

Phe Ser Glu Asp Lys Pro Val Asp Gln Leu Val Asn Asp Pro Arg
            755             760             765

Ile Ser Ser Arg Arg Pro Asp Glu Ser Thr Ser Ala Pro Ser Ala Gly
        770             775             780

Thr Gly Gly Ala Gly Ser Phe Thr Asp Leu Pro Pro Ser Asp Gly Ala
785             790             795             800

Asp Ala Asp Gly Gly Pro Phe Arg Thr Val Lys Arg Lys Ala Glu
                805             810             815
```

```
Arg Leu Phe Asp Gln Leu Ser Arg Gln Val Phe Asp Leu Val Ser His
                820                 825                 830
Leu Pro Val Phe Phe Ser Arg Leu Phe Tyr Pro Gly Gly Gly Tyr Ser
            835                 840                 845
Pro Gly Asp Trp Gly Phe Ala Ala Phe Thr Leu Leu Cys Leu Phe Leu
850                 855                 860
Cys Tyr Ser Tyr Pro Ala Phe Gly Ile Ala Pro Leu Leu Gly Val Phe
865                 870                 875                 880
Ser Gly Ser Ser Arg Arg Val Arg Met Gly Val Phe Gly Cys Trp Leu
                885                 890                 895
Ala Phe Ala Val Gly Leu Phe Lys Pro Val Ser Asp Pro Val Gly Ala
            900                 905                 910
Ala Cys Glu Phe Asp Ser Pro Glu Cys Arg Asn Ile Leu His Ser Phe
        915                 920                 925
Glu Leu Leu Lys Pro Trp Asp Pro Val Arg Ser Leu Val Val Gly Pro
930                 935                 940
Val Gly Leu Gly Leu Ala Ile Leu Gly Arg Leu Leu Gly Gly Ala Arg
945                 950                 955                 960
Cys Ile Trp His Phe Leu Leu Arg Leu Gly Ile Val Ala Asp Cys Ile
                965                 970                 975
Leu Ala Gly Ala Tyr Val Leu Ser Gln Gly Arg Cys Lys Lys Cys Trp
            980                 985                 990
Gly Ser Cys Ile Arg Thr Ala Pro Asn Glu Val Ala Phe Asn Val Phe
        995                 1000                1005
Pro Phe Thr Arg Ala Thr Arg Ser Ser Leu Ile Asp Leu Cys Asp
    1010                1015                1020
Arg Phe Cys Ala Pro Lys Gly Met Asp Pro Ile Phe Leu Ala Thr
    1025                1030                1035
Gly Trp Arg Gly Cys Trp Ala Gly Arg Ser Pro Ile Glu Gln Pro
    1040                1045                1050
Ser Glu Lys Pro Ile Ala Phe Ala Gln Leu Asp Glu Lys Lys Ile
    1055                1060                1065
Thr Ala Arg Thr Val Val Ala Gln Pro Tyr Asp Pro Asn Gln Ala
    1070                1075                1080
Val Lys Cys Leu Arg Val Leu Gln Ala Gly Gly Ala Met Val Ala
    1085                1090                1095
Lys Ala Val Pro Lys Val Val Lys Val Ser Ala Val Pro Phe Arg
    1100                1105                1110
Ala Pro Phe Phe Pro Thr Gly Val Lys Val Asp Pro Asp Cys Arg
    1115                1120                1125
Val Val Val Asp Pro Asp Thr Phe Thr Ala Ala Leu Arg Ser Gly
    1130                1135                1140
Tyr Ser Thr Thr Asn Leu Val Leu Gly Val Gly Asp Phe Ala Gln
    1145                1150                1155
Leu Asn Gly Leu Lys Ile Arg Gln Ile Ser Lys Pro Ser Gly Gly
    1160                1165                1170

<210> SEQ ID NO 4
<211> LENGTH: 3327
<212> TYPE: DNA
<213> ORGANISM: Porcine reproductive and respiratory syndrome virus

<400> SEQUENCE: 4
gctggaaaga gagcaagaaa agcacgctct tgtgcgactg ctacagtcgc tggccgcgct        60
```

-continued

| | |
|---|---|
| ttgtccgttc gtgaaacccg gcaggccaag gagcacgagg ttgccggcgc caacaaggct | 120 |
| gagcacctca acactactc cccgcctgcc gaagggaatt gtggttggca ctgcatttcc | 180 |
| gccatcgcca accggatggt gaattccaaa tttgaaacca cccttcccga aagagtgaga | 240 |
| cctccagatg actgggctac tgacgaggat cttgtgaatg ccatccaaat cctcagactc | 300 |
| cctgcggcct tagacaggaa cggtgcttgt actagcgcca agtacgtact taagctggaa | 360 |
| ggtgagcatt ggactgtcac tgtgacccct gggatgtccc cttctttgct ccctcttgaa | 420 |
| tgtgttcagg gctgttgtgg gcacaagggc ggtcttggtt ccccagatgc agtcgaggtc | 480 |
| tccggatttg accctgcctg ccttgaccgg ctggctgagg tgatgcacct gcctagcagt | 540 |
| gctatcccag ccgctctggc cgaaatgtct ggcgattccg atcgttcggc ttctccggtc | 600 |
| accaccgtgt ggactgtttc gcagttcttt gcccgtcaca gcggagggaa tcaccctgac | 660 |
| caagtgcgct tagggaaaat tatcagcctt tgtcaggtga ttgaggactg ctgctgttcc | 720 |
| cagaacaaaa ccaaccgggt cacccccggag gaggtcgcag caaagattga cctgtacctc | 780 |
| cgtggtgcaa caaatcttga agaatgcttg gccaggcttg agaaagcgcg cccgccacgc | 840 |
| gtaatcgaca ccttctttga ttgggatgtt gtgctccctg gggttgaggc ggcaacccag | 900 |
| acgatcaagc tgccccaggt caaccagtgt cgtgctctgg tccctgttgt gactcaaaag | 960 |
| tccttggaca caactcggt cccccctgacc gccttttcac tggctaacta ctactaccgt | 1020 |
| gcgcaaggtg acgaagttcg tcaccgtgaa agactaaccg ccgtgctctc caagttggaa | 1080 |
| aaggttgttc gagaagaata tgggctcatg ccaaccgagc ctggtccacg gcccacactg | 1140 |
| ccacgcgggc tcgacgaact caaagaccag atggaggagg acttgctgaa actggctaac | 1200 |
| gcccagacga cttcggacat gatggcctgg gcagtcgagc aggttgacct aaaaacttgg | 1260 |
| gtcaagaact acccgcggtg gacaccacca cccccctccgc caaaagttca gcctcgaaaa | 1320 |
| acgaagcctg tcaagagctt gccggagaga aagcctgtcc ccgccccgcg caggaaggtt | 1380 |
| gggtccgatt gtggcagccc ggtttcatta ggcggcgatg tccctaacag ttgggaagat | 1440 |
| ttggctgtta gtagcccctt tgatctcccg accccacctg agccggcaac accttcaagt | 1500 |
| gagctggtga ttgtgtcctc accgcaatgc atcttcaggc cggcgacacc cttgagtgag | 1560 |
| ccggctccaa ttcccgcacc tcgcggaact gtgtctcgac cggtgacacc cttgagtgag | 1620 |
| ccgatccctg tgcccgcacc gcggcgtaag tttcagcagg tgaaaagatt gagttcggcg | 1680 |
| gcggcaatcc caccgtacca gaacgagccc ctggatttgt ctgcttcctc acagactgaa | 1740 |
| tatgaggcct ctcccccagc accgccgcag agcgggggcg ttctgggagt agaggggcat | 1800 |
| gaagctgagg aaaccctgag tgaaatctcg gacatgtcgg gtaacattaa acctgcgtcc | 1860 |
| gtgtcatcaa gcagctcctt gtccagcgtg agaatcacac gcccaaaata ctcagctcaa | 1920 |
| gccatcatcg actcgggcgg gccctgcagt gggcatctcc aagaggtaaa ggaaacatgc | 1980 |
| cttagtgtca tgcgcgaggc atgtgatgcg actaagcttg atgaccctgc tacgcaggaa | 2040 |
| tggctttctc gcatgtggga tcgggtggac atgctgactt ggcgcaacac gtctgtttac | 2100 |
| caggcgattt gcaccttaga tggcaggtta agttcctcc caaaaatgat actcgagaca | 2160 |
| ccgccgccct atccgtcttt taccgatttg ccgccttcag atggcgcgga tgcggacggg | 2220 |
| gggggggccgt ttcggacggt aaaaagaaaa gctgaaaggc tctttgacca actgagccgt | 2280 |
| caggttttg acctcgtctc ccatctcct gttttcttct cacgcctttt ctaccctggc | 2340 |
| ggtggttatt ctccgggtga ttggggtttt gcagcttttta ctctattgtg cctcttttta | 2400 |
| tgttacagtt acccagcctt tggtattgct ccctctttgg gtgtgttttc tgggtcttct | 2460 |

-continued

```
cggcgcgttc gaatgggggt ttttggctgc tggttggctt ttgctgttgg tctgttcaag    2520
cctgtgtccg acccagtcgg cgctgcttgt gagtttgact cgccagagtg tagaaacatc    2580
cttcattctt ttgagcttct caaaccttgg gaccctgttc gcagccttgt tgtgggcccc    2640
gtcggtctcg gtcttgccat tcttggcagg ttactgggcg gggcacgctg catctggcac    2700
tttttgctta ggcttggcat tgttgcagac tgtatcttgg ctggagctta cgtgctttct    2760
caaggtaggt gtaaaaagtg ctggggatct tgtataagaa ctgctcctaa tgaggtcgct    2820
tttaacgtgt ttcctttcac acgtgcgacc aggtcgtcac ttatcgacct gtgcgatcgg    2880
ttttgtgcgc aaaaggaat ggaccccatt tttctcgcca ctgggtggcg cgggtgctgg    2940
gccggccgaa gccccattga gcaaccctct gaaaaaccca tcgcgtttgc ccaattggat    3000
gaaaagaaga ttacggctag gactgtggtc gcccagcctt atgaccccaa ccaagccgta    3060
aagtgcttgc gggtattgca ggcgggtggg gcgatggtgg ctaaggcggt cccaaaagtg    3120
gtcaaggttt ccgctgttcc attccgagcc cccttctttc ccactggagt gaaagttgac    3180
cctgattgca gggtcgtggt tgaccctgac actttcactg cagctctccg gtctggctac    3240
tccaccacaa acctcgtcct tggtgtaggg gactttgccc agctgaatgg attaaaaatc    3300
aggcaaattt ccaagccttc aggggga                                       3327
```

<210> SEQ ID NO 5
<211> LENGTH: 1109
<212> TYPE: PRT
<213> ORGANISM: Porcine reproductive and respiratory syndrome virus

<400> SEQUENCE: 5

```
Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
```

-continued

```
              210                 215                 220
Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
                260                 265                 270

Leu Glu Lys Ala Arg Pro Pro Arg Val Ile Asp Thr Phe Phe Asp Trp
                275                 280                 285

Asp Val Val Leu Pro Gly Val Glu Ala Ala Thr Gln Thr Ile Lys Leu
                290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
                340                 345                 350

Thr Ala Val Leu Ser Lys Leu Glu Lys Val Val Arg Glu Glu Tyr Gly
                355                 360                 365

Leu Met Pro Thr Glu Pro Gly Pro Arg Pro Thr Leu Pro Arg Gly Leu
                370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
                420                 425                 430

Pro Pro Lys Val Gln Pro Arg Lys Thr Lys Pro Val Lys Ser Leu Pro
                435                 440                 445

Glu Arg Lys Pro Val Pro Ala Pro Arg Arg Lys Val Gly Ser Asp Cys
450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
                485                 490                 495

Thr Pro Ser Ser Glu Leu Val Ile Val Ser Ser Pro Gln Cys Ile Phe
                500                 505                 510

Arg Pro Ala Thr Pro Leu Ser Glu Pro Ala Pro Ile Pro Ala Pro Arg
                515                 520                 525

Gly Thr Val Ser Arg Pro Val Thr Pro Leu Ser Glu Pro Ile Pro Val
                530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Pro Ala Pro Gln Ser Gly
                580                 585                 590

Gly Val Leu Gly Val Glu Gly His Glu Ala Glu Glu Thr Leu Ser Glu
                595                 600                 605

Ile Ser Asp Met Ser Gly Asn Ile Lys Pro Ala Ser Val Ser Ser Ser
                610                 615                 620

Ser Ser Leu Ser Ser Val Arg Ile Thr Arg Pro Lys Tyr Ser Ala Gln
625                 630                 635                 640
```

```
Ala Ile Ile Asp Ser Gly Gly Pro Cys Ser Gly His Leu Gln Glu Val
            645                 650                 655
Lys Glu Thr Cys Leu Ser Val Met Arg Glu Ala Cys Asp Ala Thr Lys
            660                 665                 670
Leu Asp Asp Pro Ala Thr Gln Glu Trp Leu Ser Arg Met Trp Asp Arg
            675                 680                 685
Val Asp Met Leu Thr Trp Arg Asn Thr Ser Val Tyr Gln Ala Ile Cys
690                 695                 700
Thr Leu Asp Gly Arg Leu Lys Phe Leu Pro Lys Met Ile Leu Glu Thr
705                 710                 715                 720
Pro Pro Pro Tyr Pro Ser Phe Thr Asp Leu Pro Pro Ser Asp Gly Ala
            725                 730                 735
Asp Ala Asp Gly Gly Gly Pro Phe Arg Thr Val Lys Arg Lys Ala Glu
            740                 745                 750
Arg Leu Phe Asp Gln Leu Ser Arg Gln Val Phe Asp Leu Val Ser His
            755                 760                 765
Leu Pro Val Phe Phe Ser Arg Leu Phe Tyr Pro Gly Gly Gly Tyr Ser
    770                 775                 780
Pro Gly Asp Trp Gly Phe Ala Ala Phe Thr Leu Leu Cys Leu Phe Leu
785                 790                 795                 800
Cys Tyr Ser Tyr Pro Ala Phe Gly Ile Ala Pro Leu Leu Gly Val Phe
            805                 810                 815
Ser Gly Ser Ser Arg Arg Val Arg Met Gly Val Phe Gly Cys Trp Leu
            820                 825                 830
Ala Phe Ala Val Gly Leu Phe Lys Pro Val Ser Asp Pro Val Gly Ala
            835                 840                 845
Ala Cys Glu Phe Asp Ser Pro Glu Cys Arg Asn Ile Leu His Ser Phe
            850                 855                 860
Glu Leu Leu Lys Pro Trp Asp Pro Val Arg Ser Leu Val Val Gly Pro
865                 870                 875                 880
Val Gly Leu Gly Leu Ala Ile Leu Gly Arg Leu Leu Gly Gly Ala Arg
            885                 890                 895
Cys Ile Trp His Phe Leu Leu Arg Leu Gly Ile Val Ala Asp Cys Ile
            900                 905                 910
Leu Ala Gly Ala Tyr Val Leu Ser Gln Gly Arg Cys Lys Lys Cys Trp
            915                 920                 925
Gly Ser Cys Ile Arg Thr Ala Pro Asn Glu Val Ala Phe Asn Val Phe
930                 935                 940
Pro Phe Thr Arg Ala Thr Arg Ser Ser Leu Ile Asp Leu Cys Asp Arg
945                 950                 955                 960
Phe Cys Ala Pro Lys Gly Met Asp Pro Ile Phe Leu Ala Thr Gly Trp
            965                 970                 975
Arg Gly Cys Trp Ala Gly Arg Ser Pro Ile Glu Gln Pro Ser Glu Lys
            980                 985                 990
Pro Ile Ala Phe Ala Gln Leu Asp Glu Lys Lys Ile Thr Ala Arg Thr
            995                 1000                1005
Val Val Ala Gln Pro Tyr Asp Pro Asn Gln Ala Val Lys Cys Leu
    1010                1015                1020
Arg Val Leu Gln Ala Gly Gly Ala Met Val Ala Lys Ala Val Pro
    1025                1030                1035
Lys Val Val Lys Val Ser Ala Val Pro Phe Arg Ala Pro Phe Phe
    1040                1045                1050
```

```
Pro Thr Gly Val Lys Val Asp Pro Asp Cys Arg Val Val Val Asp
    1055                1060                1065

Pro Asp Thr Phe Thr Ala Ala Leu Arg Ser Gly Tyr Ser Thr Thr
    1070                1075                1080

Asn Leu Val Leu Gly Val Gly Asp Phe Ala Gln Leu Asn Gly Leu
    1085                1090                1095

Lys Ile Arg Gln Ile Ser Lys Pro Ser Gly Gly
    1100                1105
```

<210> SEQ ID NO 6
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 6
ggcaagccca tccccaaccc actgctgggt ctagattcca cc                42

<210> SEQ ID NO 7
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 7

```
Gly Lys Pro Ile Pro Asn Pro Leu Leu Gly Leu Asp Ser Thr
1               5                   10
```

<210> SEQ ID NO 8
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 8
aaggagaccg cggccgctaa gttcgaacgc cagcatatgg attcc             45

<210> SEQ ID NO 9
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 9

```
Lys Glu Thr Ala Ala Ala Lys Phe Glu Arg Gln His Met Asp Ser
1               5                   10                  15
```

<210> SEQ ID NO 10
<211> LENGTH: 66
<212> TYPE: DNA
<213> ORGANISM: Artificial Sequence
<220> FEATURE:
<223> OTHER INFORMATION: Chemically Synthesized

<400> SEQUENCE: 10
gattataagg atcatgacgg cgattacaag gatcacgata tcgactacaa ggatgacgat    60
gacaag                                                               66

<210> SEQ ID NO 11
<211> LENGTH: 22

```
<212> TYPE: PRT
<213> ORGANISM: Artificial Sequence
<220> FEATURE:
<223> OTHER INFORMATION: Chemically Synthesized

<400> SEQUENCE: 11

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 12
<211> LENGTH: 3561
<212> TYPE: DNA
<213> ORGANISM: Porcine reproductive and respiratory syndrome virus

<400> SEQUENCE: 12
gctggaaaga gagcaagaaa agcacgctct tgtggcaagc ccatcccaa cccactgctg      60 ggtctagatt ccaccgccgg cgccaacaag gctgagcacc tcaaacacta ctccccgcct    120
gccgaaggga attgtggttg cactgcatt ccgccatcg ccaaccggat ggtgaattcc      180
aaatttgaaa ccaccttcc cgaaagagtg agacctccag atgactgggc tactgacgag    240
gatcttgtga atgccatcca atcctcaga ctccctgcgg ccttagacag gaacggtgct    300
tgtactagcg ccaagtacgt acttaagctg gaaggtgagc attggactgt cactgtgacc    360
cctgggatgt ccccttcttt gctccctctt gaatgtgttc agggctgttg tgggcacaag    420
ggcggtcttg gttccccaga tgcagtcgag gtctccggat ttgaccctgc ctgccttgac    480
cggctggctg aggtgatgca cctgcctagc agtgctatcc cagccgctct ggccgaaatg    540
tctggcgatt ccgatcgttc ggcttctccg gtcaccaccg tgtggactgt ttcgcagttc    600
tttgcccgtc acagcggagg gaatcaccct gaccaagtgc gcttagggaa aattatcagc    660
ctttgtcagg tgattgagga ctgctgctgt cccagaaca aaaccaaccg ggtcaccccg    720
gaggaggtcg cagcaaagat tgacctgtac ctccgtggtg caacaaatct gaagaatgc    780 ttggccaggc ttgagaaagc gcgcccgcca cgcgtaatcg acaccttctt tgattgggat    840
gttgtgctcc ctgggttga ggcggcaacc cagacgatca agctgcccca ggtcaaccag    900
tgtcgtgctc tggtccctgt tgtgactcaa aagtccttgg acaacaactc ggtcccctg    960 accgcctttt cactggctaa ctactactac cgtgcgcaag gtgacgaagt tcgtcaccgt   1020
gaaagactaa ccgccgtgct ctccaagttg gaaaaggttg ttcgagaaga atatgggctc   1080
atgccaaccg agcctggtcc acggcccaca ctgccacgcg gctcgacga actcaaagac   1140 cagatggagg aggacttgct gaaactggct aacgcccaga cgacttcgga catgatggcc   1200
tgggcagtcg agcaggttga cctaaaaact tgggtcaaga ctacccgcg gtggacacca   1260 ccacccctc cgccaaaagt tcagcctcga aaaacgaagc tgtcaagag cttgccggag   1320 agaaagcctg tccccgcccc gcgcaggaag gttgggtccg attgtggcag cccggtttca   1380
ttaggcggcg atgtccctaa cagttgggaa gatttggctg ttagtagccc ctttgatctc   1440 ccgacccac ctgagccggc aacaccttca agtgagctgg tgattgtgtc ctcaccgcaa   1500
tgcatcttca ggccggcgac accctttgagt gagccggctc caattcccgc acctcgcgga   1560
actgtgtctc gaccggtgac accctgagt gagccgatcc ctgtgcccgc accgcggcgt   1620
aagtttcagc aggtgaaaag attgagttcg cggcggcaa tcccaccgta ccagaacgag   1680
cccctggatt tgtctgcttc ctcacagact gaatatgagg cctctcccc agcaccgccg   1740
```

| | | |
|---|---|---|
| cagagcgggg gcgttctggg agtagagggg catgaagctg aggaaaccct gagtgaaatc | 1800 |
| tcggacatgt cgggtaacat taaacctgcg tccgtgtcat caagcagctc cttgtccagc | 1860 |
| gtgagaatca cacgcccaaa atactcagct caagccatca tcgactcggg cgggccctgc | 1920 |
| agtgggcatc tccaagaggt aaaggaaaca tgccttagtg tcatgcgcga ggcatgtgat | 1980 |
| gcgactaagc ttgatgaccc tgctacgcag gaatggcttt ctcgcatgtg ggatcgggtg | 2040 |
| gacatgctga cttggcgcaa cacgtctgtt taccaggcga tttgcacctt agatggcagg | 2100 |
| ttaaagttcc tcccaaaaat gatactcgag acaccgccgc cctatccgtg tgagtttgtg | 2160 |
| atgatgcctc acacgcctgc accttccgta ggtgcggaga gcgaccttac cattggctca | 2220 |
| gttgctactg aagatgttcc acgcatcctc gagaaaatag aaaatgtcgg cgagatggcc | 2280 |
| aaccagggac ccttggcctt ctccgaggat aaaccggtag atgaccaact tgtcaacgac | 2340 |
| cccggatat cgtcgcggag gcctgacgag agcacatcag ctccgtccgc aggcacaggt | 2400 |
| ggcgccggct cttttaccga tttgccgcct tcagatggcg cggatgcgga cgggggggg | 2460 |
| ccgtttcgga cggtaaaaag aaaagctgaa aggctctttg accaactgag ccgtcaggtt | 2520 |
| tttgacctcg tctcccatct ccctgttttc ttctcacgcc ttttctaccc tggcggtggt | 2580 |
| tattctccgg gtgattgggg ttttgcagct tttactctat tgtgcctctt tttatgttac | 2640 |
| agttacccag cctttggtat tgctcccctc ttgggtgtgt tttctgggtc ttctcggcgc | 2700 |
| gttcgaatgg gggttttggg ctgctggttg gcttttgctg ttggtctgtt caagcctgtg | 2760 |
| tccgacccag tcggcgctgc ttgtgagttt gactcgccag agtgtagaaa catccttcat | 2820 |
| tcttttgagc ttctcaaacc ttgggaccct gttcgcagcc ttgttgtggg ccccgtcggt | 2880 |
| ctcggtcttg ccattcttgg caggttactg ggcggggcac gctgcatctg cacttttttg | 2940 |
| cttaggcttg gcattgttgc agactgtatc ttggctggag cttacgtgct ttctcaaggt | 3000 |
| aggtgtaaaa agtgctgggg atcttgtata agaactgctc ctaatgaggt cgcttttaac | 3060 |
| gtgtttcctt tcacacgtgc gaccaggtcg tcacttatcg acctgtgcga tcggttttgt | 3120 |
| gcgccaaaag gaatggaccc catttttctc gccactgggt ggcgcgggtg ctgggccggc | 3180 |
| cgaagcccca ttgagcaacc ctctgaaaaa cccatcgcgt tgcccaatt ggatgaaaag | 3240 |
| aagattacgg ctaggactgt ggtcgcccag ccttatgacc ccaaccaagc cgtaaagtgc | 3300 |
| ttgcgggtat tgcaggcggg tggggcgatg gtggctaagg cggtcccaaa agtggtcaag | 3360 |
| gtttccgctg ttccattccg agcccccttc tttcccactg gagtgaaagt tgaccctgat | 3420 |
| tgcagggtcg tggttgaccc tgacactttc actgcagctc tccggtctgg ctactccacc | 3480 |
| acaaacctcg tccttggtgt aggggacttt gcccagctga atggattaaa aatcaggcaa | 3540 |
| atttccaagc cttcaggggg a | 3561 |

<210> SEQ ID NO 13
<211> LENGTH: 1187
<212> TYPE: PRT
<213> ORGANISM: Porcine reproductive and respiratory syndrome virus

<400> SEQUENCE: 13

Ala Gly Lys Arg Ala Arg Lys Ala Arg Ser Cys Gly Lys Pro Ile Pro
1               5                   10                  15

Asn Pro Leu Leu Gly Leu Asp Ser Thr Ala Gly Ala Asn Lys Ala Glu
            20                  25                  30

His Leu Lys His Tyr Ser Pro Pro Ala Glu Gly Asn Cys Gly Trp His
        35                  40                  45

-continued

```
Cys Ile Ser Ala Ile Ala Asn Arg Met Val Asn Ser Lys Phe Glu Thr
    50                  55                  60

Thr Leu Pro Glu Arg Val Arg Pro Pro Asp Asp Trp Ala Thr Asp Glu
65                  70                  75                  80

Asp Leu Val Asn Ala Ile Gln Ile Leu Arg Leu Pro Ala Ala Leu Asp
                85                  90                  95

Arg Asn Gly Ala Cys Thr Ser Ala Lys Tyr Val Leu Lys Leu Glu Gly
            100                 105                 110

Glu His Trp Thr Val Thr Val Thr Pro Gly Met Ser Pro Ser Leu Leu
        115                 120                 125

Pro Leu Glu Cys Val Gln Gly Cys Cys Gly His Lys Gly Gly Leu Gly
130                 135                 140

Ser Pro Asp Ala Val Glu Val Ser Gly Phe Asp Pro Ala Cys Leu Asp
145                 150                 155                 160

Arg Leu Ala Glu Val Met His Leu Pro Ser Ser Ala Ile Pro Ala Ala
                165                 170                 175

Leu Ala Glu Met Ser Gly Asp Ser Asp Arg Ser Ala Ser Pro Val Thr
            180                 185                 190

Thr Val Trp Thr Val Ser Gln Phe Phe Ala Arg His Ser Gly Gly Asn
        195                 200                 205

His Pro Asp Gln Val Arg Leu Gly Lys Ile Ile Ser Leu Cys Gln Val
    210                 215                 220

Ile Glu Asp Cys Cys Ser Gln Asn Lys Thr Asn Arg Val Thr Pro
225                 230                 235                 240

Glu Glu Val Ala Ala Lys Ile Asp Leu Tyr Leu Arg Gly Ala Thr Asn
                245                 250                 255

Leu Glu Glu Cys Leu Ala Arg Leu Glu Lys Ala Arg Pro Pro Arg Val
            260                 265                 270

Ile Asp Thr Phe Phe Asp Trp Asp Val Val Leu Pro Gly Val Glu Ala
        275                 280                 285

Ala Thr Gln Thr Ile Lys Leu Pro Gln Val Asn Gln Cys Arg Ala Leu
    290                 295                 300

Val Pro Val Val Thr Gln Lys Ser Leu Asp Asn Asn Ser Val Pro Leu
305                 310                 315                 320

Thr Ala Phe Ser Leu Ala Asn Tyr Tyr Tyr Arg Ala Gln Gly Asp Glu
                325                 330                 335

Val Arg His Arg Glu Arg Leu Thr Ala Val Leu Ser Lys Leu Glu Lys
            340                 345                 350

Val Val Arg Glu Glu Tyr Gly Leu Met Pro Thr Glu Pro Gly Pro Arg
        355                 360                 365

Pro Thr Leu Pro Arg Gly Leu Asp Glu Leu Lys Asp Gln Met Glu Glu
    370                 375                 380

Asp Leu Leu Lys Leu Ala Asn Ala Gln Thr Thr Ser Asp Met Met Ala
385                 390                 395                 400

Trp Ala Val Glu Gln Val Asp Leu Lys Thr Trp Val Lys Asn Tyr Pro
                405                 410                 415

Arg Trp Thr Pro Pro Pro Pro Lys Val Gln Pro Arg Lys Thr
            420                 425                 430

Lys Pro Val Lys Ser Leu Pro Glu Arg Lys Pro Val Pro Ala Pro Arg
        435                 440                 445

Arg Lys Val Gly Ser Asp Cys Gly Ser Pro Val Ser Leu Gly Gly Asp
    450                 455                 460

Val Pro Asn Ser Trp Glu Asp Leu Ala Val Ser Ser Pro Phe Asp Leu
```

-continued

```
            465                 470                 475                 480
        Pro Thr Pro Pro Glu Pro Ala Thr Pro Ser Ser Glu Leu Val Ile Val
                            485                 490                 495
        Ser Ser Pro Gln Cys Ile Phe Arg Pro Ala Thr Pro Leu Ser Glu Pro
                            500                 505                 510
        Ala Pro Ile Pro Ala Pro Arg Gly Thr Val Ser Arg Pro Val Thr Pro
                            515                 520                 525
        Leu Ser Glu Pro Ile Pro Val Pro Ala Pro Arg Arg Lys Phe Gln Gln
                530                 535                 540
        Val Lys Arg Leu Ser Ala Ala Ala Ile Pro Pro Tyr Gln Asn Glu
        545                 550                 555                 560
        Pro Leu Asp Leu Ser Ala Ser Ser Gln Thr Glu Tyr Glu Ala Ser Pro
                            565                 570                 575
        Pro Ala Pro Pro Gln Ser Gly Gly Val Leu Gly Val Glu Gly His Glu
                            580                 585                 590
        Ala Glu Glu Thr Leu Ser Glu Ile Ser Asp Met Ser Gly Asn Ile Lys
                            595                 600                 605
        Pro Ala Ser Val Ser Ser Ser Ser Leu Ser Ser Val Arg Ile Thr
                610                 615                 620
        Arg Pro Lys Tyr Ser Ala Gln Ala Ile Ile Asp Ser Gly Gly Pro Cys
        625                 630                 635                 640
        Ser Gly His Leu Gln Glu Val Lys Glu Thr Cys Leu Ser Val Met Arg
                            645                 650                 655
        Glu Ala Cys Asp Ala Thr Lys Leu Asp Asp Pro Ala Thr Gln Glu Trp
                            660                 665                 670
        Leu Ser Arg Met Trp Asp Arg Val Asp Met Leu Thr Trp Arg Asn Thr
                            675                 680                 685
        Ser Val Tyr Gln Ala Ile Cys Thr Leu Asp Gly Arg Leu Lys Phe Leu
                690                 695                 700
        Pro Lys Met Ile Leu Glu Thr Pro Pro Tyr Pro Cys Glu Phe Val
        705                 710                 715                 720
        Met Met Pro His Thr Pro Ala Pro Ser Val Gly Ala Glu Ser Asp Leu
                            725                 730                 735
        Thr Ile Gly Ser Val Ala Thr Glu Asp Val Pro Arg Ile Leu Glu Lys
                            740                 745                 750
        Ile Glu Asn Val Gly Glu Met Ala Asn Gln Gly Pro Leu Ala Phe Ser
                            755                 760                 765
        Glu Asp Lys Pro Val Asp Asp Gln Leu Val Asn Asp Pro Arg Ile Ser
                770                 775                 780
        Ser Arg Arg Pro Asp Glu Ser Thr Ser Ala Pro Ser Ala Gly Thr Gly
        785                 790                 795                 800
        Gly Ala Gly Ser Phe Thr Asp Leu Pro Pro Ser Asp Gly Ala Asp Ala
                            805                 810                 815
        Asp Gly Gly Gly Pro Phe Arg Thr Val Lys Arg Lys Ala Glu Arg Leu
                            820                 825                 830
        Phe Asp Gln Leu Ser Arg Gln Val Phe Asp Leu Val Ser His Leu Pro
                            835                 840                 845
        Val Phe Phe Ser Arg Leu Phe Tyr Pro Gly Gly Tyr Ser Pro Gly
                850                 855                 860
        Asp Trp Gly Phe Ala Ala Phe Thr Leu Leu Cys Leu Phe Leu Cys Tyr
        865                 870                 875                 880
        Ser Tyr Pro Ala Phe Gly Ile Ala Pro Leu Leu Gly Val Phe Ser Gly
                            885                 890                 895
```

Ser Ser Arg Arg Val Arg Met Gly Val Phe Gly Cys Trp Leu Ala Phe
                900                 905                 910

Ala Val Gly Leu Phe Lys Pro Val Ser Asp Pro Val Gly Ala Ala Cys
    915                 920                 925

Glu Phe Asp Ser Pro Glu Cys Arg Asn Ile Leu His Ser Phe Glu Leu
        930                 935                 940

Leu Lys Pro Trp Asp Pro Val Arg Ser Leu Val Val Gly Pro Val Gly
945                 950                 955                 960

Leu Gly Leu Ala Ile Leu Gly Arg Leu Leu Gly Gly Ala Arg Cys Ile
            965                 970                 975

Trp His Phe Leu Leu Arg Leu Gly Ile Val Ala Asp Cys Ile Leu Ala
                980                 985                 990

Gly Ala Tyr Val Leu Ser Gln Gly Arg Cys Lys Lys Cys Trp Gly Ser
        995                 1000                1005

Cys Ile Arg Thr Ala Pro Asn Glu Val Ala Phe Asn Val Phe Pro
1010                1015                1020

Phe Thr Arg Ala Thr Arg Ser Ser Leu Ile Asp Leu Cys Asp Arg
1025                1030                1035

Phe Cys Ala Pro Lys Gly Met Asp Pro Ile Phe Leu Ala Thr Gly
1040                1045                1050

Trp Arg Gly Cys Trp Ala Gly Arg Ser Pro Ile Glu Gln Pro Ser
1055                1060                1065

Glu Lys Pro Ile Ala Phe Ala Gln Leu Asp Glu Lys Lys Ile Thr
1070                1075                1080

Ala Arg Thr Val Val Ala Gln Pro Tyr Asp Pro Asn Gln Ala Val
1085                1090                1095

Lys Cys Leu Arg Val Leu Gln Ala Gly Gly Ala Met Val Ala Lys
1100                1105                1110

Ala Val Pro Lys Val Val Lys Val Ser Ala Val Pro Phe Arg Ala
1115                1120                1125

Pro Phe Phe Pro Thr Gly Val Lys Val Asp Pro Asp Cys Arg Val
1130                1135                1140

Val Val Asp Pro Asp Thr Phe Thr Ala Ala Leu Arg Ser Gly Tyr
1145                1150                1155

Ser Thr Thr Asn Leu Val Leu Gly Val Gly Asp Phe Ala Gln Leu
1160                1165                1170

Asn Gly Leu Lys Ile Arg Gln Ile Ser Lys Pro Ser Gly Gly
1175                1180                1185

<210> SEQ ID NO 14
<211> LENGTH: 3564
<212> TYPE: DNA
<213> ORGANISM: Porcine reproductive and respiratory syndrome virus

<400> SEQUENCE: 14
gctggaaaga gagcaagaaa agcacgctct tgtaaggaga ccgcggccgc taagttcgaa     60
cgccagcata tggattccgc cggcgccaac aaggctgagc acctcaaaca ctactccccg    120
cctgccgaag ggaattgtgg ttggcactgc atttccgcca tcgccaaccg gatggtgaat    180
tccaaatttg aaaccaccct tcccgaaaga gtgagacctc agatgactg ggctactgac    240 gaggatcttg tgaatgccat ccaaatcctc agactccctg cggccttaga caggaacggt    300
gcttgtacta cgccaagta cgtacttaag ctggaaggtg agcattggac tgtcactgtg    360
accctgggga tgtccccttc tttgctccct cttgaatgtg ttcagggctg ttgtgggcac    420

```
aagggcggtc ttggttcccc agatgcagtc gaggtctccg gatttgaccc tgcctgcctt      480
gaccggctgg ctgaggtgat gcacctgcct agcagtgcta tcccagccgc tctggccgaa      540
atgtctggcg attccgatcg ttcggcttct ccggtcacca ccgtgtggac tgtttcgcag      600
ttctttgccc gtcacagcgg agggaatcac cctgaccaag tgcgcttagg gaaaattatc      660
agcctttgtc aggtgattga ggactgctgc tgttcccaga acaaaaccaa ccgggtcacc      720
ccggaggagg tcgcagcaaa gattgacctg tacctccgtg gtgcaacaaa tcttgaagaa      780
tgcttggcca ggcttgagaa agcgcgcccg ccacgcgtaa tcgacacctt ctttgattgg      840
gatgttgtgc tccctggggt tgaggcggca acccagacga tcaagctgcc ccaggtcaac      900
cagtgtcgtg ctctggtccc tgttgtgact caaaagtcct ggacaacaa ctcggtcccc       960
ctgaccgcct tttcactggc taactactac taccgtgcgc aaggtgacga agttcgtcac     1020
cgtgaaagac taaccgccgt gctctccaag ttggaaaagg ttgttcgaga gaatatgggg     1080
ctcatgccaa ccgagcctgg tccacggccc acactgccac gcgggctcga cgaactcaaa     1140
gaccagatgg aggaggactt gctgaaactg gctaacgccc agacgacttc ggacatgatg     1200
gcctgggcag tcgagcaggt tgacctaaaa acttgggtca agaactaccc gcggtggaca     1260
ccaccacccc ctccgccaaa agttcagcct cgaaaaacga agcctgtcaa gagcttgccg     1320
gagagaaagc ctgtccccgc cccgcgcagg aaggttgggt ccgattgtgg cagcccggtt     1380
tcattaggcg gcgatgtccc taacagttgg gaagatttgg ctgttagtag ccccctttgat   1440
ctcccgaccc cacctgagcc ggcaacacct tcaagtgagc tggtgattgt gtcctcaccg     1500
caatgcatct tcaggccggc gacacccttg agtgagccgg ctccaattcc cgcacctcgc     1560
ggaactgtgt ctcgaccggt gacacccttg agtgagccga tccctgtgcc cgcaccgcgg     1620
cgtaagtttc agcaggtgaa aagattgagt tcggcggcgg caatcccacc gtaccagaac     1680
gagcccctgg atttgtctgc ttcctcacag actgaatatg aggcctctcc cccagcaccg     1740
ccgcagagcg ggggcgttct gggagtagag gggcatgaag ctgaggaaac cctgagtgaa     1800
atctcggaca tgtcgggtaa cattaaacct gcgtccgtgt catcaagcag ctccttgtcc     1860
agcgtgagaa tcacacgccc aaaatactca gctcaagcca tcatcgactc gggcgggccc     1920
tgcagtgggc atctccaaga ggtaaaggaa acatgcctta gtgtcatgcg cgaggcatgt     1980
gatgcgacta agcttgatga ccctgctacg caggaatggc tttctcgcat gtgggatcgg     2040
gtggacatgc tgacttggcg caacacgtct gtttaccagg cgatttgcac cttagatggc     2100
aggttaaagt tcctcccaaa aatgatactc gagacaccgc cgccctatcc gtgtgagttt     2160
gtgatgatgc ctcacacgcc tgcaccttcc gtaggtgcgg agagcgacct taccattggc     2220
tcagttgcta ctgaagatgt tccacgcatc ctcgagaaaa tagaaaatgt cggcgagatg     2280
gccaaccagg gaccccttggc cttctccgag gataaaccgg tagatgacca acttgtcaac     2340
gaccccccgga tatcgtcgcg gaggcctgac gagagcacat cagctccgtc cgcaggcaca    2400
ggtggcgccg gctcttttac cgatttgccg ccttcagatg gcgcggatgc ggacgggggg     2460
gggccgtttc ggacggtaaa aagaaaagct gaaaggctct ttgaccaact gagccgtcag     2520
gtttttgacc tcgtctccca tctccctgtt ttcttctcac gccttttcta ccctggcggt     2580
ggttattctc cgggtgattg gggttttgca gcttttactc tattgtgcct cttttatgt      2640
tacagttacc cagcctttgg tattgctccc ctcttgggtg tgttttctgg gtcttctcgg     2700
cgcgttcgaa tgggggtttt tggctgctgg ttggcttttg ctgttggtct gttcaagcct     2760
```

```
gtgtccgacc cagtcggcgc tgcttgtgag tttgactcgc cagagtgtag aaacatcctt    2820
cattcttttg agcttctcaa acctgggac cctgttcgca gccttgttgt gggccccgtc    2880
ggtctcggtc ttgccattct tggcaggtta ctgggcgggg cacgctgcat ctggcacttt    2940
ttgcttaggc ttggcattgt tgcagactgt atcttggctg gagcttacgt gctttctcaa    3000
ggtaggtgta aaaagtgctg gggatcttgt ataagaactg ctcctaatga ggtcgctttt    3060
aacgtgtttc ctttcacacg tgcgaccagg tcgtcactta tcgacctgtg cgatcggttt    3120
tgtgcgccaa aggaatgga ccccattttt ctcgccactg ggtggcgcgg gtgctgggcc    3180
ggccgaagcc ccattgagca accctctgaa aaacccatcg cgtttgccca attggatgaa    3240
aagaagatta cggctaggac tgtggtcgcc cagccttatg accccaacca agccgtaaag    3300
tgcttgcggg tattgcaggc gggtggggcg atggtggcta aggcggtccc aaaagtggtc    3360
aaggtttccg ctgttccatt ccgagccccc ttctttccca ctggagtgaa agttgaccct    3420
gattgcaggg tcgtggttga ccctgacact tcactgcag ctctccggtc tggctactcc    3480
accacaaacc tcgtccttgg tgtaggggac tttgcccagc tgaatggatt aaaaatcagg    3540
caaatttcca agccttcagg ggga                                          3564
```

<210> SEQ ID NO 15
<211> LENGTH: 1188
<212> TYPE: PRT
<213> ORGANISM: Porcine reproductive and respiratory syndrome virus

<400> SEQUENCE: 15

```
Ala Gly Lys Arg Ala Arg Lys Ala Arg Ser Cys Lys Glu Thr Ala Ala
1               5                   10                  15

Ala Lys Phe Glu Arg Gln His Met Asp Ser Ala Gly Ala Asn Lys Ala
            20                  25                  30

Glu His Leu Lys His Tyr Ser Pro Ala Glu Gly Asn Cys Gly Trp
        35                  40                  45

His Cys Ile Ser Ala Ile Ala Asn Arg Met Val Asn Ser Lys Phe Glu
    50                  55                  60

Thr Thr Leu Pro Glu Arg Val Arg Pro Pro Asp Asp Trp Ala Thr Asp
65                  70                  75                  80

Glu Asp Leu Val Asn Ala Ile Gln Ile Leu Arg Leu Pro Ala Ala Leu
                85                  90                  95

Asp Arg Asn Gly Ala Cys Thr Ser Ala Lys Tyr Val Leu Lys Leu Glu
            100                 105                 110

Gly Glu His Trp Thr Val Thr Val Thr Pro Gly Met Ser Pro Ser Leu
        115                 120                 125

Leu Pro Leu Glu Cys Val Gln Gly Cys Cys Gly His Lys Gly Gly Leu
    130                 135                 140

Gly Ser Pro Asp Ala Val Glu Val Ser Gly Phe Asp Pro Ala Cys Leu
145                 150                 155                 160

Asp Arg Leu Ala Glu Val Met His Leu Pro Ser Ser Ala Ile Pro Ala
                165                 170                 175

Ala Leu Ala Glu Met Ser Gly Asp Ser Asp Arg Ser Ala Ser Pro Val
            180                 185                 190

Thr Thr Val Trp Thr Val Ser Gln Phe Phe Ala Arg His Ser Gly Gly
        195                 200                 205

Asn His Pro Asp Gln Val Arg Leu Gly Lys Ile Ile Ser Leu Cys Gln
    210                 215                 220

Val Ile Glu Asp Cys Cys Cys Ser Gln Asn Lys Thr Asn Arg Val Thr
```

-continued

```
        225                 230                 235                 240
Pro Glu Glu Val Ala Ala Lys Ile Asp Leu Tyr Leu Arg Gly Ala Thr
                245                 250                 255

Asn Leu Glu Glu Cys Leu Ala Arg Leu Glu Lys Ala Arg Pro Pro Arg
            260                 265                 270

Val Ile Asp Thr Phe Phe Asp Trp Asp Val Val Leu Pro Gly Val Glu
        275                 280                 285

Ala Ala Thr Gln Thr Ile Lys Leu Pro Gln Val Asn Gln Cys Arg Ala
    290                 295                 300

Leu Val Pro Val Val Thr Gln Lys Ser Leu Asp Asn Asn Ser Val Pro
305                 310                 315                 320

Leu Thr Ala Phe Ser Leu Ala Asn Tyr Tyr Arg Ala Gln Gly Asp
                325                 330                 335

Glu Val Arg His Arg Glu Arg Leu Thr Ala Val Leu Ser Lys Leu Glu
                340                 345                 350

Lys Val Val Arg Glu Glu Tyr Gly Leu Met Pro Thr Glu Pro Gly Pro
                355                 360                 365

Arg Pro Thr Leu Pro Arg Gly Leu Asp Glu Leu Lys Asp Gln Met Glu
    370                 375                 380

Glu Asp Leu Leu Lys Leu Ala Asn Ala Gln Thr Thr Ser Asp Met Met
385                 390                 395                 400

Ala Trp Ala Val Glu Gln Val Asp Leu Lys Thr Trp Val Lys Asn Tyr
                405                 410                 415

Pro Arg Trp Thr Pro Pro Pro Pro Lys Val Gln Pro Arg Lys
                420                 425                 430

Thr Lys Pro Val Lys Ser Leu Pro Glu Arg Lys Pro Val Pro Ala Pro
                435                 440                 445

Arg Arg Lys Val Gly Ser Asp Cys Gly Ser Pro Val Ser Leu Gly Gly
            450                 455                 460

Asp Val Pro Asn Ser Trp Glu Asp Leu Ala Val Ser Ser Pro Phe Asp
465                 470                 475                 480

Leu Pro Thr Pro Pro Glu Pro Ala Thr Pro Ser Ser Glu Leu Val Ile
                485                 490                 495

Val Ser Ser Pro Gln Cys Ile Phe Arg Pro Ala Thr Pro Leu Ser Glu
                500                 505                 510

Pro Ala Pro Ile Pro Ala Pro Arg Gly Thr Val Ser Arg Pro Val Thr
                515                 520                 525

Pro Leu Ser Glu Pro Ile Pro Val Pro Ala Pro Arg Arg Lys Phe Gln
    530                 535                 540

Gln Val Lys Arg Leu Ser Ser Ala Ala Ala Ile Pro Pro Tyr Gln Asn
545                 550                 555                 560

Glu Pro Leu Asp Leu Ser Ala Ser Ser Gln Thr Glu Tyr Glu Ala Ser
                565                 570                 575

Pro Pro Ala Pro Pro Gln Ser Gly Gly Val Leu Gly Val Glu Gly His
            580                 585                 590

Glu Ala Glu Glu Thr Leu Ser Glu Ile Ser Asp Met Ser Gly Asn Ile
                595                 600                 605

Lys Pro Ala Ser Val Ser Ser Ser Ser Leu Ser Ser Val Arg Ile
                610                 615                 620

Thr Arg Pro Lys Tyr Ser Ala Gln Ala Ile Ile Asp Ser Gly Gly Pro
625                 630                 635                 640

Cys Ser Gly His Leu Gln Glu Val Lys Glu Thr Cys Leu Ser Val Met
                645                 650                 655
```

-continued

Arg Glu Ala Cys Asp Ala Thr Lys Leu Asp Asp Pro Ala Thr Gln Glu
            660                 665                 670

Trp Leu Ser Arg Met Trp Asp Arg Val Asp Met Leu Thr Trp Arg Asn
            675                 680                 685

Thr Ser Val Tyr Gln Ala Ile Cys Thr Leu Asp Gly Arg Leu Lys Phe
        690                 695                 700

Leu Pro Lys Met Ile Leu Glu Thr Pro Pro Tyr Pro Cys Glu Phe
705                 710                 715                 720

Val Met Met Pro His Thr Pro Ala Pro Ser Val Gly Ala Glu Ser Asp
                725                 730                 735

Leu Thr Ile Gly Ser Val Ala Thr Glu Asp Val Pro Arg Ile Leu Glu
            740                 745                 750

Lys Ile Glu Asn Val Gly Glu Met Ala Asn Gln Gly Pro Leu Ala Phe
            755                 760                 765

Ser Glu Asp Lys Pro Val Asp Asp Gln Leu Val Asn Asp Pro Arg Ile
        770                 775                 780

Ser Ser Arg Arg Pro Asp Glu Ser Thr Ser Ala Pro Ser Ala Gly Thr
785                 790                 795                 800

Gly Gly Ala Gly Ser Phe Thr Asp Leu Pro Pro Ser Asp Gly Ala Asp
                805                 810                 815

Ala Asp Gly Gly Gly Pro Phe Arg Thr Val Lys Arg Lys Ala Glu Arg
            820                 825                 830

Leu Phe Asp Gln Leu Ser Arg Gln Val Phe Asp Leu Val Ser His Leu
        835                 840                 845

Pro Val Phe Phe Ser Arg Leu Phe Tyr Pro Gly Gly Tyr Ser Pro
850                 855                 860

Gly Asp Trp Gly Phe Ala Ala Phe Thr Leu Leu Cys Leu Phe Leu Cys
865                 870                 875                 880

Tyr Ser Tyr Pro Ala Phe Gly Ile Ala Pro Leu Leu Gly Val Phe Ser
                885                 890                 895

Gly Ser Ser Arg Arg Val Arg Met Gly Val Phe Gly Cys Trp Leu Ala
            900                 905                 910

Phe Ala Val Gly Leu Phe Lys Pro Val Ser Asp Pro Val Gly Ala Ala
        915                 920                 925

Cys Glu Phe Asp Ser Pro Glu Cys Arg Asn Ile Leu His Ser Phe Glu
930                 935                 940

Leu Leu Lys Pro Trp Asp Pro Val Arg Ser Leu Val Val Gly Pro Val
945                 950                 955                 960

Gly Leu Gly Leu Ala Ile Leu Gly Arg Leu Leu Gly Ala Arg Cys
            965                 970                 975

Ile Trp His Phe Leu Leu Arg Leu Gly Ile Val Ala Asp Cys Ile Leu
            980                 985                 990

Ala Gly Ala Tyr Val Leu Ser Gln Gly Arg Cys Lys Lys Cys Trp Gly
        995                 1000                1005

Ser Cys Ile Arg Thr Ala Pro Asn Glu Val Ala Phe Asn Val Phe
        1010                1015                1020

Pro Phe Thr Arg Ala Thr Arg Ser Ser Leu Ile Asp Leu Cys Asp
        1025                1030                1035

Arg Phe Cys Ala Pro Lys Gly Met Asp Pro Ile Phe Leu Ala Thr
        1040                1045                1050

Gly Trp Arg Gly Cys Trp Ala Gly Arg Ser Pro Ile Glu Gln Pro
        1055                1060                1065

```
Ser Glu Lys Pro Ile Ala Phe Ala Gln Leu Asp Glu Lys Lys Ile
    1070            1075                1080

Thr Ala Arg Thr Val Val Ala Gln Pro Tyr Asp Pro Asn Gln Ala
    1085            1090                1095

Val Lys Cys Leu Arg Val Leu Gln Ala Gly Gly Ala Met Val Ala
    1100            1105                1110

Lys Ala Val Pro Lys Val Val Lys Val Ser Ala Val Pro Phe Arg
    1115            1120                1125

Ala Pro Phe Phe Pro Thr Gly Val Lys Val Asp Pro Asp Cys Arg
    1130            1135                1140

Val Val Val Asp Pro Asp Thr Phe Thr Ala Ala Leu Arg Ser Gly
    1145            1150                1155

Tyr Ser Thr Thr Asn Leu Val Leu Gly Val Gly Asp Phe Ala Gln
    1160            1165                1170

Leu Asn Gly Leu Lys Ile Arg Gln Ile Ser Lys Pro Ser Gly Gly
    1175            1180                1185

<210> SEQ ID NO 16
<211> LENGTH: 3585
<212> TYPE: DNA
<213> ORGANISM: Porcine reproductive and respiratory syndrome virus

<400> SEQUENCE: 16
gctggaaaga gagcaagaaa agcacgctct tgtgattata aggatcatga cggcgattac        60
aaggatcacg atatcgacta caaggatgac gatgacaagg ccggcgccaa caaggctgag       120
cacctcaaac actactcccc gcctgccgaa gggaattgtg gttggcactg catttccgcc       180
atcgccaacc ggatggtgaa ttccaaattt gaaaccaccc ttcccgaaag agtgagacct       240
ccagatgact gggctactga cgaggatctt gtgaatgcca tccaaatcct cagactccct       300
gcggccttag acaggaacgg tgcttgtact agcgccaagt acgtacttaa gctggaaggt       360
gagcattgga ctgtcactgt gacccctggg atgtcccctt ctttgctccc tcttgaatgt       420
gttcagggct gttgtgggca aagggcggt cttggttccc cagatgcagt cgaggtctcc       480
ggatttgacc ctgcctgcct tgaccggctg gctgaggtga tgcacctgcc tagcagtgct       540
atcccagccg ctctggccga aatgtctggc gattccgatc gttcggcttc tccggtcacc       600
accgtgtgga ctgtttcgca gttctttgcc cgtcacagcg agggaatca ccctgaccaa       660 gtgcgcttag ggaaaattat cagcctttgt caggtgattg aggactgctg ctgttcccag       720
aacaaaacca accgggtcac cccggaggag gtcgcagcaa agattgacct gtacctccgt       780
ggtgcaacaa atcttgaaga atgcttggcc aggcttgaga aagcgcgccc gccacgcgta       840
atcgacacct tctttgattg ggatgttgtg ctccctgggg ttgaggcggc aacccagacg       900
atcaagctgc cccaggtcaa ccagtgtcgt gctctggtcc ctgttgtgac tcaaaagtcc       960
ttggacaaca actcggtccc cctgaccgcc ttttcactgg ctaactacta ctaccgtgcg      1020
caaggtgacg aagttcgtca ccgtgaaaga ctaaccgccg tgctctccaa gttggaaaag      1080
gttgttcgag aagaatatgg gctcatgcca accgagcctg tccacggcc cacactgcca      1140 cgcgggctcg acgaactcaa agaccagatg gaggaggact gctgaaact ggctaacgcc      1200 cagacgactt cggacatgat ggcctgggca gtcgagcagg ttgacctaaa acttgggtc      1260 aagaactacc gcggtggac accaccaccc cctccgccaa agttcagcc tcgaaaaacg      1320 aagcctgtca agagcttgcc ggagagaaag cctgtccccg cccgcgcag gaaggttggg      1380 tccgattgtg gcagcccggt ttcattaggc ggcgatgtcc ctaacagttg ggaagatttg      1440
```

```
gctgttagta gcccctttga tctcccgacc ccacctgagc cggcaacacc ttcaagtgag   1500
ctggtgattg tgtcctcacc gcaatgcatc ttcaggccgg cgacaccctt gagtgagccg   1560
gctccaattc ccgcacctcg cggaactgtg tctcgaccgg tgacacccct gagtgagccg   1620
atccctgtgc ccgcaccgcg gcgtaagttt cagcaggtga aaagattgag ttcggcggcg   1680
gcaatcccac cgtaccagaa cgagcccctg gatttgtctg cttcctcaca gactgaatat   1740
gaggcctctc ccccagcacc gccgcagagc gggggcgttc tgggagtaga ggggcatgaa   1800
gctgaggaaa ccctgagtga aatctcggac atgtcgggta acattaaacc tgcgtccgtg   1860
tcatcaagca gctccttgtc cagcgtgaga atcacacgcc caaaatactc agctcaagcc   1920
atcatcgact cgggcgggcc ctgcagtggg catctccaag aggtaaagga aacatgcctt   1980
agtgtcatgc gcgaggcatg tgatgcgact aagcttgatg accctgctac gcaggaatgg   2040
cttctctcgc atgtgggatc ggtggacatg ctgacttggc gcaacacgtc tgtttaccag   2100
gcgatttgca ccttagatgg caggttaaag ttcctcccaa aaatgatact cgagacaccg   2160
ccgccctatc cgtgtgagtt tgtgatgatg cctcacacgc ctgcaccttc cgtaggtgcg   2220
gagagcgacc ttaccattgg ctcagttgct actgaagatg ttccacgcat cctcgagaaa   2280
atagaaaatg tcggcgagat ggccaaccag ggaccccttg ccttctccga ggataaaccg   2340
gtagatgacc aacttgtcaa cgaccccccgg atatcgtcgc ggaggcctga cgagagcaca   2400
tcagctccgt ccgcaggcac aggtggcgcc ggctctttta ccgatttgcc gccttcagat   2460
ggcgcggatg cggacggggg ggggccgttt cggacggtaa aaagaaaagc tgaaaggctc   2520
tttgaccaac tgagccgtca ggttttttgac ctcgtctccc atctccctgt tttcttctca   2580
cgccttttct accctggcgg tggttattct ccgggtgatt ggggttttgc agcttttact   2640
ctattgtgcc tctttttatg ttacagttac ccagcctttg gtattgctcc cctcttgggt   2700
gtgttttctg ggtcttctcg gcgcgttcga atggggggttt ttggctgctg gttggctttt   2760
gctgttggtc tgttcaagcc tgtgtccgac ccagtcggcg ctgcttgtga gtttgactcg   2820
ccagagtgta gaaacatcct tcattctttt gagcttctca aaccttggga ccctgttcgc   2880
agccttgttg tgggccccgt cggtctcggt cttgccattc ttggcaggtt actgggcggg   2940
gcacgctgca tctggcactt ttttgcttagg cttggcattg ttgcagactg tatcttggct   3000
ggagcttacg tgctttctca aggtaggtgt aaaaagtgct ggggatcttg tataagaact   3060
gctcctaatg aggtcgcttt taacgtgttt cctttcacac gtgcgaccag gtcgtcactt   3120
atcgacctgt gcgatcggtt ttgtgcgcca aaaggaatgg accccatttt tctcgccact   3180
gggtggcgcg ggtgctgggc cggccgaagc cccattgagc aaccctctga aaaacccatc   3240
gcgtttgccc aattggatga aaagaagatt acggctagga ctgtggtcgc ccagccttat   3300 gacccccaacc aagccgtaaa gtgcttgcgg gtattgcagg cgggtggggc gatggtggct   3360
aaggcggtcc caaaagtggt caaggttccc gctgttccat ccagccccc cttctttccc   3420 actggagtga agttgacccc tgattgcagg gtcgtggttg accctgacac tttcactgca   3480
gctctccggt ctggctactc caccacaaac ctcgtccttg gtgtagggga ctttgcccag   3540
ctgaatggat taaaaatcag gcaaatttcc aagccttcag gggga             3585
```

<210> SEQ ID NO 17
<211> LENGTH: 1195
<212> TYPE: PRT
<213> ORGANISM: Porcine reproductive and respiratory syndrome virus

```
<400> SEQUENCE: 17

Ala Gly Lys Arg Ala Arg Lys Ala Arg Ser Cys Asp Tyr Lys Asp His
1               5                   10                  15

Asp Gly Asp Tyr Lys Asp His Asp Ile Asp Tyr Lys Asp Asp Asp
            20                  25                  30

Lys Ala Gly Ala Asn Lys Ala Glu His Leu Lys His Tyr Ser Pro Pro
            35                  40                  45

Ala Glu Gly Asn Cys Gly Trp His Cys Ile Ser Ala Ile Ala Asn Arg
        50                  55                  60

Met Val Asn Ser Lys Phe Glu Thr Thr Leu Pro Glu Arg Val Arg Pro
65                  70                  75                  80

Pro Asp Asp Trp Ala Thr Asp Glu Asp Leu Val Asn Ala Ile Gln Ile
                85                  90                  95

Leu Arg Leu Pro Ala Ala Leu Asp Arg Asn Gly Ala Cys Thr Ser Ala
            100                 105                 110

Lys Tyr Val Leu Lys Leu Glu Gly Glu His Trp Thr Val Thr Val Thr
            115                 120                 125

Pro Gly Met Ser Pro Ser Leu Leu Pro Leu Glu Cys Val Gln Gly Cys
130                 135                 140

Cys Gly His Lys Gly Gly Leu Gly Ser Pro Asp Ala Val Glu Val Ser
145                 150                 155                 160

Gly Phe Asp Pro Ala Cys Leu Asp Arg Leu Ala Glu Val Met His Leu
                165                 170                 175

Pro Ser Ser Ala Ile Pro Ala Ala Leu Ala Glu Met Ser Gly Asp Ser
            180                 185                 190

Asp Arg Ser Ala Ser Pro Val Thr Thr Val Trp Thr Val Ser Gln Phe
        195                 200                 205

Phe Ala Arg His Ser Gly Gly Asn His Pro Asp Gln Val Arg Leu Gly
        210                 215                 220

Lys Ile Ile Ser Leu Cys Gln Val Ile Glu Asp Cys Cys Cys Ser Gln
225                 230                 235                 240

Asn Lys Thr Asn Arg Val Thr Pro Glu Glu Val Ala Ala Lys Ile Asp
                245                 250                 255

Leu Tyr Leu Arg Gly Ala Thr Asn Leu Glu Glu Cys Leu Ala Arg Leu
            260                 265                 270

Glu Lys Ala Arg Pro Pro Arg Val Ile Asp Thr Phe Phe Asp Trp Asp
            275                 280                 285

Val Val Leu Pro Gly Val Glu Ala Ala Thr Gln Thr Ile Lys Leu Pro
        290                 295                 300

Gln Val Asn Gln Cys Arg Ala Leu Val Pro Val Val Thr Gln Lys Ser
305                 310                 315                 320

Leu Asp Asn Asn Ser Val Pro Leu Thr Ala Phe Ser Leu Ala Asn Tyr
                325                 330                 335

Tyr Tyr Arg Ala Gln Gly Asp Glu Val Arg His Arg Glu Arg Leu Thr
            340                 345                 350

Ala Val Leu Ser Lys Leu Glu Lys Val Val Arg Glu Glu Tyr Gly Leu
            355                 360                 365

Met Pro Thr Glu Pro Gly Pro Arg Pro Thr Leu Pro Arg Gly Leu Asp
        370                 375                 380

Glu Leu Lys Asp Gln Met Glu Glu Asp Leu Leu Lys Leu Ala Asn Ala
385                 390                 395                 400

Gln Thr Thr Ser Asp Met Met Ala Trp Ala Val Glu Gln Val Asp Leu
                405                 410                 415
```

```
Lys Thr Trp Val Lys Asn Tyr Pro Arg Trp Thr Pro Pro Pro Pro
            420                 425                 430

Pro Lys Val Gln Pro Arg Lys Thr Lys Pro Val Lys Ser Leu Pro Glu
            435                 440                 445

Arg Lys Pro Val Pro Ala Pro Arg Arg Lys Val Gly Ser Asp Cys Gly
        450                 455                 460

Ser Pro Val Ser Leu Gly Gly Asp Val Pro Asn Ser Trp Glu Asp Leu
465                 470                 475                 480

Ala Val Ser Ser Pro Phe Asp Leu Pro Thr Pro Glu Pro Ala Thr
                485                 490                 495

Pro Ser Ser Glu Leu Val Ile Val Ser Ser Pro Gln Cys Ile Phe Arg
            500                 505                 510

Pro Ala Thr Pro Leu Ser Glu Pro Ala Pro Ile Pro Ala Pro Arg Gly
            515                 520                 525

Thr Val Ser Arg Pro Val Thr Pro Leu Ser Glu Pro Ile Pro Val Pro
        530                 535                 540

Ala Pro Arg Arg Lys Phe Gln Gln Val Lys Arg Leu Ser Ser Ala Ala
545                 550                 555                 560

Ala Ile Pro Pro Tyr Gln Asn Glu Pro Leu Asp Leu Ser Ala Ser Ser
                565                 570                 575

Gln Thr Glu Tyr Glu Ala Ser Pro Pro Ala Pro Pro Gln Ser Gly Gly
            580                 585                 590

Val Leu Gly Val Glu Gly His Glu Ala Glu Thr Leu Ser Glu Ile
            595                 600                 605

Ser Asp Met Ser Gly Asn Ile Lys Pro Ala Ser Val Ser Ser Ser
            610                 615                 620

Ser Leu Ser Ser Val Arg Ile Thr Arg Pro Lys Tyr Ser Ala Gln Ala
625                 630                 635                 640

Ile Ile Asp Ser Gly Gly Pro Cys Ser Gly His Leu Gln Glu Val Lys
                645                 650                 655

Glu Thr Cys Leu Ser Val Met Arg Glu Ala Cys Asp Ala Thr Lys Leu
            660                 665                 670

Asp Asp Pro Ala Thr Gln Glu Trp Leu Ser Arg Met Trp Asp Arg Val
            675                 680                 685

Asp Met Leu Thr Trp Arg Asn Thr Ser Val Tyr Gln Ala Ile Cys Thr
        690                 695                 700

Leu Asp Gly Arg Leu Lys Phe Leu Pro Lys Met Ile Leu Glu Thr Pro
705                 710                 715                 720

Pro Pro Tyr Pro Cys Glu Phe Val Met Met Pro His Thr Pro Ala Pro
                725                 730                 735

Ser Val Gly Ala Glu Ser Asp Leu Thr Ile Gly Ser Val Ala Thr Glu
            740                 745                 750

Asp Val Pro Arg Ile Leu Glu Lys Ile Glu Asn Val Gly Glu Met Ala
            755                 760                 765

Asn Gln Gly Pro Leu Ala Phe Ser Glu Asp Lys Pro Val Asp Asp Gln
        770                 775                 780

Leu Val Asn Asp Pro Arg Ile Ser Ser Arg Arg Pro Asp Glu Ser Thr
785                 790                 795                 800

Ser Ala Pro Ser Ala Gly Thr Gly Gly Ala Gly Ser Phe Thr Asp Leu
                805                 810                 815

Pro Pro Ser Asp Gly Ala Asp Ala Asp Gly Gly Pro Phe Arg Thr
            820                 825                 830
```

Val Lys Arg Lys Ala Glu Arg Leu Phe Asp Gln Leu Ser Arg Gln Val
835                 840                 845

Phe Asp Leu Val Ser His Leu Pro Val Phe Ser Arg Leu Phe Tyr
850                 855                 860

Pro Gly Gly Gly Tyr Ser Pro Gly Asp Trp Gly Phe Ala Ala Phe Thr
865                 870                 875                 880

Leu Leu Cys Leu Phe Leu Cys Tyr Ser Tyr Pro Ala Phe Gly Ile Ala
                885                 890                 895

Pro Leu Leu Gly Val Phe Ser Gly Ser Ser Arg Arg Val Arg Met Gly
                900                 905                 910

Val Phe Gly Cys Trp Leu Ala Phe Ala Val Gly Leu Phe Lys Pro Val
                915                 920                 925

Ser Asp Pro Val Gly Ala Ala Cys Glu Phe Asp Ser Pro Glu Cys Arg
930                 935                 940

Asn Ile Leu His Ser Phe Glu Leu Leu Lys Pro Trp Asp Pro Val Arg
945                 950                 955                 960

Ser Leu Val Val Gly Pro Val Gly Leu Gly Leu Ala Ile Leu Gly Arg
                965                 970                 975

Leu Leu Gly Gly Ala Arg Cys Ile Trp His Phe Leu Leu Arg Leu Gly
                980                 985                 990

Ile Val Ala Asp Cys Ile Leu Ala Gly Ala Tyr Val Leu Ser Gln Gly
            995                 1000                 1005

Arg Cys Lys Lys Cys Trp Gly Ser Cys Ile Arg Thr Ala Pro Asn
    1010                 1015                 1020

Glu Val Ala Phe Asn Val Phe Pro Phe Thr Arg Ala Thr Arg Ser
    1025                 1030                 1035

Ser Leu Ile Asp Leu Cys Asp Arg Phe Cys Ala Pro Lys Gly Met
    1040                 1045                 1050

Asp Pro Ile Phe Leu Ala Thr Gly Trp Arg Gly Cys Trp Ala Gly
    1055                 1060                 1065

Arg Ser Pro Ile Glu Gln Pro Ser Glu Lys Pro Ile Ala Phe Ala
    1070                 1075                 1080

Gln Leu Asp Glu Lys Lys Ile Thr Ala Arg Thr Val Val Ala Gln
    1085                 1090                 1095

Pro Tyr Asp Pro Asn Gln Ala Val Lys Cys Leu Arg Val Leu Gln
    1100                 1105                 1110

Ala Gly Gly Ala Met Val Ala Lys Ala Val Pro Lys Val Val Lys
    1115                 1120                 1125

Val Ser Ala Val Pro Phe Arg Ala Pro Phe Phe Pro Thr Gly Val
    1130                 1135                 1140

Lys Val Asp Pro Asp Cys Arg Val Val Val Asp Pro Asp Thr Phe
    1145                 1150                 1155

Thr Ala Ala Leu Arg Ser Gly Tyr Ser Thr Thr Asn Leu Val Leu
    1160                 1165                 1170

Gly Val Gly Asp Phe Ala Gln Leu Asn Gly Leu Lys Ile Arg Gln
    1175                 1180                 1185

Ile Ser Lys Pro Ser Gly Gly
    1190                 1195

<210> SEQ ID NO 18
<211> LENGTH: 3369
<212> TYPE: DNA
<213> ORGANISM: Porcine reproductive and respiratory syndrome virus

<400> SEQUENCE: 18

```
gctggaaaga gagcaagaaa agcacgctct tgtgcgactg ctacagtcgc tggccgcgct    60
ttgtccgttc gtgaaacccg gcaggccaag gagcacgagg ttgccggcgc caacaaggct   120
gagcacctca acactactc cccgcctgcc gaagggaatt gtggttggca ctgcatttcc   180
gccatcgcca accggatggt gaattccaaa tttgaaacca cccttcccga aagagtgaga   240
cctccagatg actgggctac tgacgaggat cttgtgaatg ccatccaaat cctcagactc   300
cctgcggcct tagacaggaa cggtgcttgt actagcgcca agtacgtact taagctggaa   360
ggtgagcatt ggactgtcac tgtgaccct gggatgtccc cttctttgct ccctcttgaa   420
tgtgttcagg gctgttgtgg gcacaagggc ggtcttggtt ccccagatgc agtcgaggtc   480
tccggatttg accctgcctg ccttgaccgg ctggctgagg tgatgcacct gcctagcagt   540
gctatcccag ccgctctggc cgaaatgtct ggcgattccg atcgttcggc ttctccggtc   600
accaccgtgt ggactgtttc gcagttcttt gcccgtcaca gcggagggaa tcaccctgac   660
caagtgcgct tagggaaaat tatcagcctt tgtcaggtga ttgaggactg ctgctgttcc   720
cagaacaaaa ccaaccgggt cacccccggag gaggtcgcag caaagattga cctgtacctc   780
cgtggtgcaa caaatcttga agaatgcttg gccaggcttg agaaagcgcg cccgccacgc   840
gtaatcgaca ccttctttga ttgggatgtt gtgctccctg gggttgaggc ggcaacccag   900
acgatcaagc tgccccaggt caaccagtgt cgtgctctgg tcctgttgt gactcaaaag   960
tccttggaca caactcggt cccctgacc gcctttcac tggctaacta ctactaccgt  1020
gcgcaaggtg acgaagttcg tcaccgtgaa agactaaccg ccgtgctctc caagttggaa  1080
aaggttgttc gagaagaata tgggctcatg ccaaccgagc ctggtccacg gcccacactg  1140
ccacgcgggc tcgacgaact caaagaccag atggaggagg acttgctgaa actggctaac  1200
gcccagacga cttcggacat gatggcctgg gcagtcgagc aggttgacct aaaaacttgg  1260
gtcaagaact acccgcggtg gacaccacca cccctccgc caaaagttca gcctcgaaaa  1320
acgaagcctg tcaagagctt gccggagaga aagcctgtcc ccgccccgcg caggaaggtt  1380
gggtccgatt gtggcagccc ggtttcatta ggcggcgatg tccctaacag ttgggaagat  1440
ttggctgtta gtagccccctt tgatctcccg accccacctg agccggcaac accttcaagt  1500
gagctggtga ttgtgtcctc accgcaatgc atcttcaggc cggcgacacc cttgagtgag  1560
ccggctccaa ttcccgcacc tcgcggaact gtgtctcgac cggtgacacc cttgagtgag  1620
ccgatccctg tgcccgcacc gcggcgtaag tttcagcagg tgaaaagatt gagttcggcg  1680
gcggcaatcc caccgtacca gaacgagccc ctggatttgt ctgcttcctc acagactgaa  1740
tatgaggcct ctccccagc accgccgcag agcgggggcg ttctgggagt agaggggcat  1800
gaagctgagg aaaccctgag tgaaatctcg gacatgtcgg gtaacattaa acctgcgtcc  1860
gtgtcatcaa gcagctcctt gtccagcgtg agaatcacac gcccaaaata ctcagctcaa  1920
gccatcatcg actcgggcgg gccctgcagt gggcatctcc aagaggtaaa ggaaacatgc  1980
cttagtgtca tgcgcgaggc atgtgatgcg actaagcttg atgaccctgc tacgcaggaa  2040
tggcttctc gcatgtggga tcgggtggac atgctgactt ggcgcaacac gtctgtttac  2100
caggcgattt gcaccttaga tggcaggtta aagttcctcc caaaaatgat actcgagaca  2160
ccgccgcct atccgggcaa gcccatcccc aacccactgc tgggtctaga ttccacctct  2220
tttaccgatt gccgccttc agatggcgcg gatgcgggacg ggggggggcc gtttcggacg  2280
gtaaaaagaa aagctgaaag gctctttgac caactgagcc gtcaggtttt tgacctcgtc  2340
```

-continued

```
tcccatctcc ctgttttctt ctcacgcctt ttctaccctg gcggtggtta ttctccgggt    2400
gattggggtt ttgcagcttt tactctattg tgcctctttt tatgttacag ttacccagcc    2460
tttggtattg ctcccctctt gggtgtgttt tctgggtctt ctcggcgcgt tcgaatgggg    2520
gttttttggct gctggttggc ttttgctgtt ggtctgttca agcctgtgtc cgacccagtc    2580
ggcgctgctt gtgagtttga ctcgccagag tgtagaaaca tccttcattc ttttgagctt    2640
ctcaaacctt gggaccctgt tcgcagcctt gttgtgggcc ccgtcggtct cggtcttgcc    2700
attcttggca ggttactggg cggggcacgc tgcatctggc acttttttgct taggcttggc    2760
attgttgcag actgtatctt ggctggagct tacgtgcttt tcaaggtag gtgtaaaaag    2820
tgctggggat cttgtataag aactgctcct aatgaggtcg cttttaacgt gtttccttc    2880
acacgtgcga ccaggtcgtc acttatcgac ctgtgcgatc ggttttgtgc gccaaaagga    2940
atggacccca ttttctcgc cactgggtgg cgcgggtgct gggccggccg aagcccatt    3000
gagcaaccct ctgaaaaacc catcgcgttt gcccaattgg atgaaaagaa gattacggct    3060
aggactgtgg tcgcccagcc ttatgacccc aaccaagccg taaagtgctt gcgggtattg    3120
caggcgggtg gggcgatggt ggctaaggcg gtcccaaaag tggtcaaggt ttccgctgtt    3180
ccattccgag cccccttctt tcccactgga gtgaaagttg accctgattg cagggtcgtg    3240
gttgaccctg acactttcac tgcagctctc cggtctggct actccaccac aaacctcgtc    3300
cttggtgtag gggactttgc ccagctgaat ggattaaaaa tcaggcaaat ttccaagcct    3360
tcagggggga                                                            3369
```

<210> SEQ ID NO 19
<211> LENGTH: 1123
<212> TYPE: PRT
<213> ORGANISM: Porcine reproductive and respiratory syndrome virus

<400> SEQUENCE: 19

```
Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190
```

```
Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Phe Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
                485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Pro Ala Pro Gln Ser Gly
            580                 585                 590

Gly Val Leu Gly Val Glu Gly His Glu Ala Glu Glu Thr Leu Ser Glu
        595                 600                 605
```

```
Ile Ser Asp Met Ser Gly Asn Ile Lys Pro Ala Ser Val Ser Ser Ser
610                 615                 620
Ser Ser Leu Ser Ser Val Arg Ile Thr Arg Pro Lys Tyr Ser Ala Gln
625                 630                 635                 640
Ala Ile Ile Asp Ser Gly Gly Pro Cys Ser Gly His Leu Gln Glu Val
            645                 650                 655
Lys Glu Thr Cys Leu Ser Val Met Arg Glu Ala Cys Asp Ala Thr Lys
            660                 665                 670
Leu Asp Asp Pro Ala Thr Gln Glu Trp Leu Ser Arg Met Trp Asp Arg
            675                 680                 685
Val Asp Met Leu Thr Trp Arg Asn Thr Ser Val Tyr Gln Ala Ile Cys
690                 695                 700
Thr Leu Asp Gly Arg Leu Lys Phe Leu Pro Lys Met Ile Leu Glu Thr
705                 710                 715                 720
Pro Pro Pro Tyr Pro Gly Lys Pro Ile Pro Asn Pro Leu Leu Gly Leu
                725                 730                 735
Asp Ser Thr Ser Phe Thr Asp Leu Pro Pro Ser Asp Gly Ala Asp Ala
            740                 745                 750
Asp Gly Gly Gly Pro Phe Arg Thr Val Lys Arg Lys Ala Glu Arg Leu
            755                 760                 765
Phe Asp Gln Leu Ser Arg Gln Val Phe Asp Leu Val Ser His Leu Pro
770                 775                 780
Val Phe Phe Ser Arg Leu Phe Tyr Pro Gly Gly Tyr Ser Pro Gly
785                 790                 795                 800
Asp Trp Gly Phe Ala Ala Phe Thr Leu Leu Cys Leu Phe Leu Cys Tyr
                805                 810                 815
Ser Tyr Pro Ala Phe Gly Ile Ala Pro Leu Leu Gly Val Phe Ser Gly
            820                 825                 830
Ser Ser Arg Arg Val Arg Met Gly Val Phe Gly Cys Trp Leu Ala Phe
    835                 840                 845
Ala Val Gly Leu Phe Lys Pro Val Ser Asp Pro Val Gly Ala Ala Cys
850                 855                 860
Glu Phe Asp Ser Pro Glu Cys Arg Asn Ile Leu His Ser Phe Glu Leu
865                 870                 875                 880
Leu Lys Pro Trp Asp Pro Val Arg Ser Leu Val Val Gly Pro Val Gly
            885                 890                 895
Leu Gly Leu Ala Ile Leu Gly Arg Leu Leu Gly Gly Ala Arg Cys Ile
            900                 905                 910
Trp His Phe Leu Leu Arg Leu Gly Ile Val Ala Asp Cys Ile Leu Ala
            915                 920                 925
Gly Ala Tyr Val Leu Ser Gln Gly Arg Cys Lys Lys Cys Trp Gly Ser
930                 935                 940
Cys Ile Arg Thr Ala Pro Asn Glu Val Ala Phe Asn Val Phe Pro Phe
945                 950                 955                 960
Thr Arg Ala Thr Arg Ser Ser Leu Ile Asp Leu Cys Asp Arg Phe Cys
                965                 970                 975
Ala Pro Lys Gly Met Asp Pro Ile Phe Leu Ala Thr Gly Trp Arg Gly
            980                 985                 990
Cys Trp Ala Gly Arg Ser Pro Ile Glu Gln Pro Ser Glu Lys Pro Ile
    995                 1000                1005
Ala Phe Ala Gln Leu Asp Glu Lys Lys Ile Thr Ala Arg Thr Val
    1010                1015                1020

Val Ala  Gln Pro Tyr Asp Pro  Asn Gln Ala Val Lys  Cys Leu Arg
```

```
               1025                1030                1035
Val Leu Gln Ala Gly Gly Ala Met Val Ala Lys Ala Val Pro Lys
        1040                1045                1050
Val Val Lys Val Ser Ala Val Pro Phe Arg Ala Pro Phe Phe Pro
        1055                1060                1065
Thr Gly Val Lys Val Asp Pro Asp Cys Arg Val Val Val Asp Pro
        1070                1075                1080
Asp Thr Phe Thr Ala Ala Leu Arg Ser Gly Tyr Ser Thr Thr Asn
        1085                1090                1095
Leu Val Leu Gly Val Gly Asp Phe Ala Gln Leu Asn Gly Leu Lys
        1100                1105                1110
Ile Arg Gln Ile Ser Lys Pro Ser Gly Gly
        1115                1120

<210> SEQ ID NO 20
<211> LENGTH: 3372
<212> TYPE: DNA
<213> ORGANISM: Porcine reproductive and respiratory syndrome virus

<400> SEQUENCE: 20
gctggaaaga gagcaagaaa agcacgctct tgtgcgactg ctacagtcgc tggccgcgct      60
ttgtccgttc gtgaaacccg gcaggccaag gagcacgagg ttgccggcgc caacaaggct     120
gagcacctca acactactc cccgcctgcc gaagggaatt gtggttggca ctgcatttcc      180
gccatcgcca accggatggt gaattccaaa tttgaaacca cccttcccga aagagtgaga     240
cctccagatg actgggctac tgacgaggat cttgtgaatg ccatccaaat cctcagactc     300
cctgcggcct tagacaggaa cggtgcttgt actagcgcca agtacgtact taagctggaa     360
ggtgagcatt ggactgtcac tgtgaccct gggatgtccc cttctttgct ccctcttgaa      420
tgtgttcagg ctgttgtgg gcacaagggc ggtcttggtt ccccagatgc agtcgaggtc      480
tccggatttg accctgcctg ccttgaccgg ctggctgagg tgatgcacct gcctagcagt     540
gctatcccag ccgctctggc cgaaatgtct ggcgattccg atcgttcggc ttctccggtc     600
accaccgtgt ggactgtttc gcagttcttt gcccgtcaca gcggagggaa tcaccctgac     660
caagtgcgct tagggaaaat tatcagcctt tgtcaggtga ttgaggactg ctgctgttcc     720
cagaacaaaa ccaaccgggt caccccggag gaggtcgcag caaagattga cctgtacctc     780
cgtggtgcaa caaatcttga agaatgcttg gccaggcttg agaaagcgcg cccgccacgc     840
gtaatcgaca ccttctttga ttgggatgtt gtgctccctg gggttgaggc ggcaacccag     900
acgatcaagc tgcccaggt caaccagtgt cgtgctctgg tccctgttgt gactcaaaag     960
tccttggaca caactcggt ccccctgacc gccttttcac tggctaacta ctactaccgt    1020
gcgcaaggtg acgaagttcg tcaccgtgaa agactaaccg ccgtgctctc caagttggaa    1080
aaggttgttc gagaagaata tgggctcatg ccaaccgagc ctggtccacg gcccacactg    1140
ccacgcgggc tcgacgaact caaagaccag atggaggagg acttgctgaa actggctaac    1200
gcccagacga cttcggacat gatggcctgg gcagtcgagc aggttgacct aaaaacttgg    1260
gtcaagaact acccgcggtg gacaccacca ccccctccgc aaaagttcga gcctcgaaaa    1320
acgaagcctg tcaagagctt gccggagaga aagcctgtcc ccgccccgcg caggaaggtt    1380
gggtccgatt gtggcagccc ggtttcatta ggcggcgatg tccctaacag ttgggaagat    1440
ttggctgtta gtaccccctt tgatctcccg acccacctg agccggcaac accttcaagt    1500
gagctggtga ttgtgtcctc accgcaatgc atcttcaggc cggcgacacc cttgagtgag    1560
```

-continued

```
ccggctccaa ttcccgcacc tcgcggaact gtgtctcgac cggtgacacc cttgagtgag      1620
ccgatccctg tgcccgcacc gcggcgtaag tttcagcagg tgaaaagatt gagttcggcg      1680
gcggcaatcc caccgtacca gaacgagccc ctggatttgt ctgcttcctc acagactgaa      1740
tatgaggcct ctcccccagc accgccgcag agcgggggcg ttctgggagt agaggggcat      1800
gaagctgagg aaaccctgag tgaaatctcg gacatgtcgg gtaacattaa acctgcgtcc      1860
gtgtcatcaa gcagctcctt gtccagcgtg agaatcacac gcccaaaata ctcagctcaa      1920
gccatcatcg actcgggcgg gccctgcagt gggcatctcc aagaggtaaa ggaaacatgc      1980
cttagtgtca tgcgcgaggc atgtgatgcg actaagcttg atgaccctgc tacgcaggaa      2040
tggctttctc gcatgtggga tcgggtggac atgctgactt ggcgcaacac gtctgtttac      2100
caggcgattt gcaccttaga tggcaggtta aagttcctcc caaaaatgat actcgagaca      2160
ccgccgccct atccgaagga gaccgcggcc gctaagttcg aacgccagca tatggattcc      2220
tcttttaccg atttgccgcc ttcagatggc gcggatgcgg acggggggg gccgtttcgg      2280
acggtaaaaa gaaaagctga aaggctcttt gaccaactga gccgtcaggt ttttgacctc      2340
gtctcccatc tccctgtttt cttctcacgc cttttctacc ctggcggtgg ttattctccg      2400
ggtgattggg gttttgcagc ttttactcta ttgtgcctct ttttatgtta cagttaccca      2460
gcctttggta ttgctcccct cttgggtgtg ttttctgggt cttctcggcg cgttcgaatg      2520
ggggttttg gctgctggtt ggcttttgct gttggtctgt tcaagcctgt gtccgaccca      2580
gtcggcgctg cttgtgagtt tgactcgcca gagtgtagaa acatccttca ttcttttgag      2640
cttctcaaac cttgggaccc tgttcgcagc cttgttgtgg gccccgtcgg tctcggtctt      2700
gccattcttg gcaggttact gggcggggca cgctgcatct ggcactttt gcttaggctt      2760
ggcattgttg cagactgtat cttggctgga gcttacgtgc tttctcaagg taggtgtaaa      2820
aagtgctggg atcttgtat aagaactgct cctaatgagg tcgcttttaa cgtgtttcct      2880
ttcacacgtg cgaccaggtc gtcacttatc gacctgtgcg atcggttttg tgcgccaaaa      2940
ggaatggacc ccatttttct cgccactggg tggcgcgggt gctgggccgg ccgaagcccc      3000
attgagcaac cctctgaaaa acccatcgcg tttgcccaat tggatgaaaa gaagattacg      3060
gctaggactg tggtcgccca gccttatgac cccaaccaag ccgtaaagtg cttgcgggta      3120
ttgcaggcgg gtggggcgat ggtggctaag gcggtcccaa aagtggtcaa ggtttccgct      3180
gttccattcc gagccccctt ctttcccact ggagtgaaag ttgaccctga ttgcagggtc      3240
gtggttgacc ctgacacttt cactgcagct ctccggtctg gctactccac cacaaacctc      3300
gtccttggtg tagggacttt gcccagctg aatggattaa aaatcaggca aatttccaag      3360
ccttcagggg ga                                                          3372
```

<210> SEQ ID NO 21
<211> LENGTH: 1124
<212> TYPE: PRT
<213> ORGANISM: Porcine reproductive and respiratory syndrome virus

<400> SEQUENCE: 21

```
Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45
```

-continued

```
Pro Ala Glu Gly Asn Cys Gly Trp His Cys Ile Ser Ala Ile Ala Asn
        50                  55                  60
Arg Met Val Asn Ser Lys Phe Glu Thr Thr Leu Pro Glu Arg Val Arg
 65                  70                  75                  80
Pro Pro Asp Asp Trp Ala Thr Asp Glu Asp Leu Val Asn Ala Ile Gln
                    85                  90                  95
Ile Leu Arg Leu Pro Ala Ala Leu Asp Arg Asn Gly Ala Cys Thr Ser
                100                 105                 110
Ala Lys Tyr Val Leu Lys Leu Glu Gly Glu His Trp Thr Val Thr Val
            115                 120                 125
Thr Pro Gly Met Ser Pro Ser Leu Leu Pro Leu Glu Cys Val Gln Gly
        130                 135                 140
Cys Cys Gly His Lys Gly Gly Leu Gly Ser Pro Asp Ala Val Glu Val
145                 150                 155                 160
Ser Gly Phe Asp Pro Ala Cys Leu Asp Arg Leu Ala Glu Val Met His
                165                 170                 175
Leu Pro Ser Ser Ala Ile Pro Ala Ala Leu Ala Glu Met Ser Gly Asp
                180                 185                 190
Ser Asp Arg Ser Ala Ser Pro Val Thr Thr Val Trp Thr Val Ser Gln
            195                 200                 205
Phe Phe Ala Arg His Ser Gly Gly Asn His Pro Asp Gln Val Arg Leu
        210                 215                 220
Gly Lys Ile Ile Ser Leu Cys Gln Val Ile Glu Asp Cys Cys Cys Ser
225                 230                 235                 240
Gln Asn Lys Thr Asn Arg Val Thr Pro Glu Glu Val Ala Ala Lys Ile
                245                 250                 255
Asp Leu Tyr Leu Arg Gly Ala Thr Asn Leu Glu Glu Cys Leu Ala Arg
                260                 265                 270
Leu Glu Lys Ala Arg Pro Pro Arg Val Ile Asp Thr Phe Phe Asp Trp
            275                 280                 285
Asp Val Val Leu Pro Gly Val Glu Ala Ala Thr Gln Thr Ile Lys Leu
        290                 295                 300
Pro Gln Val Asn Gln Cys Arg Ala Leu Val Pro Val Thr Gln Lys
305                 310                 315                 320
Ser Leu Asp Asn Asn Ser Val Pro Leu Thr Ala Phe Ser Leu Ala Asn
                325                 330                 335
Tyr Tyr Tyr Arg Ala Gln Gly Asp Glu Val Arg His Arg Glu Arg Leu
                340                 345                 350
Thr Ala Val Leu Ser Lys Leu Glu Lys Val Val Arg Glu Glu Tyr Gly
            355                 360                 365
Leu Met Pro Thr Glu Pro Gly Pro Arg Pro Thr Leu Pro Arg Gly Leu
        370                 375                 380
Asp Glu Leu Lys Asp Gln Met Glu Glu Asp Leu Leu Lys Leu Ala Asn
385                 390                 395                 400
Ala Gln Thr Thr Ser Asp Met Met Ala Trp Ala Val Glu Gln Val Asp
                405                 410                 415
Leu Lys Thr Trp Val Lys Asn Tyr Pro Arg Trp Thr Pro Pro Pro
            420                 425                 430
Pro Pro Lys Val Gln Pro Arg Lys Thr Lys Pro Val Lys Ser Leu Pro
            435                 440                 445
Glu Arg Lys Pro Val Pro Ala Pro Arg Arg Lys Val Gly Ser Asp Cys
450                 455                 460
```

```
Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
            485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
            515                 520                 525

Gly Thr Val Ser Arg Pro Val Thr Pro Leu Ser Glu Pro Ile Pro Val
        530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Pro Ala Pro Pro Gln Ser Gly
            580                 585                 590

Gly Val Leu Gly Val Glu Gly His Glu Ala Glu Thr Leu Ser Glu
    595                 600                 605

Ile Ser Asp Met Ser Gly Asn Ile Lys Pro Ala Ser Val Ser Ser Ser
            610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
            675                 680                 685

Val Asp Met Leu Thr Trp Arg Asn Thr Ser Val Tyr Gln Ala Ile Cys
    690                 695                 700

Thr Leu Asp Gly Arg Leu Lys Phe Leu Pro Lys Met Ile Leu Glu Thr
705                 710                 715                 720

Pro Pro Pro Tyr Pro Lys Glu Thr Ala Ala Ala Lys Phe Glu Arg Gln
                725                 730                 735

His Met Asp Ser Ser Phe Thr Asp Leu Pro Ser Asp Gly Ala Asp
            740                 745                 750

Ala Asp Gly Gly Gly Pro Phe Arg Thr Val Lys Arg Lys Ala Glu Arg
            755                 760                 765

Leu Phe Asp Gln Leu Ser Arg Gln Val Phe Asp Leu Val Ser His Leu
            770                 775                 780

Pro Val Phe Phe Ser Arg Leu Phe Tyr Pro Gly Gly Tyr Ser Pro
785                 790                 795                 800

Gly Asp Trp Gly Phe Ala Ala Phe Thr Leu Leu Cys Leu Phe Leu Cys
            805                 810                 815

Tyr Ser Tyr Pro Ala Phe Gly Ile Ala Pro Leu Leu Gly Val Phe Ser
            820                 825                 830

Gly Ser Ser Arg Arg Val Arg Met Gly Val Phe Gly Cys Trp Leu Ala
            835                 840                 845

Phe Ala Val Gly Leu Phe Lys Pro Val Ser Asp Pro Val Gly Ala Ala
            850                 855                 860

Cys Glu Phe Asp Ser Pro Glu Cys Arg Asn Ile Leu His Ser Phe Glu
865                 870                 875                 880

Leu Leu Lys Pro Trp Asp Pro Val Arg Ser Leu Val Val Gly Pro Val
```

```
            885                 890                 895
Gly Leu Gly Leu Ala Ile Leu Gly Arg Leu Gly Gly Ala Arg Cys
                900                 905                 910
Ile Trp His Phe Leu Leu Arg Leu Gly Ile Val Ala Asp Cys Ile Leu
            915                 920                 925
Ala Gly Ala Tyr Val Leu Ser Gln Gly Arg Cys Lys Lys Cys Trp Gly
        930                 935                 940
Ser Cys Ile Arg Thr Ala Pro Asn Glu Val Ala Phe Asn Val Phe Pro
945                 950                 955                 960
Phe Thr Arg Ala Thr Arg Ser Ser Leu Ile Asp Leu Cys Asp Arg Phe
                965                 970                 975
Cys Ala Pro Lys Gly Met Asp Pro Ile Phe Leu Ala Thr Gly Trp Arg
            980                 985                 990
Gly Cys Trp Ala Gly Arg Ser Pro Ile Glu Gln Pro Ser Glu Lys Pro
        995                 1000                1005
Ile Ala Phe Ala Gln Leu Asp Glu Lys Lys Ile Thr Ala Arg Thr
    1010                1015                1020
Val Val Ala Gln Pro Tyr Asp Pro Asn Gln Ala Val Lys Cys Leu
    1025                1030                1035
Arg Val Leu Gln Ala Gly Gly Ala Met Val Ala Lys Ala Val Pro
    1040                1045                1050
Lys Val Val Lys Val Ser Ala Val Pro Phe Arg Ala Pro Phe Phe
    1055                1060                1065
Pro Thr Gly Val Lys Val Asp Pro Asp Cys Arg Val Val Val Asp
    1070                1075                1080
Pro Asp Thr Phe Thr Ala Ala Leu Arg Ser Gly Tyr Ser Thr Thr
    1085                1090                1095
Asn Leu Val Leu Gly Val Gly Asp Phe Ala Gln Leu Asn Gly Leu
    1100                1105                1110
Lys Ile Arg Gln Ile Ser Lys Pro Ser Gly Gly
    1115                1120

<210> SEQ ID NO 22
<211> LENGTH: 3393
<212> TYPE: DNA
<213> ORGANISM: Porcine reproductive and respiratory syndrome virus

<400> SEQUENCE: 22
gctggaaaga gagcaagaaa agcacgctct tgtgcgactg ctacagtcgc tggccgcgct        60
ttgtccgttc gtgaaacccg gcaggccaag gagcacgagg ttgccggcgc caacaaggct       120
gagcacctca acactactc cccgcctgcc gaagggaatt gtggttggca ctgcatttcc        180
gccatcgcca accggatggt gaattccaaa tttgaaacca ccttcccga aagagtgaga        240
cctccagatg actgggctac tgacgaggat cttgtgaatg ccatccaaat cctcagactc       300
cctgcggcct tagacaggaa cggtgcttgt actagcgcca gtacgtact taagctggaa        360
ggtgagcatt ggactgtcac tgtgaccct gggatgtccc cttctttgct ccctcttgaa       420
tgtgttcagg ctgttgtgg cacaagggc ggtcttggtt ccccagatgc agtcgaggtc        480
tccggatttg accctgcctg ccttgaccgg ctggctgagg tgatgcacct gcctagcagt       540
gctatcccag ccgctctggc cgaaatgtct ggcgattccg atcgttcggc ttctccggtc       600
accaccgtgt ggactgtttc gcagttcttt gcccgtcaca gcggagggaa tcaccctgac       660
caagtgcgct tagggaaaat tatcagcctt tgtcaggtga ttgaggactg ctgctgttcc       720
```

```
cagaacaaaa ccaaccgggt cacccggag gaggtcgcag caaagattga cctgtacctc    780
cgtggtgcaa caaatcttga agaatgcttg gccaggcttg agaaagcgcg cccgccacgc    840
gtaatcgaca ccttctttga ttgggatgtt gtgctccctg gggttgaggc ggcaacccag    900
acgatcaagc tgccccaggt caaccagtgt cgtgctctgg tccctgttgt gactcaaaag    960
tccttggaca caactcggt cccctgacc gccttttcac tggctaacta ctactaccgt   1020
gcgcaaggtg acgaagttcg tcaccgtgaa agactaaccg ccgtgctctc caagttggaa   1080
aaggttgttc gagaagaata tgggctcatg ccaaccgagc ctggtccacg cccacactg   1140 ccacgcgggc tcgacgaact caaagaccag atggaggagg acttgctgaa actggctaac   1200
gcccagacga cttcggacat gatggcctgg gcagtcgagc aggttgacct aaaaacttgg   1260
gtcaagaact acccgcggtg gacaccacca ccccctccgc caaaagttca gcctcgaaaa   1320
acgaagcctg tcaagagctt gccggagaga aagcctgtcc ccgccccgcg caggaaggtt   1380
gggtccgatt gtggcagccc ggttttcatta ggcggcgatg tccctaacag ttgggaagat   1440
ttggctgtta gtagcccctt tgatctcccg accccacctg agccggcaac accttcaagt   1500
gagctggtga ttgtgtcctc accgcaatgc atcttcaggc cggcgacacc cttgagtgag   1560
ccggctccaa ttcccgcacc tcgcggaact gtgtctcgac cggtgacacc cttgagtgag   1620
ccgatccctg tgcccgcacc gcggcgtaag tttcagcagg tgaaaagatt gagttcggcg   1680
gcggcaatcc caccgtacca gaacgagccc ctggatttgt ctgcttcctc acagactgaa   1740
tatgaggcct ctcccccagc accgccgcag agcgggggcg ttctgggagt agaggggcat   1800
gaagctgagg aaaccctgag tgaaatctcg gacatgtcgg gtaacattaa acctgcgtcc   1860
gtgtcatcaa gcagctcctt gtccagcgtg agaatcacac gcccaaaata ctcagctcaa   1920
gccatcatcg actcgggcgg gccctgcagt gggcatctcc aagaggtaaa ggaaacatgc   1980
cttagtgtca tgcgcgaggc atgtgatgcg actaagcttg atgaccctgc tacgcaggaa   2040
tggctttctc gcatgtggga tcgggtggac atgctgactt ggcgcaacac gtctgtttac   2100
caggcgattt gcaccttaga tggcaggtta agttcctcc caaaaatgat actcgagaca   2160
ccgccgccct atccggatta taaggatcat gacggcgatt acaaggatca cgatatcgac   2220
tacaaggatg acgatgacaa gtcttttacc gatttgccgc cttcagatgg cgcggatgcg   2280 gacgggggg ggccgtttcg gacggtaaaa agaaaagctg aaaggctctt tgaccaactg   2340
agccgtcagg ttttttgacct cgtctcccat ctccctgttt tcttctcacg ccttttctac   2400
cctggcggtg gttattctcc gggtgattgg ggttttgcag cttttactct attgtgcctc   2460
tttttatgtt acagttaccc agcctttggt attgctcccc tcttgggtgt gttttctggg   2520
tcttctcggc gcgttcgaat gggggttttt ggctgctggt tggcttttgc tgttggtctg   2580
ttcaagcctg tgtccgaccc agtcggcgct gcttgtgagt ttgactcgcc agagtgtaga   2640
aacatccttc attcttttga gcttctcaaa ccttgggacc ctgttcgcag ccttgttgtg   2700
ggccccgtcg gtctcggtct tgccattctt ggcaggttac tgggcggggc acgctgcatc   2760
tggcactttt tgcttaggct tggcattgtt gcagactgta tcttggctgg agcttacgtg   2820
ctttctcaag gtaggtgtaa aaagtgctgg ggatcttgta taagaactgc tcctaatgag   2880
gtcgctttta acgtgtttcc tttcacacgt gcgaccaggt cgtcacttat cgacctgtgc   2940
gatcggtttt gtgcgccaaa aggaatggac cccatttttc tcgccactgg gtggcgcggg   3000
tgctgggccg gccgaagccc cattgagcaa ccctctgaaa acccatcgc gtttgcccaa   3060 ttggatgaaa agaagattac ggctaggact gtggtcgccc agccttatga ccccaaccaa   3120
```

-continued

```
gccgtaaagt gcttgcgggt attgcaggcg ggtggggcga tggtggctaa ggcggtccca   3180
aaagtggtca aggtttccgc tgttccattc cgagccccct tctttcccac tggagtgaaa   3240
gttgaccctg attgcagggt cgtggttgac cctgacactt tcactgcagc tctccggtct   3300
ggctactcca ccacaaacct cgtccttggt gtagggact ttgcccagct gaatggatta    3360
aaaatcaggc aaatttccaa gccttcaggg gga                                3393
```

<210> SEQ ID NO 23
<211> LENGTH: 1131
<212> TYPE: PRT
<213> ORGANISM: Porcine reproductive and respiratory syndrome virus

<400> SEQUENCE: 23

```
Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
                20                  25                  30

Glu Val Ala Gly Ala Asn Lys Ala Glu His Leu Lys His Tyr Ser Pro
            35                  40                  45

Pro Ala Glu Gly Asn Cys Gly Trp His Cys Ile Ser Ala Ile Ala Asn
        50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Phe Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320
```

```
Ser Leu Asp Asn Asn Ser Val Pro Leu Thr Ala Phe Ser Leu Ala Asn
            325                 330                 335

Tyr Tyr Tyr Arg Ala Gln Gly Asp Glu Val Arg His Arg Glu Arg Leu
        340                 345                 350

Thr Ala Val Leu Ser Lys Leu Glu Lys Val Val Arg Glu Glu Tyr Gly
            355                 360                 365

Leu Met Pro Thr Glu Pro Gly Pro Arg Pro Thr Leu Pro Arg Gly Leu
370                 375                 380

Asp Glu Leu Lys Asp Gln Met Glu Glu Asp Leu Lys Leu Ala Asn
385                 390                 395                 400

Ala Gln Thr Thr Ser Asp Met Met Ala Trp Ala Val Glu Gln Val Asp
            405                 410                 415

Leu Lys Thr Trp Val Lys Asn Tyr Pro Arg Trp Thr Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
        450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
            485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
            565                 570                 575

Ser Gln Thr Glu Tyr Glu Ala Ser Pro Pro Ala Pro Pro Gln Ser Gly
        580                 585                 590

Gly Val Leu Gly Val Glu Gly His Glu Ala Glu Glu Thr Leu Ser Glu
    595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
            645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Cys
    690                 695                 700

Thr Leu Asp Gly Arg Leu Lys Phe Leu Pro Lys Met Ile Leu Glu Thr
705                 710                 715                 720

Pro Pro Pro Tyr Pro Asp Tyr Lys Asp His Asp Gly Asp Tyr Lys Asp
            725                 730                 735

His Asp Ile Asp Tyr Lys Asp Asp Asp Lys Ser Phe Thr Asp Leu
```

```
                    740                 745                 750
Pro Pro Ser Asp Gly Ala Asp Ala Asp Gly Gly Pro Phe Arg Thr
        755                 760                 765
Val Lys Arg Lys Ala Glu Arg Leu Phe Asp Gln Leu Ser Arg Gln Val
    770                 775                 780
Phe Asp Leu Val Ser His Leu Pro Val Phe Phe Ser Arg Leu Phe Tyr
785                 790                 795                 800
Pro Gly Gly Gly Tyr Ser Pro Gly Asp Trp Gly Phe Ala Ala Phe Thr
                805                 810                 815
Leu Leu Cys Leu Phe Leu Cys Tyr Ser Tyr Pro Ala Phe Gly Ile Ala
            820                 825                 830
Pro Leu Leu Gly Val Phe Ser Gly Ser Ser Arg Arg Val Arg Met Gly
        835                 840                 845
Val Phe Gly Cys Trp Leu Ala Phe Ala Val Gly Leu Phe Lys Pro Val
    850                 855                 860
Ser Asp Pro Val Gly Ala Ala Cys Glu Phe Asp Ser Pro Glu Cys Arg
865                 870                 875                 880
Asn Ile Leu His Ser Phe Glu Leu Leu Lys Pro Trp Asp Pro Val Arg
                885                 890                 895
Ser Leu Val Val Gly Pro Val Gly Leu Gly Leu Ala Ile Leu Gly Arg
            900                 905                 910
Leu Leu Gly Gly Ala Arg Cys Ile Trp His Phe Leu Leu Arg Leu Gly
        915                 920                 925
Ile Val Ala Asp Cys Ile Leu Ala Gly Ala Tyr Val Leu Ser Gln Gly
    930                 935                 940
Arg Cys Lys Lys Cys Trp Gly Ser Cys Ile Arg Thr Ala Pro Asn Glu
945                 950                 955                 960
Val Ala Phe Asn Val Phe Pro Phe Thr Arg Ala Thr Arg Ser Ser Leu
                965                 970                 975
Ile Asp Leu Cys Asp Arg Phe Cys Ala Pro Lys Gly Met Asp Pro Ile
            980                 985                 990
Phe Leu Ala Thr Gly Trp Arg Gly Cys Trp Ala Gly Arg Ser Pro Ile
        995                 1000                1005
Glu Gln Pro Ser Glu Lys Pro Ile Ala Phe Ala Gln Leu Asp Glu
    1010                1015                1020
Lys Lys Ile Thr Ala Arg Thr Val Val Ala Gln Pro Tyr Asp Pro
    1025                1030                1035
Asn Gln Ala Val Lys Cys Leu Arg Val Leu Gln Ala Gly Gly Ala
    1040                1045                1050
Met Val Ala Lys Ala Val Pro Lys Val Val Lys Val Ser Ala Val
    1055                1060                1065
Pro Phe Arg Ala Pro Phe Phe Pro Thr Gly Val Lys Val Asp Pro
    1070                1075                1080
Asp Cys Arg Val Val Val Asp Pro Asp Thr Phe Thr Ala Ala Leu
    1085                1090                1095
Arg Ser Gly Tyr Ser Thr Thr Asn Leu Val Leu Gly Val Gly Asp
    1100                1105                1110
Phe Ala Gln Leu Asn Gly Leu Lys Ile Arg Gln Ile Ser Lys Pro
    1115                1120                1125
Ser Gly Gly
    1130

<210> SEQ ID NO 24
```

<211> LENGTH: 1520
<212> TYPE: DNA
<213> ORGANISM: Artificial Sequence
<220> FEATURE:
<223> OTHER INFORMATION: Chemically Synthesized

<400> SEQUENCE: 24

```
gagcaaaagg ccagcaaaag gccaggaacc gtaaaaaggc cgcgttgctg gcgttttttcc      60
ataggctccg ccccccctgac gagcatcaca aaaatcgacg ctcaagtcag aggtggcgaa     120
acccgacagg actataaaga taccaggcgt ttccccctgg aagctccctc gtgcgctctc     180
ctgttccgac cctgccgctt accggatacc tgtccgcctt tctcccttcg ggaagcgtgg     240
cgctttctca tagctcacgc tgtaggtatc tcagttcggt gtaggtcgtt cgctccaagc     300
tgggctgtgt gcacgaaccc cccgttcagc ccgaccgctg cgccttatcc ggtaactatc     360
gtcttgagtc caacccggta agacacgact tatcgccact ggcagcagcc actggtaaca     420
ggattagcag agcgaggtat gtaggcggtg ctacagagtt cttgaagtgg tggcctaact     480
acggctacac tagaagaaca gtatttggta tctgcgctct gctgaagcca gttaccttcg     540
gaaaaagagt tggtagctct tgatccggca acaaaccac cgctggtagc ggtggttttt     600
ttgtttgcaa gcagcagatt acgcgcagaa aaaaggatc tcaagaagat cctttgatct     660
tttctacggg gtctgacgct cagtggaacg aaaactcacg ttaagggatt ttggtcatga     720
gattatcaaa aaggatcttc acctagatcc ttttaaatta aaaatgaagt tttagcacgt     780
gtcagtcctg ctcctcggcc acgaagtgca cgcagttgcc ggccgggtcg cgcagggcga     840
actcccgccc ccacggctgc tcgccgatct cggtcatggc cggcccggag cgtcccgga     900
agttcgtgga cacgacctcc gaccactcgg cgtacagctc gtccaggccg cgcacccaca     960
cccaggccag ggtgttgtcc ggcaccacct ggtcctggac cgcgctgatg aacagggtca    1020
cgtcgtcccg gaccacaccg gcgaagtcgt cctccacgaa gtcccgggag aacccgagcc    1080
ggtcggtcca gaactcgacc gctccggcga cgtcgcgcgc ggtgagcacc ggaacggcac    1140
tggtcaactt ggccatggtg gccctcctca cgtgctatta ttgaagcatt tatcagggtt    1200
attgtctcat gagcggatac atatttgaat gtatttagaa aaataaacaa ataggggttc    1260
cgcgcacatt tccccgaaaa gtgccacctg atgcggtgtg aaataccgca cagatgcgta    1320
aggagaaaat accgcatcag gaaattgtaa gcgttaataa ttcagaagaa ctcgtcaaga    1380
aggcgataga aggcgatgcg ctgcgaatca ggggataacg caggaaagaa catgtactag    1440
taggcctaga tctgcatgcg aattccgcgg atccggccgg cccgggctct agactcgaga    1500
agcttttaat taaaccatgt                                                 1520
```

<210> SEQ ID NO 25
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 25

```
gcggaggctg caagttaatg gtctc                                             25
```

<210> SEQ ID NO 26
<211> LENGTH: 25
<212> TYPE: DNA
<213> ORGANISM: Artificial Sequence
<220> FEATURE:
<223> OTHER INFORMATION: Chemically Synthesized

```
<400> SEQUENCE: 26
cgcagggagt ctgaggattt ggatg                                          25

<210> SEQ ID NO 27
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 27
gcggaggctg caagttaatg gtctc                                          25

<210> SEQ ID NO 28
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 28
gcggaggctg caagttaatg gtctc                                          25

<210> SEQ ID NO 29
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 29
gggcatctcc aagaggtaaa ggaaac                                         26

<210> SEQ ID NO 30
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 30
gaggcacaat agagtaaaag ctgcaaaac                                      29

<210> SEQ ID NO 31
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 31
gggcatctcc aagaggtaaa ggaaac                                         26

<210> SEQ ID NO 32
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 32
ctgtgcctgc ggacggagct gatg                                           24

<210> SEQ ID NO 33
```

```
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 33
ccttctttct cttctgctgc ttgccgttgt tatttggcat                    40

<210> SEQ ID NO 34
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 34
ggtggaatct agacccagca gtgggttggg gatgggcttg cc                 42

<210> SEQ ID NO 35
<211> LENGTH: 66
<212> TYPE: DNA
<213> ORGANISM: Artificial Sequence
<220> FEATURE:
<223> OTHER INFORMATION: Chemically Synthesized

<400> SEQUENCE: 35
cttgtcatcg tcatccttgt agtcgatatc gtgatccttg taatcgccgt catgatcctt    60
ataatc                                                              66

<210> SEQ ID NO 36
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 36
aatccatatg ctggcgttcg aacttagcgg cc                            32
```